US008815235B2

(12) United States Patent
Schnitzer et al.

(10) Patent No.: US 8,815,235 B2
(45) Date of Patent: Aug. 26, 2014

(54) TISSUE-SPECIFIC IMAGING AND THERAPEUTIC AGENTS TARGETING PROTEINS EXPRESSED ON LUNG ENDOTHELIAL CELL SURFACE

(75) Inventors: Jan E. Schnitzer, Encinitas, CA (US); Philip Oh, San Diego, CA (US)

(73) Assignee: Jan E. Schnitzer, San Diego, CA (US)

(*) Notice: Subject to any disclaimer, the term of this patent is extended or adjusted under 35 U.S.C. 154(b) by 247 days.

(21) Appl. No.: 11/143,114

(22) Filed: Jun. 2, 2005

(65) Prior Publication Data

US 2006/0024231 A1 Feb. 2, 2006

Related U.S. Application Data

(60) Provisional application No. 60/576,114, filed on Jun. 2, 2004.

(51) Int. Cl.
*A61K 39/395* (2006.01)

(52) U.S. Cl.
USPC ...................................................... 424/130.1

(58) Field of Classification Search
CPC ................................ C07K 16/40; C12N 9/48
See application file for complete search history.

(56) References Cited

U.S. PATENT DOCUMENTS

| 5,855,866 A | 1/1999 | Thorpe et al. |
| 6,261,535 B1 | 7/2001 | Thorpe et al. |
| 7,125,541 B2 | 10/2006 | Thorpe et al. |
| 7,182,933 B2 | 2/2007 | Goetz et al. |
| 2003/0008819 A1 | 1/2003 | Schnitzer et al. |
| 2003/0232762 A1* | 12/2003 | Ruoslahti et al. ............. 514/16 |

FOREIGN PATENT DOCUMENTS

| TW | 200600784 | 1/2006 |
| WO | WO 98/53852 | 12/1998 |
| WO | WO 99/13329 | 3/1999 |
| WO | WO 00/78361 A2 | 12/2000 |
| WO | WO 02/30473 A1 | 4/2002 |
| WO | WO 03/018048 A1 | 3/2003 |
| WO | WO 2005/117977 A2 | 12/2005 |

OTHER PUBLICATIONS

Silistino-Souza et al in "Annexin 1: differential expression in tumor and mast cells in human larynx cancer" Int. J. Cancer: vol. 120, p. 2582-2589 (2007).*
Coupade et al in "Annexin 1 Expression and Phosphorylation Are Upregulated during Liver Regeneration and Transformation in Antithrombin III SV40 T Large T Antigen Transgenic Mice" Hepatology, Feb. 2000, p. 371-380.*
Dendorfer et al., in "Potentiation of the vascular response to kinins by inhibition of myocardial kininases" (Hypertension. Jan. 2000, vol. 35: p. 32-7).*
Matsui et al in "Lymphatic Microvessels in th Rat Remnant Kidney Model of Renal Fibrosis: Aminopeptidase P and Podoplanin Are Discriminatory Markers for Endothelial Cells of Blood and Lymphatic Vessels", (J Am Soc Nephrol. Aug. 2003, vol. 14: p. 1981-1989).*
McKanna, J. A. and Zhang, M., "Immunohistochemical Localization of Lipocortin 1 in Rat Brain is Sensitive to pH, Freezing, and Dehydration," *J. Histochem. & Cytochem.*, 45(4): 527-538 (1997).
Savchenko, V. L., et al., "Microglia and Astrocytes in the Adult Rat Brain: Comparative Immunocytochemical Analysis Demonstrates the Efficacy of Lipocortin 1 Immunoreactivity," *Neurosci.*, 96(1): 195-203 (2000).
Eberhard, D. A., et al., "Alterations of Annexin Expression in Pathological Neuronal and Glial Reactions," 145(3): 640-649 (1994).
Dreier, R., et al., "Differential Expression of Annexins I, II and IV in Human Tissues: an Immunohistochemical Study," *Histochem Cell Biol.*, 110(2): 137-148 (1998).
Pencil, S. D. and Toth, M., "Elevated Levels of Annexin I Protein in vitro and in vivo in Rat and Human Mammary Adenocarcinoma," *Clin. Exp. Metastasis*, 16(2): 113-121 (1998).
Ahn, S., et al. "Differential Expression of Annexin I in Human Mammary Ductal Epithelial Cells in Normal and Benign and Malignant Breast Tissues," *Clin. Exp. Metastasis*, 15(2): 151-156 (1997).
Anzick, S. L., et al. "Role of Genomics in Identifying New Targets for Cancer Therapy," *Onocology, Suppl. No. 4*, 16(5): 7-13 (2002).
Dvorak, H. F., et al., "Structure of Solid Tumors and Their Vasculature: Implications for Therapy With Monoclonal Antibodies," *Cancer Cells*, 3(2): 77-85 (1991).
Schwartz-Albiez, R., et al., "Differential Expression of Annexins I and II in Normal and Malignant Human Mammary Epithelial Cells," *Differentiation*, 52: 229-237 (1993).
Gerke, V. And Moss, S. E., "Annexins: From Structure to Function," *Am. Physiol. Soc.*, 82: 331-371 (2002).
Traverso, V., et al., "Lipocortin 1 (annexin 1) in Patches Associated With the Membrane of a Lung Adenocarcinoma Cell Line and in the Cell Cytoplasm," *J. Cell Sci.*, 111: 1405-1418 (1998).
Guzmán-Aránguez, A., et al., "Differentiation of Human Colon Adenocarcinoma Cells Alters the Expression and Intracellular Localization of Annexins A1, A2 and A5," *J. Of Cell. Biochem.*, 94: 178-193 (2005).
Naciff, J. M., et al., "Differential Expression of Annexins I-VI in the Rat Dorsal Root Ganglia and Spinal Cord," *J. Compar. Neurol.*, 368: 356-370 (1996).
Shen, D., et al., "Loss of Annexin A1 Expression in Human Breast Cancer Detected by Multiple High-Throughput Analyses," *Biochem. and Biophys. Research Comm.*, 326: 218-227 (2005).
Carver, L. A. and Schnitzer, J. E., "Caveolae: Mining Little Caves for New Cancer Targets," *Nature*, 3: 571-581 (2003).
McIntosh, D. P. And Schnitzer, J. E., "Caveolae Require Intact VAMP For Targeted Transport in Vascular Endothelium," *Am. Physio. Soc.*, H222-H2232 (1999).
Schnitzer, J. E., et al., "NEM Inhibits Transcytosis, Endocytosis and Capillary Permeability: Implication of Caveolae Fusion in Endothelia," *Am. Physio. Soc.*, H48-H55 (1995).

(Continued)

*Primary Examiner* — Ilia Ouspenski
(74) *Attorney, Agent, or Firm* — Hamilton, Brook, Smith & Reynolds, P.C.

(57) ABSTRACT

Methods of delivering an agent in a tissue-specific manner, particularly lung tissue, by targeting a protein expressed on the endothelial cell surface, are described. The methods can be used for detecting, imaging and/or treating pathologies, as well as for diagnostics.

2 Claims, No Drawings

(56) References Cited

OTHER PUBLICATIONS

Schnitzer, J. E., et al., "Endothelial Caveolae Have the Molecular Transport Machinery For Vesicle Budding, Docking, and Fusion Including VAMP, NSF, SNAP, Annexins, and GTPases," *J. Biol. Chem.*, 270(24): 14399-14404 (1996).

Schnitzer, J. E., et al., "Filipin-Sensitive Caveolae-Mediated Transport in Endothelium: Reduced Transcytosis, Scavenger Endocytosis, and Capillary Permeability of Select Macromolecules," *J. Cell Biol.*, 127(5): 1217-1232 (1994).

Schnitzer, J. E., "Caveolae: From Basic Trafficking Mechanisms to Targeting Transcytosis For Tissue-Specific Drug and Gene Delivery in vivo," *Adv. Drug Deliv. Rev.*, 49: 265-280 (2001).

Schnitzer, J. E. and Oh, Phil, "Albondin-Mediated Capillary Permeability to Albumin," *J. Biol. Chem.*, 269(8): 6072-6082 (1994).

Schnitzer, J. E., et al., "Separation of Caveolae From Associated Microdomains of GPI-Anchored Proteins," *Science*, 269: 1435-1439 (1995).

Schnitzer, J. E., et al., "Role of GTP Hydrolysis in Fission of Caveolae Directly From Plasma Membranes," *Science*, 274: 239-242 (1996).

Contag, C. H. and Bachmann, M. H., "The Writing is on the Vessel Wall," *Nature*, 429: 618-619 (2004).

Oh, P., et al., "Subtractive Proteomic Mapping of the Endothelial Surface in Lung and Solid Tumours For Tissue-Specific Therapy," *Nature*, 429: 629-635 (2004).

Brichory, F. M., et al., "An Immune Response Manifested by the Common Occurrence of Annexins I and II Autoantibodies and High Circulating Levels of IL-6 in Lung Cancer," *Proc. Natl. Acad. Sci.,*, 98(17): 9824-9829 (2001).

McIntosh, D. P., et al., "Targeting Endothelium and its Dynamic Caveolae For Tissue-Specific Transcytosis in vivo: A Pathway to Overcome Cell Barriers to Drug and Gene Delivery," *Proc. Natl. Acad. Sci.,*, 99(4): 1996-2001 (2002).

Drews, J., "Drug Discovery: A Historical Perspective," *Science*, 287: 1960-1964 (2000).

Lindsay, M. A., "Target Discovery," *Nature Rev.*, 2: 831-838 (2003).

Workman, P., "New Drug Targets for Genomic Cancer Therapy: Successes, Limitations, Opportunities and Future Challenges," *Curr. Cancer Drug Targets*, pp. 33-47 (2001).

Cavenee, W. K., "Genetics and New Approaches to Cancer Therapy," *Carcinogen.*, 28(5): 683-686 (2002).

Huber, L. A., "Is Proteomics Heading in the Wrong Direction?," *Nature Rev.*, 4: 74-80 (2003).

Perou, C. M., et al., "Molecular Portraits of Human Breast Tumors," *Nature*, 406: 747-752 (2000).

Jain, R. K., "The Next Frontier of Molecular Medicine: Delivery of Therapeutics," *Nature Med.*, 4(6): 655-657 (1998).

Massoud, T. F. and Gambhir, S. S., "Molecular Imaging in Living Subjects: Seeing Fundamental Biological Processes in a New Light," *Genes & Devel.*, 17: 545-580 (2003).

Herschman, H. R., "Molecular Imaging: Looking at Problems, Seeing Solutions," *Science*, 302: 605-608 (2003).

Rudin, M. and Weissleder, R., "Molecular Imaging in Drug Discovery and Development," *Nature Rev.*, 2: 123-131 (2003).

Weissleder, R., "Scaling Down Imaging: Molecular Mapping of Cancer in Mice," *Nature Rev.* 2: 1-8 (2001).

Pasqualini, R. and Ruoslahti, E., "Organ Targeting in vivo Using Phage Display Peptide Libraries," *Nature*, 380: 364-366 (1996).

Muzykantov, V. R., et al., "Immunotargeting of Antioxidant Enzymes to the Pulmonary Endothelium," *Proc. Natl. Acad. Sci.*, 93: pp. 5213-5218 (1996).

Muzykantov, V. R., et al., "Streptavidin Facilitates Internalization and Pulmonary Targeting of an Anti-Endothelial Cell Antibody (platelet-endothelial cell adhesion molecule 1): A Strategy for Vascular Immunotargeting of Drugs," *Proc. Natl. Acad. Sci.*, 96: pp. 2379-2384 (1999).

Schnitzer, J. E., "Update on the Cellular and Molecular Basis of Capillary Permeability," *TCM*, 3(4): 124-130(1993).

Essler, M. et al., "Molecular Specialization of Breast Vasculature: A Breast-Homing Phage-Displayed Peptide Binds to Aminopeptidase P in Breast Vasculature," *Proc. Natl. Acad. Sci.*, 99: pp. 2252-2257 (2002).

Ruoslahti, E., "Drug Targeting to Specific Vascular Sites," *Drug Discovery Today*, 7: 1138-1143 (2002).

Durr, E., et al., "Direct Proteomic Mapping of the Lung Microvascular Endothelial Cell Surface in Vivo and In Cell Culture," *Nature Biotechnology*, 22: 985-992 (2004).

Christian, S., et al., "Nucleolin Expressed at the Cell Surface is a Marker of Endothelial Cells in Angiogenic Blood Vessels," *Journal of Cell Biology*, 163:871-878 (2003).

Van Hensbergen, Y., et al., "A Doxorubicin-CNGRC-Peptide Conjugate with Prodrug Properties," *Biochemical Pharmacology*, 63:897-908 (2002).

Pastorino, F., et al., "Vascular Damage and Anti-Angiogenic Effects of Tumor Vessel-Targeted Liposomal Chemotherapy," *Cancer Research*, 63:7400-7409 (2003).

Lasch, J., et al., "Aminopeptidase P-Cell-Surface Antigen of Endothelial and Lymphoid Cells: Catalytic and Immuno-Histopcal Evidences," *Biological Chemistry*, 379: 705-709 (Jun. 1998).

Henniker, A.J., et al., "A Novel Non-Lineage Antigen on Human Leukocytes: Characterization with Two CD-48 Monoclonal Antibodies," *Disease Markers*, 8(4): 179-190 (May 1990).

Office Action dated Aug. 19, 2008 for EP Application No. 05804874. 5.

NCBI "Gene" Information for CD48, http://www.ncbi.nlm.nih.gov/gene/962#summary, (accessed 2013).

\* cited by examiner

SEQUENCE LISTING

<160> NUMBER OF SEQ ID NOS: 2

<210> SEQ ID NO 1
<211> LENGTH: 18
<212> TYPE: PRT
<213> ORGANISM: Rat

<400> SEQUENCE: 1

Cys Gly Tyr Thr Ala Arg Asp Tyr Tyr His Asp Leu Asp Pro Glu Glu
 1               5                  10                  15

Ala Arg

<210> SEQ ID NO 2
<211> LENGTH: 19
<212> TYPE: PRT
<213> ORGANISM: Rat

<400> SEQUENCE: 2

Cys Gln Leu Leu Gln Ser Gln Ala Gln Gln Ser Gly Ala Gln Gln Thr
 1               5                  10                  15

Lys Lys Asp

TISSUE-SPECIFIC IMAGING AND THERAPEUTIC AGENTS TARGETING PROTEINS EXPRESSED ON LUNG ENDOTHELIAL CELL SURFACE

RELATED APPLICATION

This application claims the benefit of U.S. Provisional Application No. 60/576,114, filed Jun. 2, 2004. The entire teachings of the above application are incorporated herein by reference.

GOVERNMENT SUPPORT

The invention was supported, in whole or in part, by grants HL58216, HL52766, CA95893, CA83989 and CA97528 from the National Institutes of Health. The Government has certain rights in the invention.

BACKGROUND OF THE INVENTION

New targets are needed for detecting disease through molecular imaging (Massoud, T. F. & Gambhir, S. S., Genes Dev 17, 545-80 (2003); Herschman, H. R., Science 302, 605-8 (2003); Rudin, M. & Weissleder, R., Nat Rev Drug Discov 2, 123-31 (2003); Weissleder, R. Nat Rev Cancer 2, 11-8 (2002)) and for treating disease through directed delivery in vivo (Drews, J., Science 287, 1960-4 (2000); Lindsay, M. A., Nat Rev Drug Discov 2, 831-8 (2003); Workman, P., Curr Cancer Drug Targets 1, 33-47 (2001); Anzick, S. L. & Trent, J. M. Oncology (Huntingt) 16, 7-13 (2002); Cavenee, W. K., Carcinogenesis 23, 683-6 (2002)). Genome completion identifies a target pool of 40,000 genes which may translate into a million possible protein targets (Huber, L. A., Nat Rev Mol Cell Biol 4, 74-80 (2003)). Genomic and proteomic analysis of normal and diseased tissues have yielded thousands of genes and gene products for diagnostic and tissue assignment as well as potential therapeutic targeting (Drews, J., Science 287, 1960-4 (2000); Lindsay, M. A., Nat Rev Drug Discov 2, 831-8 (2003); Workman, P., Curr Cancer Drug Targets 1, 33-47 (2001); Anzick, S. L. & Trent, J. M., Oncology (Huntingt) 16, 7-13 (2002); Huber, L. A., Nat Rev Mol Cell Biol 4, 74-80 (2003); Perou, C. M. et al., Nature 406, 747-52 (2000)). Yet the sheer number of candidates can overwhelm the required in vivo validation process, leading some to question the ultimate impact of these approaches on speeding up drug discovery (Drews, J., Science 287, 1960-4 (2000); Lindsay, M. A., Nat Rev Drug Discov 2, 831-8 (2003); Workman, P., Curr Cancer Drug Targets 1, 33-47 (2001); Huber, L. A., Nat Rev Mol Cell Biol 4, 74-80 (2003)). Reducing tissue data complexity to a manageable subset of candidates most relevant to targeting, imaging, and treating disease is clearly desired but requires new discovery and validation strategies that effectively focus the power of global identification technologies.

Selectively targeting a single organ or diseased tissue such as solid tumors in vivo remains a desirable yet elusive goal of molecular medicine that could enable more effective imaging as well as drug and gene therapies for many acquired and genetic diseases (Massoud, T. F. & Gambhir, S. S. Genes Dev 17, 545-80 (2003); Herschman, H. R., Science 302, 605-8 (2003); Weissleder, R., Nat Rev Cancer 2, 11-8 (2002); Lindsay, M. A., Nat Rev Drug Discov 2, 831-8 (2003); Huber, L. A., Nat Rev Mol Cell Biol 4, 74-80 (2003)). Most tissue- and disease-associated proteins are expressed by cells inside tissue compartments not readily accessible to intravenously injected biological agents such as antibodies. This inaccessibility hinders many site-directed therapies (Drews, J., Science 287, 1960-4 (2000); Lindsay, M. A., Nat Rev Drug Discov 2, 831-8 (2003); Workman, P., Curr Cancer Drug Targets 1, 33-47 (2001); Jain, R. K., Nat. Med. 4, 655-7 (1998); Dvorak, H. F., et al., Cancer Cells 3, 77-85 (1991)) and imaging agents (Massoud, T. F. & Gambhir, S. S., Genes Dev 17, 545-80 (2003); Herschman, H. R., Science 302, 605-8 (2003); Rudin, M. & Weissleder, R., Nat Rev Drug Discov 2, 123-31 (2003); Weissleder, R. Nat Rev Cancer 2, 11-8 (2002)). For example, multiple barriers to solid tumor delivery prevent effective immunotherapy in vivo, despite efficacy and specificity in vitro (Jain, R. K., Nat. Med. 4, 655-7 (1998); Dvorak, H. F., et al., Cancer Cells 3, 77-85 (1991); von Mehren, M., et al., Annu Rev Med 54, 343-69 (2003); Farah, R. A., et al., Crit Rev Eukaryot Gene Expr 8, 321-56 (1998); Carver, L. A. & Schnitzer, J. E., Nat Rev Cancer 3, 571-81 (2003); Schnitzer, J. E., N Engl J Med 339, 472-4 (1998)). Conversely, the universal access of chemotherapeutics dilutes efficacy to require increased dosages leading to unwanted systemic side effects. Thus, new approaches are required that cut through the cumbersome overabundance of molecular information to permit rapid discovery and validation of accessible tissue-specific targets that can direct molecular imaging and pharmacodelivery in vivo.

Vascular endothelial cells form a barrier in vivo that can greatly limit the ability of many drugs, gene vectors, and imaging agents circulating in the blood to reach their intended target cells residing within a single tissue. This restricted accessibility can prevent therapeutic efficacy in vivo and increase therapeutic side effects. Vascular targeting is a new drug and gene delivery strategy that targets the luminal endothelial cell surface and its caveolae which are directly exposed and thus inherently accessible to agents circulating in the blood (McIntosh, D. P., et al., Proc Natl Acad Sci USA 99, 1996-2001 (2002); Carver, L. A. & Schnitzer, J. E., Nat Rev Cancer 3, 571-581 (2003)). Agents such as peptides and antibodies to endothelial cell surface proteins show promise for directing tissue-specific pharmacodelivery to the vasculature in vivo (McIntosh, D. P., et al., Proc Natl Acad Sci USA 99, 1996-2001 (2002); Pasqualini, R. & Ruoslahti, E., Nature 380, 364-366 (1996); Muzykantov, V. R., et al., Immunotargeting of antioxidant enzyme to the pulmonary endothelium. Proc Natl Acad Sci USA 93, 5213-5218 (1996); Muzykantov, V. R. et al., Proc Natl Acad Sci USA 96, 2379-2384. (1999)) but greater molecular information and more candidate targets expressed in vivo are needed to understand and define the potential of vascular targeting.

The endothelium exists as an attenuated cell monolayer lining all blood vessels, and forming a physiologically vital interface between the circulating blood and the underlying cells inside the tissue. It plays a significant role controlling the passage of blood molecules and cells into the tissue and in many other normal physiological functions including vasoregulation, coagulation, and inflammation as well as tissue nutrition, growth, survival, repair and overall organ homeostasis and function (Schnitzer, J. E., Trends in Cardiovasc. Med. 3, 124-130 (1993)). Disruption of the vascular endothelium and its normal barrier function can lead rapidly to tissue edema, hypoxia, pathology, and even organ death (Fajardo, L. F., Am. J. Clin. Pathol. 92, 241-250 (1989); Jaffe, E. A., Cell biology of endothelial cells. Hum. Pathol. 18, 234-239 (1987)).

Although the microenvironment of the tissue surrounding the blood vessels appears clearly to influence greatly the phenotype of the endothelial cells (Madri, J. A. & Williams, S. K., J. Cell Biol. 97, 153-165 (1983); Goerdt, S. et al., Exp Cell Biol 57, 185-192 (1989); Gumkowski, F. et al., Blood}

Vessels 24, 11-23 (1987); Hagemeier, H. H., et al., Int J Cancer 38, 481-488. (1986); Aird, W. C. et al., J Cell Biol 138, 1117-1124 (1997); Janzer, R. C. & Raff, M. C. Nature 325, 253-257 (1987); Stewart, P. A. & Wiley, M. J., Develop Biol 84, 183-192 (1981)), currently there is very little molecular information about vascular endothelium as it exists natively in the tissue. This is in large part because of technical limitations in performing large-scale molecular profiling on a cell-type that comprises such a small percentage of the total cells in the tissue. Past approaches have relied primarily on genomic or antibody-based analysis of endothelial cells isolated from the tissue by enzymatic digestion to disassemble the tissue and release single cells for sorting using endothelial cell markers (Auerbach, R., et al., Microvasc Resn 29, 401-411 (1985); St Croix, B. et al., Science 289, 1197-1202 (2000); Plendl, J., et al., Anat Histol Embryol 21, 256-262 (1992)). Over the last three decades, the study of isolated and even cultured endothelial cells has yielded much functional and molecular information; however, both the significant perturbation of the tissue and the growth in culture contribute to morphologically obvious phenotypic drift that can translate rapidly into loss of native function and protein expression (Madri, J. A. & Williams, S. K., J. Cell Biol. 97, 153-165 (1983); Schnitzer, J. E. in Capillary Permeation, Cellular Transport and Reaction Kinetics. (ed. J. H. Linehan) 31-69 (Oxford Press, London; 1997). The reported ability of specific cells and select peptides displayed on bacteriophage to home to specific tissues of the body after intravenous injection also provides indirect evidence supporting the molecular heterogeneity of endothelial cell surface in different organ (Pasqualini, R. & Ruoslahti, E., Nature 380, 364-366 (1996); Plendl, J., et al., Anat Histol Embryol 21, 256-262 (1992); Rajotte, D. et al., J Clin Invest 102, 430-437 (1998)) but have not yet facilitated mapping of endothelial cell surface proteins in vivo. The degree to which endothelial cell expression is modulated within different normal and diseased tissues remains unclear.

SUMMARY OF THE INVENTION

The present invention pertains to methods of delivering an agent to, into and/or across vascular endothelium in a tissue-specific manner. In the methods of the invention, the agent is delivered by contacting the luminal surface of vasculature, or caveolae of vasculature, with an agent that specifically binds to a targeted protein expressed on endothelial cell surface. In certain preferred embodiments, the targeted protein is TIE-2, APN, TEM4, TEM6, ICAM-1, or nucleolin. In other preferred embodiments, the targeted protein is P2Z receptor or Trk-A. In another preferred embodiment, the targeted protein is FLJ10849 or HSPA12B. In a particular embodiment, the targeted protein is APP or OX-45, and the targeted tissue is lung tissue. In a further preferred embodiment, the targeted protein is a protein set forth in Table 1.

In certain embodiments of the invention, the methods can be used for treating pathologies in an individual, by administering to the individual therapeutic targeting agent that binds to a targeted protein expressed on endothelial cell surface. The therapeutic targeting agent can be an antibody to the targeted protein expressed on endothelial cell surface; alternatively, the therapeutic targeting agent can be a binding agent of a targeted protein expressed on endothelial cell surface. In addition, the therapeutic targeting agent can also be an agent having an active agent component and a targeting agent component, in which the targeting agent component is: an agent that specifically binds to a targeted protein expressed on endothelial cell surface (e.g., an antibody to the targeted protein expressed on endothelial cell surface); or a specific binding partner of the targeted protein expressed on endothelial cell surface. In these embodiments, the active agent component can be, for example, a radionuclide; a chemotherapeutic agent; an immune stimulatory agent; an anti-neoplastic agent: an anti-inflammatory agent; a pro-inflammatory agent; a pro-apoptotic agent; a pro-coagulant; a toxin; an antibiotic; a hormone; an enzyme; a protein (e.g., a recombinant protein or a recombinant modified protein) a carrier protein (e.g., albumin, modified albumin); a lytic agent; a small molecule; aptamers; cells, including modified cells; vaccine-induced or other immune cells; nanoparticles (e.g., albumin-based nanoparticles); transferring; immunoglobulins; multivalent antibodies; lipids; lipoproteins; liposomes; an altered natural ligand; a gene or nucleic acid; RNA or siRNA; a viral or non-viral gene delivery vector; a prodrug; or a promolecule. The invention additionally pertains to physiological compositions incorporating a therapeutic targeting agent.

The invention also pertains to methods of assessing response to treatment with a therapeutic targeting agent, by assessing the level of the targeted protein expressed on endothelial cell surface, in a sample from the individual before treatment with the therapeutic targeting agent, and during or after treatment with the therapeutic targeting agent, and comparing the levels; a level of the targeted protein during or after treatment that is significantly lower than the level of the targeted protein before treatment, is indicative of efficacy of treatment with the therapeutic targeting agent.

The invention further pertains to methods for performing physical imaging of an individual, using an imaging agent that includes a targeting agent component (as described above) and an imaging agent component. The imaging agent component can be, for example, a radioactive agent, radioisotope or radiopharmaceutical; a contrast agent; a magnetic agent or a paramagnetic agent; liposomes; ultrasound agents; a nanoparticle; a gene vector or virus inducing a detecting agent; an enzyme; a prosthetic group; a fluorescent material; a luminescent material; or a bioluminescent material. Upon administration, the targeted imaging agents can be visualized noninvasively by conventional external detection means (designed for the imaging agent), to detect the preferential or specific accumulation. In addition, the invention pertains to methods of delivering such imaging agents in vivo in a tissue-specific manner, and then assessing a tissue (e.g., biopsy) sample for the presence of the imaging agent; the methods also pertain to delivering imaging agents in a tissue-specific manner to a tissue sample. The methods additionally pertain to methods assessing an individual for the presence or absence of a pathology, administering to the individual an agent of interest that comprises an imaging agent component and a targeting agent component, as described above, and assessing the individual for the presence or absence of a concentration of the agent of interest, wherein the presence of a concentration of the agent of interest is indicative of the presence of the pathology.

The methods of the invention provide an easy method that permits delivery to, penetration into, imaging of and treatment of certain tissues or groups of tissues in vivo and in vitro.

DETAILED DESCRIPTION OF THE INVENTION

A description of preferred embodiments of the invention follows.

An analytical paradigm was used that reduced the complexity of normal and diseased tissue to focus on a small subset of proteins induced at the blood-tissue interface. Subcellular tissue fractionation, subtractive proteomics, in silico bioinformatics, expression profiling, and molecular imaging were integrated to map tissue-modulation of luminal endothelial cell surface protein expression in vivo and to discover and rapidly validate intravenous-accessible targets permitting specific immunotargeting of lungs in vivo.

The technical advancement of the method of analysis has allowed the first large-scale mapping of the proteome of the cell surface of microvascular endothelium as it exists in lung tissue as well as it exists when cells isolated and grown in cell culture. The protein expression profile of endothelial cell monolayers was compared in vivo and in vitro and considerable evidence was found for tissue-modulated expression of protein not sustained under standard cell culture conditions. Comparative cell surface mapping of normal lung endothelium in vivo and in vitro has significantly advanced understanding of the extent to which the tissue micro-environment can modulate endothelial cell function and protein expression not only in normal tissues but also in diseases, such as cancer.

The analytical paradigm confirmed the expression of several proteins on endothelial cells, including proteins that were newly found to be expressed on the endothelial cell surface. Certain proteins were detected most strongly in lung, and others were detected in lung and at comparable levels in at least one other organ. In addition, it was found that certain proteins whose expression has been reported previously as not normally present in endothelial cells except during angiogenesis and/or inflammation, were, in fact present in endothelial cells.

As a result of these discoveries, methods are now available to deliver agents to, into and/or across vascular endothelium in a tissue-specific manner, using an agent that specifically binds to a targeted protein. In certain embodiments of the invention, the methods deliver a therapeutic agent to, into and/or across of vascular endothelium in a tissue-specific manner. These methods can be used to treat diseases (e.g., neoplasms) in an individual. In other embodiments of the invention, the methods deliver an imaging agent to, into and/or across vascular endothelium in a tissue-specific manner. Also available are in vitro diagnostics, utilizing an agent that specifically binds to a targeted protein, as well as methods to assess treatment efficacy as well as to assess prognosis of disease. Screening methods to identify agents altering activity of targeted proteins are also described, as are antibodies to targeted proteins, which can be used in the methods of the invention. In addition, the agents described herein can be used for the manufacture of medicaments, for example, for treatment, imaging, or other methods described herein.

Vascular Endothelium and Tissue Accessibility

Plasmalemmal vesicles called caveolae are abundant on the endothelial cell surface, function in selective endocytosis and transcytosis of nutrients, and provide a means to enter endothelial cells (endocytosis) and/or to penetrate the endothelial cell barrier (transcytosis) for delivery to underlying tissue cells. Focus is now on the vascular endothelial cell surface in contact with the circulating blood, to bypass the problem of poor penetrability into tissues and tumors; this vascular endothelial cell surface provides an inherently accessible, and thus targetable, surface.

Past work has mapped and characterized extensively the molecular architecture and function of the cell surface and especially its caveolae in normal vascular endothelium, primarily in rat lung tissue (Schnitzer, J. E. and Oh, P. (1994) J Biol Chem 269, 6072-82; Schnitzer, J. E., et al., (1994) J Cell Biol 127, 1217-32; Schnitzer, J. E., et al., (1995) Science 269, 1435-9; Schnitzer, J. E., et al., (1996) [publisher's erratum appears in Science 1996 Nov. 15; 274(5290):1069]. Science 274, 239-42; Schnitzer, J. E., et al., (1995). J Biol Chem 270, 14399-404; Schnitzer, J. E., et al., (1995) Am J Physiol 268, H48-55; McIntosh, D. P. and Schnitzer, J. E. (1999) Am J Physiol 277, H2222-32).

Targeting endothelial caveolae via antibodies or other agents that specifically bind to proteins expressed on the cell surface of vascular endothelium, permits specific delivery to, penetration into, and imaging of tissues. As used herein, the term "targeted protein" refers to a protein, such as one of the proteins identified in the Examples, that is expressed on the endothelial cell surface. The targeted proteins described herein can be grouped into various categories, including:

proteins that are predominantly expressed on the endothelial cell surface of one or of a select few types of tissues (e.g., APP, OX-45);

proteins which were previously identified as being expressed during angiogenesis and/or inflammation and are newly identified as being expressed in normal endothelial tissues (e.g., Tie-2, TEM4, TEM6, APN, ICAM-1, and nucleolin);

proteins which were previously identified as being expressed by other cells or in other tissues and are newly identified as being expressed by endothelial cells in one or more organs (e.g., P2Z, Trk-A, NA-H exchanger 3 regulatory factor 2);

protein products of nucleic acids or genes previously unidentified (e.g., HSPA12B, or septin homolog FLJ10849);

proteins set forth in Table 1.

A protein that is expressed to "a greater degree" in one tissue than in another tissue is a protein that is expressed in an amount that is greater, by a degree that is significant (e.g., equal to or greater than 2-fold, preferably equal to or greater than 3-fold, even more preferably equal to or greater than 5-fold, still more preferably equal to or greater than 10-fold, even more preferably equal to or greater than 20-fold) than the expression of that protein in another tissue. The selection of which type of targeted protein for use in the invention will depend on the desired targeting methods. When the degree of expression is greater by a higher degree (e.g., equal to or greater than 10-fold, equal to or greater than 20-fold, or even equal to or greater than 100-fold), the expression may become functionally equivalent to expression solely in the lug tissue: directed and effective delivery of agents (e.g., therapeutic agents or imaging agents as described herein) to the a desired tissue occurs, with minimal or no delivery to other tissues. Thus, the amount that is functionally equivalent to expression solely in the desired tissue can be determined by assessing whether the goal of effective delivery of agents is met with minimal or no delivery to other tissues.

Delivery of Agents

In the methods of the invention, an agent is delivered in a tissue-specific manner, utilizing an agent that specifically binds to a protein expressed on endothelial cell surface. An agent that "specifically binds" to a targeted protein, as the term is used herein, is an agent that preferentially or selectively binds to that targeted protein. While certain degree of non-specific interaction may occur between the agent that specifically binds and the targeted protein, nevertheless, specific binding, may be distinguished as mediated through specific recognition of the targeted protein, in whole or part. Typically specific binding results in a much stronger association between the agent and the targeted protein than between the agent and other proteins, e.g., other vascular proteins. The affinity constant (Ka, as opposed to Kd) of the agent for its cognate is at least $10^6$ or $10^7$, usually at least $10^8$, alternatively at least $10^9$, alternatively at least $10^{10}$, or alternatively at least $10^{11}$ M. It should be noted, also, that "specific" binding may be binding that is sufficiently site-specific to effectively be "specific": for example, when the degree of binding is greater by a higher degree (e.g., equal to or greater than 10-fold, equal to or greater than 20-fold, or even equal to or greater than 100-fold), the binding may become functionally equivalent to binding solely to the targeted protein at a particular location: directed and effective binding occurs with minimal or no delivery to other tissues. Thus, the amount that is functionally equivalent to specific binding can be determined by assessing whether the goal of effective delivery of agents is met with minimal or no binding to other tissues.

The targeted protein is tissue-specific: in certain embodiments, the targeted protein may be present only in one tissue, resulting in tissue-specific interaction between the agent that binds to the targeted protein and the targeted protein itself. In addition, the targeted protein may be present in all segments of the vasculature within any organ (e.g., aorta, arteries, small arteries, arterioles, capillaries, venules, small veins, veins, vena cava) or may be present in any single segment or subset of segments in the vasculature. As used herein, a targeted protein that is present in one or more type of tissue or organ, is present in at least one of the segments of the vasculature within that tissue or organ, and may be present in more than one, or all, of the segments of the vasculature within that tissue or organ. In other embodiments, the targeted protein may be present in more than one type of tissue, yet still results in tissue-specific interaction between the agent that binds to the targeted protein and the targeted protein itself. Thus, the term "tissue-specific" indicates that the agent preferentially or selectively binds to a particular type of tissue (e.g., lung, vasculature, vasculature of lung) or to a specific set of tissues (e.g., lung and liver, vasculature of lung and liver, lung and kidney, vasculature of lung and kidney). In representative embodiments, the targeted protein is TIE-2, APN, TEM4, TEM6, ICAM-1, nucleolin, P2Z receptor, Trk-A, FLJ10849, HSPA12B, APP, or OX-45; alternatively, targeted protein is a protein set forth in Table 1.

In a particular embodiment, the agent that specifically binds the targeted protein is or comprises an antibody or fragment of an antibody (e.g., Fab' fragments). Representative antibodies include commercially available antibodies (as listed in Linscott's Directory). Alternatively, the agent is or comprises another agent that specifically binds to a targeted protein (a "specific binding partner"). Representative specific binding partners include natural ligands, peptides, small molecules (e.g., inorganic small molecules, organic small molecules, derivatives of small molecules, composite small molecules); nanoparticles (e.g., lipid or non-lipid based formulations); lipids; lipoproteins; lipopeptides; lipid derivatives; liposomes; modified endogenous blood proteins used to carry chermotherapeutics.

The agent can also comprise a first component that binds to the targeted protein, as described above, and a second component, that is an active component (e.g., a therapeutic agent or imaging agent, as described in detail below). The agent can be administered by itself, or in a composition (e.g., a pharmaceutical or physiological composition) comprising the agent. It can be administered either in vivo (e.g., to an individual) or in vitro (e.g., to a tissue sample). The methods of the invention can be used not only for human individuals, but also are applicable for veterinary uses (e.g., for other mammals, including domesticated animals (e.g., horses, cattle, sheep, goats, pigs, dogs, cats) and non-domesticated animals.

The agent can be administered by itself, or in a composition (e.g., a physiological or pharmaceutical composition) comprising the agent. For example, the therapeutic targeting agent can be formulated together with a physiologically acceptable carrier or excipient to prepare a pharmaceutical composition. The carrier and composition can be sterile. The formulation should suit the mode of administration.

Suitable pharmaceutically acceptable carriers include but are not limited to water, salt solutions (e.g., NaCl), saline, buffered saline, alcohols, glycerol, ethanol, gum arabic, vegetable oils, benzyl alcohols, polyethylene glycols, gelatin, carbohydrates such as lactose, amylose or starch, dextrose, magnesium stearate, talc, silicic acid, viscous paraffin, perfume oil, fatty acid esters, hydroxymethylcellulose, polyvinyl pyrolidone, etc., as well as combinations thereof. The pharmaceutical preparations can, if desired, be mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active agents.

The composition, if desired, can also contain minor amounts of wetting or emulsifying agents, or pH buffering agents. The composition can be a liquid solution, suspension, emulsion, tablet, pill, capsule, sustained release formulation, or powder. The composition can be formulated as a suppository, with traditional binders and carriers such as triglycerides. Oral formulation can include standard carriers such as pharmaceutical grades of mannitol, lactose, starch, magnesium stearate, polyvinyl pyrollidone, sodium saccharine, cellulose, magnesium carbonate, etc.

Methods of introduction of these compositions include, but are not limited to, intradermal, intramuscular, intraperitoneal, intraocular, intravenous, subcutaneous, topical, oral and intranasal. Other suitable methods of introduction can also include rechargeable or biodegradable devices, particle acceleration devises ("gene guns") and slow release polymeric devices. If desired, the compositions can be administered into a specific tissue, or into a blood vessel serving a specific tissue (e.g., the carotid artery to target brain). The pharmaceutical compositions can also be administered as part of a combinatorial therapy with other agents, either concurrently or in proximity (e.g., separated by hours, days, weeks, months). The activity of the compositions may be potentiated by other agents administered concurrently or in proximity.

The composition can be formulated in accordance with the routine procedures as a pharmaceutical composition adapted for administration to human beings or animals. For example, compositions for intravenous administration typically are solutions in sterile isotonic aqueous buffer. Where necessary, the composition may also include a solubilizing agent and a local anesthetic to ease pain at the site of the injection. Generally, the ingredients are supplied either separately or mixed together in unit dosage form, for example, as a dry lyophilized powder or water free concentrate in a hermetically sealed container such as an ampule or sachette indicating the quantity of active agent. Where the composition is to be administered by infusion, it can be dispensed with an infusion bottle containing sterile pharmaceutical grade water, saline or dextrose/water. Where the composition is administered by injection, an ampule of sterile water for injection or saline can be provided so that the ingredients may be mixed prior to administration.

For topical application, nonsprayable forms, viscous to semi-solid or solid forms comprising a carrier compatible with topical application and having a dynamic viscosity preferably greater than water, can be employed. Suitable formulations include but are not limited to solutions, suspensions, emulsions, creams, ointments, powders, enemas, lotions, sols, liniments, salves, aerosols, etc., which are, if desired, sterilized or mixed with auxiliary agents, e.g., preservatives, stabilizers, wetting agents, buffers or salts for influencing osmotic pressure, etc. The agent may be incorporated into a cosmetic formulation. For topical application, also suitable are sprayable aerosol preparations wherein the active ingredient, preferably in combination with a solid or liquid inert carrier material, is packaged in a squeeze bottle or in admixture with a pressurized volatile, normally gaseous propellant, e.g., pressurized air.

Agents described herein can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

Representative methods incorporating delivery of an agent in a tissue-specific manner are described below in relation to treatment, imaging, and diagnostics.

Tissue Targeting and Therapy

In one embodiment of the invention, methods are available for targeting a therapeutic agent to a particular tissue, for delivery of an agent of interest (e.g., for treatment of a pathology). The term, "treatment" as used herein, can refer to ameliorating symptoms associated with the pathology; and/or to lessening the severity, duration or frequency of symptoms of the pathology. A "pathology," as used herein, refers to a structural or functional deviation from normal, that is indicative of a disease process. For example, representative lung pathologies include asthma, emphysema, tuberculosis, pneumonia, COPH, pulmonary hypertension, cystic fibrosis, and other acquired or genetic lung-related conditions. Other pathologies include benign and malignant neoplasms that share tissue-specific targeting proteins with a hosting organ (e.g., mammary adenocarcinom in breast tissue or as metastatic lesions in brain, that maintain endothelial cell protein targets expressed normally in breast but not brain).

In the methods, a therapeutic targeting agent is used. A "therapeutic targeting agent," as used herein, refers to an agent that targets the pathology, for destruction of the pathological cells or tissues, and/or for correction of the pathology, and/or for reducing or eliminating the effects of the pathology.

In one embodiment, the therapeutic targeting agent is or comprises an antibody that specifically binds a targeted protein, as described herein (e.g., TIE-2, APN, TEM4, TEM6, ICAM-1, nucleolin, P2Z receptor, Trk-A, FLJ10849, HSPA12B, APP, OX-45); alternatively, the therapeutic targeting agent is or comprises an antibody that specifically binds a protein set forth in Table 1. An "antibody" is an immunoglobulin molecule obtained by in vitro or in vivo generation of the humoral response, and includes both polyclonal and monoclonal antibodies. The term also includes genetically engineered forms such as chimeric antibodies (e.g., humanized murine antibodies), heteroconjugate antibodies (e.g., bispecific antibodies), and recombinant single chain Fv fragments (scFv). The term "antibody" also includes antigen binding fragments of antibodies, such as Fab', F(ab')2, Fab, Fv, rIgG, and, inverted IgG, as well as the variable heavy and variable light chain domains. An antibody immunologically reactive with a targeted protein can be generated in vivo or by recombinant methods such as selection of libraries of recombinant antibodies in phage or similar vectors. See, e.g., Huse et al. (1989) Science 246:1275-1281; and Ward, et al. (1989) Nature 341:544-546; and Vaughan et al. (1996) Nature Biotechnology, 14:309-314. An "antigen binding fragment" includes any portion of an antibody that binds to the targeted protein. An antigen binding fragment may be, for example, a polypeptide including a CDR region, or other fragment of an immunoglobulin molecule which retains the affinity and specificity for the targeted protein.

In another embodiment, the therapeutic targeting agent is or comprises another agent that specifically binds to the targeted protein. Representative agents that specifically bind to a targeted protein include antibodies as described above, and other specific binding partners as described above.

In yet another embodiment, the therapeutic targeting agent comprises an active agent component and a targeting agent component. The targeting agent component is or comprises an agent that specifically binds to a targeted protein, as described above. As described above, in certain embodiments, the targeted protein may be present only in one tissue, resulting in tissue-specific interaction between the agent that binds to the targeted protein and the targeted protein itself. In other embodiments, the targeted protein may be present in more than one type of tissue, yet still results in tissue-specific interaction between the agent that binds to the targeted protein and the targeted protein itself. In preferred embodiments of the invention, the targeting agent component specifically binds to a targeted protein such as APP or OX-45, for targeting of lung tissue.

The targeting agent component is linked to the active agent component. For example, they can be covalently bonded directly to one another. Where the two are directly bonded to one another by a covalent bond, the bond may be formed by forming a suitable covalent linkage through an active group on each moiety. For instance, an acid group on one compound may be condensed with an amine, an acid or an alcohol on the other to form the corresponding amide, anhydride or ester, respectively. In addition to carboxylic acid groups, amine groups, and hydroxyl groups, other suitable active groups for forming linkages between a targeting agent component and an active agent component include sulfonyl groups, sulfhydryl groups, and the haloic acid and acid anhydride derivatives of carboxylic acids.

In other embodiments, the targeting agent component and an active agent component may be covalently linked to one another through an intermediate linker. The linker advantageously possesses two active groups, one of which is complementary to an active group on the targeting agent component, and the other of which is complementary to an active group on the active agent component. For example, where the both possess free hydroxyl groups, the linker may suitably be a diacid, which will react with both compounds to form a diether linkage between the two residues. In addition to carboxylic acid groups, amine groups, and hydroxyl groups, other suitable active groups for forming linkages between pharmaceutically active moieties include sulfonyl groups, sulfhydryl groups, and the haloic acid and acid anhydride derivatives of carboxylic acids.

Suitable linkers are set forth in the table below.

| FIRST ACTIVE GROUP | SECOND ACTIVE GROUP | SUITABLE LINKER |
| --- | --- | --- |
| Amine | Amine | Diacid |
| Amine | Hydroxy | Diacid |
| Hydroxy | Amine | Diacid |
| Hydroxy | Hydroxy | Diacid |
| Acid | Acid | Diamine |
| Acid | Hydroxy | Amino acid, hydroxyalkyl acid, sulfhydrylalkyl acid |
| Acid | Amine | Amino acid, hydroxyalkyl acid, sulfhydrylalkyl acid |

Suitable diacid linkers include oxalic, malonic, succinic, glutaric, adipic, pimelic, suberic, azelaic, sebacic, maleic, fumaric, tartaric, phthalic, isophthalic, and terephthalic acids.

While diacids are named, the skilled artisan will recognize that in certain circumstances the corresponding acid halides or acid anhydrides (either unilateral or bilateral) are preferred as linker reprodrugs. A preferred anhydride is succinic anhydride. Another preferred anhydride is maleic anhydride. Other anhydrides and/or acid halides may be employed by the skilled artisan to good effect.

Suitable amino acids include -butyric acid, 2-aminoacetic acid, 3-aminopropanoic acid, 4-aminobutanoic acid, 5-aminopentanoic acid, 6-aminohexanoic acid, alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, and valine. Again, the acid group of the suitable amino acids may be converted to the anhydride or acid halide form prior to their use as linker groups.

Suitable diamines include 1,2-diaminoethane, 1,3-diaminopropane, 1,4-diaminobutane, 1,5-diaminopentane, 1,6-diaminohexane. Suitable aminoalcohols include 2-hydroxy-1-aminoethane, 3-hydroxy-1-aminoethane, 4-hydroxy-1-aminobutane, 5-hydroxy-1-aminopentane, 6-hydroxy-1-aminohexane. Suitable hydroxyalkyl acids include 2-hydroxyacetic acid, 3-hydroxypropanoic acid, 4-hydroxybutanoic acid, 5-hydroxypentanoic acid, 5-hydroxyhexanoic acid. The person having skill in the art will recognize that by selecting the components of the targeting agent component and active agent component having suitable active groups, and by matching them to suitable linkers, a broad palette of inventive compounds may be prepared within the scope of the present invention.

Moroever, the various linker groups can be designated either "weak" or "strong" based on the stability of the covalent bond which the linker functional group will form between the spacer and either the polar lipid carrier or the biologically active compound. The weak functionalities include, but are not limited to phosphoramide, phosphoester, carbonate, amide, carboxyl-phosphoryl anhydride, ester and thioester. The strong functionalities include, but are not limited to ether, thioether, amine, sterically hindered amides and esters. The use of a strong linker functional group between the spacer group and the biologically-active compound will tend to decrease the rate at which the compound will be released at the target site, whereas the use of a weak linker functional group between the spacer group and the compound may act to facilitate release of the compound at the target site.

Enzymatic release is also possible, but such enzyme-mediated modes of release will not necessarily be correlated with bond strength in such embodiments of the invention. Spacer moieties comprising enzyme active site recognition groups, such as spacer groups comprising peptides having proteolytic cleavage sites therein, are envisioned as being within the scope of the present invention. In certain embodiments, the linker moiety includes a spacer molecule which facilitated hydrolytic or enzymatic release of the active agent component from the targeting agent component. In particularly preferred embodiments, the spacer functional group is hydrolyzed by an enzymatic activity found in the target vascular tissue, preferably an esterase.

The active agent component, which is linked to the targeting agent component, can be or comprise any agent that achieves the desired therapeutic result, including agents such as: a radionuclide (e.g., I125, 123, 124, 131 or other radioactive agent); a chemotherapeutic agent (e.g., an antibiotic, antiviral or antifungal); an immune stimulatory agent (e.g., a cytokine); an anti-neoplastic agent: an anti-inflammatory agent; a pro-inflammatory agent; a pro-apoptotic agent (e.g., peptides or other agents to attract immune cells and/or stimulate the immune system); a pro-coagulant; a toxin (e.g., ricin, enterotoxin, LPS); an antibiotic; a hormone; a protein (e.g., a recombinant protein or a recombinant modified protein); a carrier protein (e.g., albumin, modified albumin); an enzyme; another protein (e.g., a surfactant protein, a clotting protein); a lytic agent; a small molecule (e.g., inorganic small molecules, organic small molecules, derivatives of small molecules, composite small molecules); aptamers; cells, including modified cells; vaccine-induced or other immune cells; nanoparticles (e.g, lipid or non-lipid based formulations, albumin-based formulations); transferrins; immunoglobulins; multivalent antibodies; lipids; lipoproteins; lipopeptides; liposomes; lipid derivatives; an natural ligand; and altered protein (e.g., albumin or other blood carrier protein-based delivery system, modified to increase affinity for the targeted protein; orosomucoid); an agent that alters the extracellular matrix of the targeted cell; an agents that inhibits growth, migration or formation of vascular structures (for a therapeutic targeting agent); an agent that enhances or increases growth, migration or formation of vascular structures (for an neovasculature targeting agent); a gene or nucleic acid (e.g., an antisense oligonucleotide RNA; siRNA); viral or non-viral gene delivery vectors or systems; or a prodrug or promolecule.

For example, in a particular embodiment, antisense oligonucleotides can be used as the active agent component, to alter, and particular to inhibit, production of a gene in a targeted tissue, such as a gene which, when overexpressed, results in pathology. Alternatively, oligonucleotides or genes can be used to alter, and particularly to enhance, production of a protein in the targeted tissue, such as a gene that controls apoptosis or regulates cell growth; oligonucleotides or genes can also be used to produce a protein that is underexpressed or deleted in the targeted tissue (e.g., repair genetic defect in a single tissue).

In another particular embodiment, an anti-inflammatory agent can be used as the active agent. Representative agents include a non-steroidal anti-inflammatory agent; a steroidal or corticosteroidal anti-inflammatory agent; or other anti-inflammatory agent (e.g., histamine). In other embodiments, the active agent can be an agent to alter blood pressure (e.g., a diuretic, a vasopressin agonist or antagonist, angiotensin). Alternatively, in other embodiments, a pro-inflammatory agent can be used as the active agent.

Prodrugs or promolecules can also be used as the active agent. For example, a prodrug that is used as an active agent can subsequently be activated (converted) by administration of an appropriate enzyme, or by endogenous enzyme in the targeted tissue. Alternatively, the activating enzyme can be co-administered or subsequently administered as another active agent as part of a therapeutic agent as described herein; or the prodrug or promolecule can be activated by a change in pH to a physiological pH upon administration. Representative prodrugs include Herpes simplex virus thymidine kinase (HSV TK) with the nucleotide analog GCV; cytosine deaminase ans t-fluorocytosine; and other prodrugs (e.g., those described in Greco et al., J. Cell. Phys. 187:22-36, 2001; and Konstantinos et al., Anticancer Research 19:605-614, 1999; see also Connors, T. A., Stem Cells 13(5): 501-511, 1995; Knox, R. J., Baldwin, A. et al., Arch. Biochem. Biophys. 409(1):197-206, 2003; Syrigos, K. N. and Epenetos, A. A., Anticancer Res. 19(1A): 605-613, 1999; Denny, W. A., JBB 1:48-70, 2003).

In another embodiment of the invention, the targeting agent component and/or the active agent component comprises a chelate moiety for chelating a metal, e.g., a chelator for a radiometal or paramagnetic ion. In preferred embodiments, the a chelator is a chelator for a radionuclide. Radionuclides useful within the present invention include gamma-emitters, positron-emitters, Auger electron-emitters, X-ray emitters and fluorescence-emitters, with beta- or alpha-emitters preferred for therapeutic use. Examples of radionuclides useful as toxins in radiation therapy include: 32P, 33P, 43K, 47Sc, 52Fe, 57Co, 64Cu, 67Ga, 67Cu, 68Ga, 71Ge, 75Br, 76Br, 77Br, 77As, 77Br, 81Rb/81MKr, 87MSr, 90Y, 97Ru, 99Tc, 100Pd, 101Rh, 103Pb, 105Rh, 109Pd, 111Ag, 111In, 113In, 119Sb 121Sn, 123I, 125I, 127Cs, 128Ba, 129Cs, 131I, 131Cs, 143Pr, 153Sm, 161Tb, 166Ho, 169Eu, 177Lu, 186Re, 188Re, 189Re, 191Os, 193Pt, 194Ir, 197Hg, 199Au, 203Pb, 211At, 212Pb, 212Bi and 213Bi. Preferred therapeutic radionuclides include 188Re, 186Re, 203Pb, 212Pb, 212Bi, 109Pd, 64Cu, 67Cu, 90Y, 125I, 131I, 77Br, 211At, 97Ru, 105Rh, 198Au and 199Ag, 166Ho or 177Lu. Conditions under which a chelator will coordinate a metal are described, for example, by Gansow et al., U.S. Pat. Nos. 4,831,175, 4,454,106 and 4,472,509.

In one embodiment, 99 mTc can be used as a radioisotope for therapeutic and diagnostic applications (as described below), as it is readily available to all nuclear medicine departments, is inexpensive, gives minimal patient radiation doses, and has ideal nuclear imaging properties. It has a half-life of six hours which means that rapid targeting of a technetium-labeled antibody is desirable. Accordingly, in certain preferred embodiments, the therapeutic targeting agent includes a chelating agents for technium.

The therapeutic targeting agent can also comprise radiosensitizing agents, e.g., a moiety that increase the sensitivity of cells to radiation. Examples of radiosensitizing agents include nitroimidazoles, metronidazole and misonidazole (see: DeVita, V. T. Jr. in Harrison's Principles of Internal Medicine, p. 68, McGraw-Hill Book Co., N.Y. 1983, which is incorporated herein by reference). The therapeutic targeting agent that comprises a radiosensitizing agent as the active moiety is administered and localizes at the metastasized cell. Upon exposure of the individual to radiation, the radiosensitizing agent is "excited" and causes the death of the cell.

There are a wide range of moieties which can serve as chelating ligands and which can be derivatized as part of the therapeutic targeting agent. For instance, the chelating ligand can be a derivative of 1,4,7,10-tetraazacyclododecanetetraacetic acid (DOTA), ethylenediaminetetraacetic acid (EDTA), diethylenetriaminepentaacetic acid (DTPA) and 1-p-Isothiocyanato-benzyl-methyl-diethylenetriaminepentaacetic acid (ITC-MX). These chelators typically have groups on the side chain by which the chelator can be used for attachment to a targeting agent component. Such groups include, e.g., benzylisothiocyanate, by which the DOTA, DTPA or EDTA can be coupled to, e.g., an amine group of the inhibitor.

In one embodiment, the agent is an "NxSy" chelate moiety. As defined herein, the term "NxSy chelates" includes bifunctional chelators that are capable of coordinately binding a metal or radiometal and, preferably, have N2S2 or N3S cores. Exemplary NxSy chelates are described, e.g., in Fritzberg et al. (1988) PNAS 85:4024-29; and Weber et al. (1990) Bioconjugate Chem. 1:431-37; and in the references cited therein. The Jacobsen et al. PCT application WO 98/12156 provides methods and compositions, i.e. synthetic libraries of binding moieties, for identifying compounds which bind to a metal atom. The approach described in that publication can be used to identify binding moieties which can subsequently be incorporated into therapeutic targeting agents.

A problem frequently encountered with the use of conjugated proteins in radiotherapeutic and radiodiagnostic applications is a potentially dangerous accumulation of the radiolabeled moiety fragments in the kidney. When the conjugate is formed using a acid-or base-labile linker, cleavage of the radioactive chelate from the protein can advantageously occur. If the chelate is of relatively low molecular weight, it is not retained in the kidney and is excreted in the urine, thereby reducing the exposure of the kidney to radioactivity. However, in certain instances, it may be advantageous to utilize acid-or base-labile linkers in the subject ligands for the same reasons they have been used in labeled proteins.

Accordingly, the therapeutic targeting agents can be synthesized, by standard methods known in the art, to provide reactive functional groups which can form acid-labile linkages with, e.g., a carbonyl group of the ligand. Examples of suitable acid-labile linkages include hydrazone and thiosemicarbazone functions. These are formed by reacting the oxidized carbohydrate with chelates bearing hydrazide, thiosemicarbazide, and thiocarbazide functions, respectively. Alternatively, base-cleavable linkers, which have been used for the enhanced clearance of the radiolabel from the kidneys, can be used. See, for example, Weber et al. 1990 Bioconjug. Chem. 1:431. The coupling of a bifunctional chelate via a hydrazide linkage can incorporate base-sensitive ester moieties in a linker spacer arm. Such an ester-containing linker unit is exemplified by ethylene glycolbis(succinimidyl succinate), (EGS, available from Pierce Chemical Co., Rockford, Ill.), which has two terminal N-hydroxysuccinimide (NHS) ester derivatives of two 1,4-dibutyric acid units, each of which are linked to a single ethylene glycol moiety by two alkyl esters. One NHS ester may be replaced with a suitable amine-containing BFC (for example 2-aminobenzyl DTPA), while the other NHS ester is reacted with a limiting amount of hydrazine. The resulting hyrazide is used for coupling to the targeting agent component, forming an ligand-BFC linkage containing two alkyl ester functions. Such a conjugate is stable at physiological pH, but readily cleaved at basic pH.

Therapeutic targeting agents labeled by chelation are subject to radiation-induced scission of the chelator and to loss of radioisotope by dissociation of the coordination complex. In some instances, metal dissociated from the complex can be re-complexed, providing more rapid clearance of non-specifically localized isotope and therefore less toxicity to non-target tissues. For example, chelator compounds such as EDTA or DTPA can be infused into patients to provide a pool of chelator to bind released radiometal and facilitate excretion of free radioisotope in the urine.

In still other embodiments, a Boron addend, such as a carborane, can be used. For example, carboranes can be prepared with carboxyl functions on pendant side chains, as is well known in the art. Attachment of such carboranes to an amine functionality, e.g., as may be provided on the targeting agent component can be achieved by activation of the carboxyl groups of the carboranes and condensation with the amine group to produce the conjugate. Such therapeutic agents can be used for neutron capture therapy.

In a further embodiment, RNAi is used. "RNAi construct" is a generic term used throughout the specification to include small interfering RNAs (siRNAs), hairpin RNAs, and other RNA species which can be delivered ectopically to a cell, cleaved by the enzyme dicer and cause gene silencing in the cell. The term "small interfering RNAs" or "siRNAs" refers to nucleic acids around 19-30 nucleotides in length, and more preferably 21-23 nucleotides in length. The siRNAs are double-stranded, and may include short overhangs at each end. Preferably, the overhangs are 1-6 nucleotides in length at the 3' end. It is known in the art that the siRNAs can be chemically synthesized, or derive by enzymatic digestion from a longer double-stranded RNA or hairpin RNA molecule. For efficiency, an siRNA will generally have significant sequence similarity to a target gene sequence. Optionally, the siRNA molecules includes a 3' hydroxyl group, though that group may be modified with a fatty acid moiety as described herein. The phrase "mediates RNAi" refers to (indicates) the ability of an RNA molecule capable of directing sequence-specific gene silencing, e.g., rather than a consequence of induction of a sequence-independent double stranded RNA response, e.g., a PKR response.

In certain embodiments, the RNAi construct used for the active agent component is a small-interfering RNA (siRNA), preferably being 19-30 base pairs in length. Alternatively, the RNAi construct is a hairpin RNA which can be processed by cells (e.g., is a dicer substrate) to produce metabolic products in vivo in common with siRNA treated cells, e.g., a processed to short (19-22 mer) guide sequences that induce sequence specific gene silencing. In a preferred embodiment, the treated animal is a human.

The RNAi constructs contain a nucleotide sequence that hybridizes under physiologic conditions of the cell to the nucleotide sequence of at least a portion of the mRNA transcript for the gene to be inhibited (i.e., the "target" gene). The double-stranded RNA need only be sufficiently similar to natural RNA that it has the ability to mediate RNAi. Thus, the invention has the advantage of being able to tolerate sequence variations that might be expected due to genetic mutation, strain polymorphism or evolutionary divergence. The number of tolerated nucleotide mismatches between the target sequence and the RNAi construct sequence is no more than 1 in 5 basepairs, or 1 in 10 basepairs, or 1 in 20 basepairs, or 1 in 50 basepairs. Mismatches in the center of the siRNA duplex are most critical and may essentially abolish cleavage of the target RNA. In contrast, nucleotides at the 3' end of the siRNA strand that is complementary to the target RNA do not significantly contribute to specificity of the target recognition.

Sequence identity may be optimized by sequence comparison and alignment algorithms known in the art (see Gribskov and Devereux, Sequence Analysis Primer, Stockton Press, 1991, and references cited therein) and calculating the percent difference between the nucleotide sequences by, for example, the Smith-Waterman algorithm as implemented in the BESTFIT software program using default parameters (e.g., University of Wisconsin Genetic Computing Group). Greater than 90% sequence identity, or even 100% sequence identity, between the inhibitory RNA and the portion of the target gene is preferred. Alternatively, the duplex region of the RNA may be defined functionally as a nucleotide sequence that is capable of hybridizing with a portion of the target gene transcript (e.g., 400 mM NaCl, 40 mM PIPES pH 6.4, 1 mM EDTA, 50° C. or 70° C. hybridization for 12-16 hours; followed by washing).

Production of RNAi constructs can be carried out by chemical synthetic methods or by recombinant nucleic acid techniques. Endogenous RNA polymerase of the treated cell may mediate transcription in vivo, or cloned RNA polymerase can be used for transcription in vitro.

The RNAi constructs may include modifications, such as to the phosphate-sugar backbone or the nucleoside, e.g., to reduce susceptibility to cellular nucleases, improve bioavailability, improve formulation characteristics, and/or change other pharmacokinetic properties. For example, the phosphodiester linkages of natural RNA may be modified to include at least one of a nitrogen or sulfur heteroatom. Modifications in RNA structure may be tailored to allow specific genetic inhibition while avoiding a general cellular response to dsRNA (a "PKR-mediated response"). Likewise, bases may be modified to block the activity of adenosine deaminase. The RNAi construct may be produced enzymatically or by partial/total organic synthesis, any modified ribonucleotide can be introduced by in vitro enzymatic or organic synthesis.

Methods of chemically modifying other RNA molecules can be adapted for modifying RNAi constructs (see, for example, Heidenreich et al. (1997) Nucleic Acids Res, 25:776-780; Wilson et al. (1994) J Mol Recog 7:89-98; Chen et al. (1995) Nucleic Acids Res 23:2661-2668; Hirschbein et al. (1997) Antisense Nucleic Acid Drug Dev 7:55-61). Merely to illustrate, the backbone of an RNAi construct can be modified with phosphorothioate, phosphorodithioate, methylphosphonate, chimeric methylphosphonate-phosphodiesters, phosphoramidate, boranophosphate, phosphotriester, formacetal, 3'-thioformacetal, 5'-thioformacetal, 5'-thioether, carbonate, 5'-N-carbamate, sulfate, sulfonate, sulfamate, sulfonamide, sulfone, sulfite, sulfoxide, sulfide, hydroxylamine, methylene(methylimino) (MMI), methyleneoxy(methylimino) (MOMI) linkages, peptide nucleic acids, 5-propynyl-pyrimidine containing oligomers or sugar modifications (e.g., 2'-substituted ribonucleosides, a-configuration).

The double-stranded structure may be formed by a single self-complementary RNA strand or two complementary RNA strands. RNA duplex formation may be initiated either inside or outside the cell.

In certain embodiments, to reduce unwanted immune stimulation, the RNAi construct is designed so as not to include unmodified cytosines occurring 5' to guanines, e.g., to avoid stimulation of B cell mediated immunosurveillance.

In certain embodiments in which the RNAi is to be delivered for therapeutic effect in the lung, the backbone linkages can be chosen so as titrate the nuclease sensitivity to make the RNAi sufficiently nuclease resistant to be effective in the lung, but not so nuclease resistant that significant amounts of the construct could escape the tissue undegraded. With the use of this strategy, RNAi constructs are available for gene silencing in the lung tissue, but are degraded before they can enter the wider circulation. Alternatively, the RNAi construct can be designed to augment its nuclease resistance substantially, permitting systemic delivery to occur after its inhalation or other administration.

Adenosine has also been shown to cause adverse effects, including death, when administered therapeutically for other diseases and conditions in subjects with previously undiagnosed hyperreactive airways. See e.g., R. P. Cowell et al., Brit. Heart J. 71(6), 569-71 (1994); D. J. Pennell et al., Europ. J. Nuclear Med. 21(2), 170-2 (1994); R. Reed et al., Am. J. Emerg. Med. 21(4), 453 (1992). The release of adenosine as an oligonucleotide degradation product is of extreme concern because of adenosine's major role in a host of physiological processes ranging from vasoconstriction to control of sinoatrial rhythm.

The release of bioactive adenosine from oligonucleotide degradation can have very important consequences in hyperresponsive airways and also in applications involving the CNS (either direct microinjection into specific brain regions, or intrathecal administration). For example, individuals with asthma show a nearly universal hypersensitivity to inhaled adenosine and adenosine monophosphate, and adenosine released as a product of antisense oligonucleotide breakdown is capable of activating this response. An exception is on in which the receptor mediating adenosine sensitivity is downregulated by the RNAi construct administration and is therefore not available for adenosine stimulation. The administration of an RNAi construct containing adenosine might thus cause dose-limiting bronchoconstriction during the process of oligonucleotide degradation.

Similarly, the release of adenosine into the CNS during RNAi construct degradation can cause the stimulation of any or all of the four adenosine receptors (A1, A2A, A2B, or A3), potentially causing effects in any of the more than 40 different physiological processes in which these receptors have a role in the CNS.

To avoid this problem, in certain embodiments, the RNAi constructs of the present invention may be designed with the intention that adenosine content of be reduced so as to reduce its liberation upon degradation. Such liberation may cause serious, even life-threatening, bronchoconstriction in patients with hyperreactive airways. In certain embodiments, this is accomplished by using GC rich constructs, e.g., containing to no more than 3 adenosines for every 10 nucleotides, and even more preferably less than 3 adenosines for every 15 or even 20 nucleotides. In other embodiments, the RNAi contructs incorporate adenosine analogs which, while not substantially diminishing the efficiency of the RNAi construct in gene silencing, are analogs that are less active with respect to activation of adenosine receptors, are more rapidly metabolized to non-toxic agents, and/or are attached to adjacent residues using nuclease-resistant linkages so as to prevent release of free adenosine.

The RNA may be introduced in an amount which allows delivery of at least one copy per cell. Higher doses (e.g., at least 5, 10, 100, 500 or 1000 copies per cell) of double-stranded material may yield more effective inhibition, while lower doses may also be useful for specific applications. Inhibition is sequence-specific in that nucleotide sequences corresponding to the duplex region of the RNA are targeted for genetic inhibition.

In certain embodiments, the subject RNAi constructs are siRNAs. These nucleic acids are around 19-30 nucleotides in length, and even more preferably 21-23 nucleotides in length, e.g., corresponding in length to the fragments generated by nuclease "dicing" of longer double-stranded RNAs. The siRNAs are understood to recruit nuclease complexes and guide the complexes to the target mRNA by pairing to the specific sequences. As a result, the target mRNA is degraded by the nucleases in the protein complex. In a particular embodiment, the 21-23 nucleotides siRNA molecules comprise a 3' hydroxyl group.

The siRNA molecules of the present invention can be obtained using a number of techniques known to those of skill in the art. For example, the siRNA can be chemically synthesized or recombinantly produced using methods known in the art. For example, short sense and antisense RNA oligomers can be synthesized and annealed to form double-stranded RNA structures with 2-nucleotide overhangs at each end (Caplen, et al. (2001) Proc Natl Acad Sci USA, 98:9742-9747; Elbashir, et al. (2001) EMBO J, 20:6877-88). These double-stranded siRNA structures can then be directly introduced to cells, either by passive uptake or a delivery system of choice, such as described below.

In certain embodiments, the siRNA constructs can be generated by processing of longer double-stranded RNAs, for example, in the presence of the enzyme dicer. In one embodiment, the *Drosophila* in vitro system is used. In this embodiment, dsRNA is combined with a soluble extract derived from *Drosophila* embryo, thereby producing a combination. The combination is maintained under conditions in which the dsRNA is processed to RNA molecules of about 21 to about 23 nucleotides.

The siRNA molecules can be purified using a number of techniques known to those of skill in the art. For example, gel electrophoresis can be used to purify siRNAs. Alternatively, non-denaturing methods, such as non-denaturing column chromatography, can be used to purify the siRNA. In addition, chromatography (e.g., size exclusion chromatography), glycerol gradient centrifugation, affinity purification with antibody can be used to purify siRNAs.

Modification of siRNA molecules with fatty acids can be carried out at the level of the precursors, or, perhaps more practically, after the RNA has been synthesized. The latter may be accomplished in certain instances using nucleoside precursors in the synthesis of the polymer that include functional groups for formation of the linker-fatty acid moiety.

In certain preferred embodiments, at least one strand of the siRNA molecules has a 3' overhang from about 1 to about 6 nucleotides in length, though may be from 2 to 4 nucleotides in length. More preferably, the 3' overhangs are 1-3 nucleotides in length. In certain embodiments, one strand having a 3' overhang and the other strand being blunt-ended or also having an overhang. The length of the overhangs may be the same or different for each strand. In order to further enhance the stability of the siRNA, the 3' overhangs can be stabilized against degradation. In one embodiment, the RNA is stabilized by including purine nucleotides, such as adenosine or guanosine nucleotides. Alternatively, substitution of pyrimidine nucleotides by modified analogues, e.g., substitution of uridine nucleotide 3' overhangs by 2'-deoxythyinidine is tolerated and does not affect the efficiency of RNAi. The absence of a 2' hydroxyl significantly enhances the nuclease resistance of the overhang in tissue culture medium and may be beneficial in vivo.

In other embodiments, the RNAi construct is in the form of a long double-stranded RNA. In certain embodiments, the RNAi construct is at least 25, 50, 100, 200, 300 or 400 bases. In certain embodiments, the RNAi construct is 400-800 bases in length. The double-stranded RNAs are digested intracellularly, e.g., to produce siRNA sequences in the cell. However, use of long double-stranded RNAs in vivo is not always practical, presumably because of deleterious effects which may be caused by the sequence-independent dsRNA response. In such embodiments, the use of local delivery systems and/or agents which reduce the effects of interferon or PKR are preferred.

In certain embodiments, the RNAi construct is in the form of a hairpin structure (named as hairpin RNA). The hairpin RNAs can be synthesized exogenously or can be formed by transcribing from RNA polymerase III promoters in vivo. Examples of making and using such hairpin RNAs for gene silencing in mammalian cells are described in, for example, Paddison et al., Genes Dev, 2002, 16:948-58; McCaffrey et al., Nature, 2002, 418:38-9; McManus et al., RNA, 2002, 8:842-50; Yu et al., Proc Natl Acad Sci USA, 2002, 99:6047-52). Preferably, such hairpin RNAs are engineered in cells or in an animal to ensure continuous and stable suppression of a desired gene. It is known in the art that siRNAs can be produced by processing a hairpin RNA in the cell.

In particularly preferred embodiments, the active agent component is an agent for the treatment of an acquired or a congenital lung disease (e.g., asthma, interstitial pneumonia (viral or bacterial), tuberculosis, cystic fibrosis, COPD, Goodpasture's syndrome, hantavirus infection, bronchiectasis, alpha-1-antitrypsin deficiency). In another embodiment, the active agent component is an agent that allows expression of a protein that is functionally lacking, insufficiently produced, or otherwise abnormally expressed (e.g., a gene or nucleic acid encoding a protein, such as for the treatment of cystic fibrosis). Alternatively, the active agent component is an agent for treatment or prevention of organ rejection (e.g., in the case of lung transplantation). Oxidative stress and acute lung transplantation injury may be prevented by targeting of therapeutic agents to the pulmonary endothelium (see, e.g., Kozower, et al., Nature Biotech. 21:392 (2003)).

The therapeutic targeting agent, alone or in a composition, is administered in a therapeutically effective amount, which is the amount used to treat the pathology. The amount which will be therapeutically effective will depend on the nature of the pathology, the extent of disease, and other factors, and can be determined by standard clinical techniques. In addition, in vitro or in vivo assays may optionally be employed to help identify optimal dosage ranges. The precise dose to be employed in the formulation will also depend on the route of administration, and the seriousness of the symptoms, and should be decided according to the judgment of a practitioner and each patient's circumstances. Effective doses may be extrapolated from dose-response curves derived from in vitro or animal model test systems.

Imaging In Vivo and Diagnostics

In another embodiment of the invention, methods are now available to deliver imaging agents in a tissue-specific manner, for physical imaging of one or more organs or tissues, including for imaging of normal or diseased tissue (e.g., for use in assessing an individual for the presence of a pathology). The methods further pertain to the use of the described agents for manufacture of medicaments for use in physical imaging. In the methods of the invention, the imaging agent is delivered to, into and/or vascular endothelium in a tissue-specific manner through an agent of interest. As indicated above, "tissue-specific" indicates that the agent preferentially or selectively binds to a particular type of tissue (e.g., lung, vasculature, vasculature of lung) or to a specific set of tissues (e.g., lung and liver, vasculature of lung and liver, lung and kidney, vasculature of lung and kidney).

In the methods of the invention, an "imaging agent" is used. The imaging agent comprises a targeting agent component and an imaging agent component. The targeting agent component specifically binds to a targeted protein expressed on endothelial cell surface (e.g., a targeted protein as described above). The imaging agent component (comprising the imaging agent, and, if necessary, other components such as a means to couple the imaging agent component to the targeting agent component) can be, for example, a radioactive agent (e.g., radioiodine (125I, 131I); technetium; yttrium; 35S or 3H) or other radioisotope or radiopharmaceutical; a contrast agent (e.g., gadolinium; manganese; barium sulfate; an iodinated or noniodinated agent; an ionic agent or nonionic agent); a magnetic agent or a paramagnetic agent (e.g., gadolinium, iron-oxide chelate); liposomes (e.g., carrying radioactive agents, contrast agents, or other imaging agents); ultrasound agents (e.g., microbubble-releasing agents); a nanoparticle; a gene vector or virus inducing a detecting agent (e.g., including luciferase or other fluorescent polypeptide); an enzyme (horseradish peroxidase, alkaline phosphatase, β-galactosidase, or acetylcholinesterase); a prosthetic group (e.g., streptavidin/biotin and avidin/biotin); a fluorescent material (e.g., umbelliferone, fluorescein, fluorescein isothiocyanate, rhodamine, dichlorotriazinylamine fluorescein, dansyl chloride or phycoerythrin); a luminescent material (e.g., luminol); a bioluminescent material (e.g., luciferase, luciferin, aequorin); a functional imaging agent (e.g., an agent that identifies a cell in a particular functional state); or any other imaging agent that can be employed for imaging studies (e.g., for CT, fluoroscopy, SPECT imaging, optical imaging, PET, MRI, gamma imaging).

The imaging agent can be used in methods of performing physical imaging of an individual. "Physical imaging," as used herein, refers to imaging of all or a part of an individual's body (e.g., by the imaging studies methods set forth above). Physical imaging can be "positive," that is, can be used to detect the presence of a specific type of tissue or pathology. For example, in one embodiment, positive physical imaging can be used to detect the presence or absence of pathological tissue (e.g., a neoplasm and/or metastatic neoplasm). Alternatively, in another embodiment, positive physical imaging can be used to detect the presence or absence of a normal (non-disease) tissue, such as the presence of or absence of an organ. Alternatively, the physical imaging can be "negative," that is, can be used to detect the absence of a specific type of tissue or the normal state of the tissue. For example, in one embodiment, negative physical imaging can be used to detect the absence or presence of a normal tissue, where the absence is indicative of a loss of function consistent with a pathology. Both positive and negative physical imaging permit visualization and/or detection of both normal and of abnormal pathology, and can be used to quantify or determine the extent, size, and/or number of an organ or of a type of pathology (e.g., number of metastatic tumors). Thus, an estimate can be made of the extent of disease, facilitating, for example, clinical diagnosis and/or prognosis.

For physical imaging, an imaging agent is administered to the individual. These methods of physical imaging can be used, for example, to assess an individual for the presence or absence, or extent, of a pathology (e.g., by "positive" imaging as described above). In these embodiments, the targeting agent component binds to or localizes to a targeted protein that is associated with a pathology (e.g., a targeted protein that is present on the vascular endothelium of a pathological tissue; or a targeted protein that is expressed to a greater degree in a pathological tissue than in a comparable normal tissue). The agent of interest is administered to the individual (e.g., intravenously), and then the individual is assessed for the presence or absence of a concentration of the agent of interest. A "concentration," as used herein, is an amount of the agent of interest at a particular location in the individual's body that is greater than would be expected from mere circulation or diffusion of the agent of interest in the individual, or that is greater than would be expected in a comparable normal tissue in the individual. A concentration is indicative of binding of the agent of interest to the pathological tissue, and thus is indicative of the presence of the pathology.

In other embodiments, the methods can be used to assess an individual for the presence or absence of normal (non-disease) function of an organ or bodily system (e.g., by "negative" imaging as described above). In these embodiments, the targeting agent component binds to and localizes to a targeted protein present in the normal tissue but not in the pathologic (abnormal) tissue. The agent is administered to the to the individual, and then the individual is assessed for the absence (or presence) of the agent of interest. An absence of the imaging agent where it is expected in the structures targeted by the targeting agent component, in combination with the presence of the agent of interest in other parts of the structures targeted by the targeting agent component, is indicative of a loss of function that is consistent with the presence of pathology.

If desired, the agent of interest can further comprise a therapeutic agent. A "therapeutic agent," as used herein, refers to an agent that targets the pathology for destruction (e.g., a chemotherapeutic agent) or otherwise reduces or eliminates the effects of the pathology on the individual, as described above.

In preferred embodiments of the invention, the targeting agent component specifically binds to a targeted protein such as TIE-2, APN, TEM4, TEM6, ICAM-1, nucleolin, P2Z receptor, Trk-A, FLJ10849, HSPA12B, APP, or OX-45; alternatively, the targeting agent component specifically binds to a protein set forth in Table 1. In a particularly preferred embodiment, the targeting agent component specifically binds to a targeted protein such as APP or OX-45, and the imaging agent is used for imaging of lung.

Imaging Ex Vivo and Diagnostics

In another embodiment, the present invention relates to methods of delivering imaging agents in a tissue-specific manner, for use in vitro, e.g., for analysis of a tissue sample or cell sample. The term, "tissue sample," as used herein, refers not only to a sample from tissue (e.g., skin, lung, liver, kidney, or other organ), but also to a blood sample.

In one embodiment of the invention, an imaging agent, as described above, is used to perform ex vivo imaging. "Ex vivo imaging," as used herein, refers to imaging of a tissue sample or cell sample that has been removed from an individual's body (e.g., by surgical removal of a tissue sample, or a cell sample; by venipuncture; or other means). The imaging permits visualization and/or detection of normal or abnormal pathology, and can be used to quantify or determine the extent, size, and/or number of pathological cells in a sample. Thus, an estimate can be made of the extent of disease, facilitating, for example, clinical diagnosis and/or prognosis, as well as of the efficacy of treatment, by comparing the quantity, extent, size, location and/or number of pathological cells in samples taken both before and during or after treatment. Alternatively, the imaging can be used for visualization and/or detection of cells in a particular functional state, thereby enabling the quantification of the extent and/or number of cells in a particular functional state in a sample.

In one embodiment, for ex vivo imaging, the imaging agent is administered to an individual as described above. A biopsy sample can then be taken from the individual, and the biopsy sample can then be assessed for the presence or absence of a concentration of the agent of interest. Alternatively, in another embodiment of ex vivo imaging, the imaging agent as described above is applied to the tissue sample. The tissue sample can then be assessed for the presence or absence of a concentration of the agent of interest. A "concentration," as used herein, is an amount of the agent of interest that is greater than would be expected from mere diffusion of the agent of interest in the tissue sample. A concentration is indicative of binding of the agent of interest, and thus can be indicative of the presence of pathology.

Molecular Signature and Diagnostics

In view of the identification of a set of tissue-specific target proteins, methods are also now available to assess a tissue sample for a molecular signature of a particular tissue. The molecular signature comprises the tissue-specific expression of more than one of the targeted proteins described herein (e.g., TIE-2, APN, TEM4, TEM6, ICAM-1, or nucleolin P2Z receptor; Trk-A; FLJ10849; HSPA12B; APP; OX-45; or a protein as set forth in Table 1). A tissue sample can be assessed for the presence of some or all of the tissue-specific proteins; the presence of the proteins is indicative of endothelium of that particular tissue. The invention also comprises kits for use in assessing a sample for a tissue molecular signature, comprising, for example, agents (e.g., antibodies, labeled antibodies) to facilitate identification of the presence of one or more targeted proteins.

Assessment of Treatment Efficacy and Prognosis

The in vitro and/or ex vivo diagnosis methods described above can be used in methods for assessment of treatment efficacy in a patient. Thus, the current invention also pertains to methods of monitoring the response of an individual to treatment with a therapeutic agent, such as a therapeutic targeting agent, as described above, or other therapeutic agent, as well as to determine the efficacy of treatment, by comparing the quantity, extent, size, location and/or number of pathological tissues, or by comparing the quantity, extent, size, location and/or number or normal tissues, both before and during or after treatment. This monitoring of the local environment allows identification of a return to normalcy of pathological tissues.

In one embodiment, ex vivo analysis can be performed to assess treatment efficacy in a patient. Thus, the current invention also pertains to methods of monitoring the response of an individual to treatment with a therapeutic targeting agent, as described above, or other therapeutic agent. For example, in one aspect of the invention, an individual can be assessed for response to treatment with an therapeutic targeting agent or other therapeutic agent, by examining the level of the targeted protein in different tissues, cells and/or body fluids of the individual. Blood, serum, plasma or urinary levels of the targeted protein (e.g., of a targeted protein that is shed into circulation), or ex vivo production of the targeted protein, can be measured before, and during or after treatment with the therapeutic targeting agent or other therapeutic agent, as can levels of the targeted protein in tissues. The level before treatment is compared with the level during or after treatment. The efficacy of treatment is indicated by an alteration (e.g., an increase or decrease) in availability or production of the targeted protein: a level of the targeted protein during or after treatment that is significantly different from the level before treatment, is indicative of efficacy. A level that is altered during or after treatment can be shown, for example, by altered serum or urinary levels of targeted protein, or decreased ex vivo production of the targeted protein. A level that is "significantly different", as used herein, is a level that is different from the amount that is typically found in control individual(s) or control sample(s), or is different in a comparison of disease in a population associated with the other bands of measurement (e.g., the mean or median, the highest quartile or the highest quintile) compared to lower bands of measurement (e.g., the mean or median, the other quartiles; the other quintiles).

For example, the level of the targeted protein (e.g., in a blood or serum sample, or in a tissue sample) is assessed in a sample from an individual before treatment with an therapeutic targeting agent or other therapeutic agent; and during or after treatment with the therapeutic targeting agent or other therapeutic agent, and the levels are compared. A level of the targeted protein during or after treatment that is significantly different from the level of the targeted protein before treatment, is indicative of efficacy of treatment with the therapeutic targeting agent or other therapeutic agent. In another aspect, production of the targeted protein is analyzed in a first test sample from the individual, and is also determined in a second test sample from the individual, during or after treatment, and the level of production in the first test sample is compared with the level of production in the second test sample. A level in the second test sample that is significantly different from the level in the first test sample is indicative of efficacy of treatment.

In another embodiment, in vivo methods as described above can be used to compare images before and after treatment with a therapeutic targeting agent or other therapeutic agent. The extent, size, location and/or number of pathological tissues in vivo before treatment is compared with the extent, size, location and/or number during or after treatment. The efficacy of treatment is indicated by a decrease the extent, size, location and/or number of pathological tissues, as indicated by decreased concentrations of imaging agents. Alternatively or in addition, the extent, size, location and/or number of normal tissues in vivo before treatment is compared with the extent, size, location and/or number during or after treatment. The efficacy of treatment is indicated by an increase in the extent, size, location and/or number of normal tissues, as indicated by increased concentrations of imaging agents.

Alternatively, the ex vivo methods as described above can be used to compare biopsy samples before and after treatment with a therapeutic targeting agent or other therapeutic agent. The extent, size, location and/or number of pathological tissues in a sample before treatment is compared with the extent, size, location and/or number in a sample during or after treatment. The efficacy of treatment is indicated by a decrease the extent, size, location and/or number, as indicated by decreased concentrations of imaging agents. Alternatively or in addition, the ex vivo methods as described above can be used to compare biopsy samples before and after treatment with a therapeutic targeting agent or other therapeutic agent. The extent, size, location and/or number of normal tissues in a sample before treatment is compared with the extent, size, location and/or number in a sample during or after treatment. The efficacy of treatment is indicated by an increase the extent, size, location and/or number, as indicated by increased concentrations of imaging agents.

In another embodiment, in vivo methods as described above can be used to image before, during and after treatment with a therapeutic targeting agent or other therapeutic agent. For example, the extent, size, location and/or number of pathological tissues can be assessed by in vivo imaging, and a therapeutic agent is then administered to the individual. Continued, continuous or subsequent imaging of the individual can reveal real-time targeting and destruction pathological cells. Alternatively or in addition, the extent, size, location and/or number of normal tissues can be assessed by in vivo imaging, and a therapeutic agent is then administered to the individual. Continued, continuous or subsequent imaging of the individual can reveal real-time targeting and destruction pathological cells or a return to normalcy.

In another embodiment of the invention, the level of the targeted protein can be used to assess a sample for the presence of aggressive disease and/or to assess prognosis for the patient from whom the tissue sample was obtained. Because the presence of the targeted protein is indicative of normal tissue, the amount of the targeted protein is indicative of extent of disease or the degree of aggression of disease: lower amounts of the targeted protein are indicative of greater extent of disease, which similarly corresponds to a poorer prognosis. Aggressive disease will show a decreased amount of the targeted protein in tumors, compared to less aggressive disease.

Tissue Engineering

Because certain proteins have been identified as being prevalent on endothelium of specific tissues, as described herein, methods are now available to create cell types in culture that are more similar to those in vivo. (See, e.g., Engelmann, K. Et al., Exp Ehye Res (2004) 78(3):573-8; Kirkpatrick, C. J. et al., Biomol. Eng. (2002):19(2-6):211-7; Nugent, H. M. and Edelman, E. R., Circ. Res. (2003) 92(10): 1068-780). Cells in vitro that are more similar to those in vivo, by virtue of producing similar panels of proteins on the endothelial surface, provide a better tool for assessing agents that may be useful, for example, in therapies such as the therapies described herein. Cells can be modified, for example, by incorporation of nucleic acids or vectors expressing proteins that are produced in particular tissues in vivo, compared to expression in in vitro cell culture. Such modified cells allow more accurate assessment of effects of a potential therapeutic agent on cells of particular tissues.

Antibodies of the Invention

In another aspect, the invention provides antibodies to certain targeted proteins, that can be used, for example, in the methods of the invention. The term "antibody" is described above. The invention provides polyclonal and monoclonal antibodies that bind to a targeted protein. The term "monoclonal antibody" or "monoclonal antibody composition", as used herein, refers to a population of antibody molecules that contain only one species of an antigen binding site capable of immunoreacting with a particular epitope of the targeted protein.

Polyclonal antibodies can be prepared as described above by immunizing a suitable subject with a desired immunogen, e.g., the targeted protein or a fragment or derivative thereof. The antibody titer in the immunized subject can be monitored over time by standard techniques, such as with an enzyme linked immunosorbent assay (ELISA) using immobilized polypeptide. If desired, the antibody molecules directed against the targeted protein can be isolated from the mammal (e.g., from the blood) and further purified by well-known techniques, such as protein A chromatography to obtain the IgG fraction. At an appropriate time after immunization, e.g., when the antibody titers are highest, antibody-producing cells can be obtained from the subject and used to prepare monoclonal antibodies by standard techniques, such as the hybridoma technique originally described by Kohler and Milstein (1975) Nature, 256:495-497, the human B cell hybridoma technique (Kozbor et al. (1983) Immunol. Today, 4:72), the EBV-hybridoma technique (Cole et al. (1985), Monoclonal Antibodies and Cancer Therapy, Alan R. Liss, Inc., pp. 77-96) or trioma techniques. The technology for producing hybridomas is well known (see generally Current Protocols in Immunology (1994) Coligan et al. (eds.) John Wiley & Sons, Inc., New York, N.Y.). Briefly, an immortal cell line (typically a myeloma) is fused to lymphocytes (typically splenocytes) from a mammal immunized with an immunogen as described above, and the culture supernatants of the resulting hybridoma cells are screened to identify a hybridoma producing a monoclonal antibody that binds a polypeptide of the invention.

Any of the many well known protocols used for fusing lymphocytes and immortalized cell lines can be applied for the purpose of generating a monoclonal antibody to a targeted protein (see, e.g., Current Protocols in Immunology, supra; Galfre et al. (1977) Nature, 266:55052; R. H. Kenneth, in Monoclonal Antibodies: A New Dimension In Biological Analyses, Plenum Publishing Corp., New York, N.Y. (1980); and Lerner (1981) Yale J. Biol. Med., 54:387-402. Moreover, the ordinarily skilled worker will appreciate that there are many variations of such methods that also would be useful.

Alternative to preparing monoclonal antibody-secreting hybridomas, a monoclonal antibody to a targeted protein can be identified and isolated by screening a recombinant combinatorial immunoglobulin library (e.g., an antibody phage display library) with the targeted protein, to thereby isolate immunoglobulin library members that bind to the targeted protein. Kits for generating and screening phage display libraries are commercially available (e.g., the Pharmacia Recombinant Phage Antibody System, Catalog No. 27-9400-01; and the Stratagene SurfZAP™ Phage Display Kit, Catalog No. 240612). Additionally, examples of methods and reagents particularly amenable for use in generating and screening antibody display library can be found in, for example, U.S. Pat. No. 5,223,409; PCT Publication No. WO 92/18619; PCT Publication No. WO 91/17271; PCT Publication No. WO 92/20791; PCT Publication No. WO 92/15679; PCT Publication No. WO 93/01288; PCT Publication No. WO 92/01047; PCT Publication No. WO 92/09690; PCT Publication No. WO 90/02809; Fuchs et al. (1991) Bio/Technology, 9:1370-1372; Hay et al. (1992) Hum. Antibod. Hybridomas, 3:81-85; Huse et al. (1989) Science, 246:1275-1281; Griffiths et al. (1993) EMBO J., 12:725-734.

Additionally, recombinant antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art.

In general, antibodies of the invention (e.g., a monoclonal antibody) can be used in the methods of the invention. For example, an antibody specific for a targeted protein can be used in the methods of the invention to image a neoplasm, in order to evaluate the abundance and location of neoplasm. Antibodies can thus be used diagnostically to, for example, determine the efficacy of a given treatment regimen, by imaging before and after the treatment regimen.

Paradigm for Analysis of In Vivo Endothelial Membranes and Comparison to In Vitro Cells The invention described herein finds its roots in a logic-based discovery and validation platform that integrates newly developed, state-of-the-art global analytical techniques to map the proteins expressed in vivo at the luminal endothelial cell surface and reveal distinct molecular signatures in normal and neoplastic tissues. The strategy was applied to rat lungs to uncover, from the vast number of proteins expressed in tissue, a select set of proteins expressed differentially, including two promising tissue-selective endothelial cell surface proteins permitting rapid and specific immunotargeting and imaging in vivo (APP and OX-45). Profiling the endothelial cell surface accessible in vivo demonstrates tissue-modulated endothelial cell diversity in vivo and allows discovery of targets not only to direct pharmacodelivery and molecular imaging but also to overcome the restrictive endothelial cell barrier to transport drugs or genes to the underlying tissue cells (Carver, L. A. & Schnitzer, J. E. Caveolae: mining little caves for new cancer targets. Nat Rev Cancer 3, 571-81 (2003); Schnitzer, J. E. Vascular targeting as a strategy for cancer therapy. N Engl J Med 339, 472-4 (1998)).

Key features of the analysis include the application of tissue subfractionation with subtractive proteomic and bioinformatic filters that together reduced tissue complexity by >5 orders of magnitude to unmask a manageable subset of proteins at the inherently accessible blood-tissue interface. This has allowed the creation a database of vascular endothelial cell surface proteins, including accessible proteins apparently modulated by the tissue. After bioinformatic filtering, Western analysis and/or tissue immunostaining then provides sensitive expression profiling to yield only a few candidate proteins exhibiting organ- (or neoplasm-) specificity. Planar and SPECT imaging, using intravenously-injected antibodies specific to each protein, visualizes targeting and tissue accumulation with high sensitivity and resolution. Imaging thus provides a rigorous and objective validation of accessibility and tissue-specificity of the few remaining candidate targets and ultimately reveals potential utility by how rapidly, and to what extent, the antibody targets single organs or neoplasms in vivo.

Although the invention has been described in particular in relation to lung tissue, the methods described herein are equally applicable to a wide variety of tissue types. Using the tissue subfractionation and subtractive proteomic and bioinformatic filters as described herein, analysis can be performed on tissues in order identify proteins specific to that tissue in vivo. Examples of representative tissue subractionation and subtractive proteomic and bioinformatic filter applications include: in vivo vs. in vitro; one normal tissue vs. another normal tissue; one normal tissue vs. many other normal tissues; normal tissue vs. disease tissue. Thus, the invention contemplates use of the methods and compositions as described herein for a wide range of tissue types. The invention can also be used for identification of neoplasm-specific proteins, as is described in more detail in U.S. Provisional Application Ser. No. 60/576,116, filed on Jun. 2, 2004, entitled, "VASCULAR TARGETS FOR DETECTING, IMAGING AND TREATING TUMORS,"; U.S. Application Ser. No. 11/143,886, filed on Jun. 2, 2005, entitled, "VASCULAR TARGETS FOR DETECTING, IMAGING AND TREATING NEOPLASIA OR NEOVASCULATURE"; in U.S. Provisional Application Ser. No. 60/576,192, filed on Jun. 2, 2004, entitled, "TUMOR—SPECIFIC IMAGING AND THERAPEUTIC AGENTS TARGETING PROTEINS EXPRESSED ON TUMOR ENDOTHELIAL CELL SURFACE"; and U.S. Application Ser. No. 11/143,919, filed on Jun. 2, 2005, entitled, "IMAGING AND THERAPEUTIC AGENTS TARGETING PROTEINS EXPRESSED ON ENDOTHELIAL CELL SURFACE". The teachings of these applications are incorporated herein by reference in their entirety.

The invention is further illustrated by the following Exemplification, which is not intended to be limiting in any way. The teachings of all references cited herein are incorporated by reference in their entirety.

EXEMPLIFICATION

Example 1

Direct Proteomic Mapping of the Lung Microvascular Endothelial Cell Surface In Vivo and in Cell Culture Materials and Methods.

Materials. Standard laboratory chemicals were HPLC grade or higher if available and purchased from VWR unless otherwise noted. Tris (2-Carboxyethyl)-Phosphine Hydrochloride (TCEP) was obtained from Pierce (Rockford, Ill.). Iodoacetamide was obtained from Aldrich (Milwaukee, Wis.). Porozyme bulk immobilized typsin was purchased from Applied Biosystems (Framingham, Mass.). Endoproteinase Lys-C was purchased from Roche Diagnostics (Indianapolis, Ind.). 3× Cell lysis buffer (CLB) contains 6M Urea, 0.5 M Trisbase, 9 mM EDTA, 3.6% β-mercaptoethanol and 9% sodiumdodecylsulfate.

Antibodies were obtained: ACE, APN, caveolin-1, E-cadherin, Tie 2, PECAM, and VE-Cadherin from Santa Cruz Biotechnology (Santa Cruz, Calif.); aquaporin-1, cytochrome C, ERp72, EEA1, eNOS, Lamp1, Lyn, P2×7, Ran, Transportin, CD26, and ZO-2 were obtained form BD Biosciences/Pharmingen (San Diego, Calif.); β-COP, fibroblast surface protein, glycophorin A, and p58K from Sigma (Saint Louis, Mo.); CD4 and CD11 from Serotech (Raleigh, N.C.). HSP47 from Stressgen Biotechnologies (Victoria, British Columbia, Canada). RAGE from Affinity Bioreagents (Golden, Colo.); ECE from Zymed Lab, Inc. (San Francisco, Calif.); Trk-A from ABcam (Cambridge, Mass.); nucleolin from Leinco Technologies (St. Louis, Mo.); Antibodies against carbonic anhydrase were a kind gift of W. S. Sly, St.

Louis University (St. Louis, Mo.); podocalyxin, PV-1, and ICAM-1 were produced in house; NHERF-2 were a kind gift of Dr. Weinman, University of Maryland Hospital, (Baltimore, Md.) (Weinman, E. J., Steplock, D. & Shenolikar, S. Acute regulation of NHE3 by protein kinase A requires a multiprotein signal complex. Kidney Int 60, 450-454 (2001)); 5' nucleotidase were a kind gift of Dr. Paul Luzio, (Cambridge, England); seven transmembrane receptor; Ig-hepta were a kind gift of Dr. Shigehisa Hirose, Tokyo Institute of Technology (Yokohama, Japan) (Abe, J., Suzuki, H., Notoya, M., Yamamoto, T. & Hirose, S. Ig-hepta, a novel member of the G protein-coupled hepta-helical receptor (GPCR) family that has immunoglobulin-like repeats in a long N-terminal extracellular domain and defines a new subfamily of GPCRs. J. Biol. Chem. 274, 19957-19964 (1999)); OX-45 were a kind gift of Dr. Neil Barclay, University of Oxford (Oxford, UK) (van der Merwe, P. A. et al. The NH2-terminal domain of rat CD2 binds rat CD48 with a low affinity and binding does not require glycosylation of CD2. Eur J Immunol 23, 1373-1377 (1993)); Pincher were a kind gift of Dr. Simon Haleguola, State University of New York (Stony Brook, N.Y.).

Cell culture. Rat lung microvascular endothelial cells (RLMVEC) were isolated and grown as described originally (Magee, J. C., Stone, A. E., Oldham, K. T. & Guice, K. S. Isolation, culture, and characterization of rat lung microvascular endothelial cells. Am J Physiol 267, L433-441 (1994)).

SDS page and Western analysis. SDS page and Western analysis were performed as described previously (Schnitzer, J. E., Liu, J. & Oh, P. Endothelial caveolae have the molecular transport machinery for vesicle budding, docking, and fusion including VAMP, NSF, SNAP, annexins, and GTPases. J. Biol. Chem. 270, 14399-14404 (1995)).

Tissue immunostaining. Frozen rat lung tissue was cut (5 m) on a Microm HM505E cryomicrotome. Sections were fixed with neutral buffered formalin for 5 min at room temperature then incubated for one hour at room temperature in blocking solution (5% FBS, 0.1% Tween 20 in PBS). After a 2-hour incubation at room temperature in primary antibodies (diluted in blocking solution) the sections were washed then treated with the biotin-conjugated secondary antibody (KPL Laboratories, Gaithersburg, Md.) for 1 hour at room temperature, washed again then treated with a streptavidin-conjugated horseradish peroxidase (KPL Laboratories, Gaithersburg, Md.) for 1 hour at room temperature. Immune complexes were detected using a Liquid DAB staining kit from BioGenex (San Ramon, Calif.). Sections were counterstained with hematoxylin, dehydrated, mounted in Permount (Fisher Scientific), and imaged digitally by light microscopy using a Nikon Eclipse E800 equipped with a Nikon digital camera DXM1200.

Production of polyclonal antibodies. Antigenicity predictions for HSPA12B and septin homolog FLJ10849 were performed using Lasergene (DNAStar, Inc Madison, Wis.) using the prediction methods of Margalite and Berzofsky, Rothbard and Taylor and Jameson Wolf. Polyclonal antibodies in rabbit were produced for HSPA12B against the peptide Ac-CGY-TARDYYHDLDPEEAR-CONH2 (SEQ ID NO:1) and against FLJ10849 against the peptide Ac-CQLLQSQAQQS-GAQQTKKD-CONH2 (SEQ ID NO:2) by Biosource (Camarillo, Calif.).

Isolation of luminal endothelial cell plasma membranes (P) from rat lungs and RLMVEC. The luminal endothelial cell plasma membranes were isolated directly from rat lung tissue or cell culture using a silica-coating procedure as described (Schnitzer, J. E., McIntosh, D. P., Dvorak, A. M., Liu, J. & Oh, P. Separation of caveolae from associated microdomains of GPI-anchored proteins. Science 269, 1435-1439 (1995); Oh, P. & Schnitzer, J. in Cell Biology: A laboratory handbook, Vol. 2 34 ff (Academic Press, 1998)). Briefly, rat lungs were perfused in situ via the pulmonary artery with a colloidal silica solution to coat the luminal endothelial cell surface. The endothelial cell plasma membrane fraction from RLMVEC cells were obtained by overlaying the cell monolayer with colloidal silica solution. The silica coating was crosslinked with polyacrylic acid prior to homogenization. Centrifugation of the homogenate through high density media sediments the silica-coated endothelial cell plasma membranes (P) into a membrane pellet away from all the other much less dense tissue components in the lung homogenate or the total RLMVEC lysate (H).

Preparation of enzymatic digest of protein mixtures for mass spectrometric analysis. The proteins in P were solubilized using CLB before vortexing and boiling for 5 minutes. The protein concentration was determined by the micro BCA assay from Pierce (Rockford, Ill.). Silica particles were sedimented by centrifugation to collect the solubilized proteins in the supernatant which was then chloroform/methanol precipitated and then re-solubilized in 8 M urea adjusted to pH 8.5 in 100 mM ammonium bicarbonate. Protein disulfide bonds were reduced with 2.5 mM Tris (2-Carboxyethyl)-Phosphine Hydrochloride (TCEP) for 15 min at 60° C. then carboxyamidomethylated with 3.75 mM iodo acetamide for 15 min at 25° C. in the dark followed by a first site specific enzymatic digestion with Endoproteinase Lys-C for 4 h at 37° C., 1:100 (w/w). then digested for a second time with Poroszyme immobilized trypsin (10 μl/100 μg protein) was performed overnight at 37° C., while agitation) after the protein mixture was diluted to 1.6 M urea with 100 mM ammonium bicarbonate, pH 8.5. The immobilized trypsin was then removed by centrifugation and the peptides in the supernatant concentrated by solid phase extraction with SPEC-PLUS PTC 18 cartridges (Ansys Diagnostics, Lake Forest, Calif.) following the manufacturer's instructions. After lyophilizing the peptide mixture to near dryness the samples were stored in sample buffer (5% acetonitrile, 0.3% formic acid) at a concentration of 5 μg/μl (calculated from the initial amount of protein) at −20 C before mass spectrometric analysis.

Multidimensional protein identification technology (MudPIT). In each experiment approximately 150 μg of complex peptide mixture was separated by two-dimensional liquid chromatography. The first dimension was based on strong cation exchange and the second dimension on C18 reversed phase hydrophobic interaction chromatography. Both chromatographic materials were packed seamlessly into a frittless micro-column. A 5 μm tip was pulled on a fused-silica microcapillary (100 μm i.d.×365 μm o.d.; Polymicro, AZ) using a Model P-2000 laser puller (Sutter Instrument Co., Novato, DA). The micro-column was then packed with three phases of chromatographic material as follows: 8.5 cm of 5 μm C18 reversed phase material (Polaris C 18-A, Metachem, Torrance, Calif.), then 4 cm of 5 μm, 300 □ strong cation exchanger (PolyLC, Columbia, Md.) and lastly 3.5 cm of C18 material using a helium pressure cell operated at 600-900 psi (Mass Evolution, Spring, Tex.). After equilibrating the microcapillary column with sample buffer, 30 μl of the complex peptide mixture (150 μg) was loaded off-line onto the microcapillary column which was then mounted onto a micro-cross (Upchurch Scientific, Oak Harbor, Wash.) and placed in-line with an Agilent 1100 quaternary HPLC. Peptides were directly eluted into the mass spectrometer using a 2D chromatography with 18 step-elutions from the strong cation exchanger followed by a gradient elution of the reversed phase material (Washburn, M. P., Wolters, D. & Yates, J. R., 3rd Large-scale analysis of the yeast proteome by multidimensional protein identification technology. Nature Biotechnology 19, 242-247 (2001)). The buffer solutions used were: buffer A: 5% (v/v) acetonitrile and 0.1% (v/v) formic acid; buffer B: 80% (v/v) acetonitrile and 0.1% (v/v) formic acid; buffer C: 500 mM ammonium acetate, 5% (v/v) acetonitrile and 0.1% (v/v) formic acid. Step 1 consisted of a 110 min gradient form 0 to 100% buffer B and was followed by steps 2-18. Each step consisted of a 135 min gradient including pre-gradient salt steps with increasing concentrations of ammonium acetate. The profile of steps 2-18 was: 5 min 100% buffer A followed by 3 min x % buffer C (x % corresponding to: 25, 37.5, 50, 58.5, 67, 75, 83.5, 91.5, 100, 125, 150, 175, 200, 225, 250 and 500 mM ammonium acetate) followed by 5 min 100 buffer A, a 5 min gradient to 15% buffer B, a 60 min gradient to 45% buffer B, followed by a 32 min gradient to 100% buffer B and 5 min 100% buffer B followed by a 10 min gradient to 100% buffer A and 10 min isocratic re-equilibration at 100% buffer A. The 100 µl/min flow-rate at the HPLC was reduced 400 fold by a fused silica capillary (50 µm id, 365 µm od) splitter placed on the micro-cross.

Mass spectrometric measurements were performed on a LCQ Deca XP ion trap mass spectrometer (ThermoFinnigan, San Jose, Calif.) equipped with a modified micro-electrospray ionization source from Mass Evolution (Spring, Tex.). A spray voltage of 2.0 kV was applied pre-column at the liquid junction of the micro-cross as described (Link, A. J. et al. Direct analysis of protein complexes using mass spectrometry. Nature Biotechnology 17, 676-682 (1999)). Operation of the quarternary Agilent 1100 HPLC pump and the mass spectrometer was fully automated during the entire procedure using the Excalibur 1.2 data system (ThermoFinnigan, San Jose, Calif.). Continuous cycles of one full scan (m/z 400 to 1400) followed by 3 data-dependent MS/MS measurements at 35% normalized collision energy were performed. MS/MS measurements were allowed for the 3 most intense precursor ions with an enabled exclusion list of 25 m/z values (+/−1.5 Da) or a maximum time limit of 5 minutes. The zoom scan function to determine the charge state was disabled in order to increase the duty cycle of the instrument. Database search and analysis of tandem mass spectra. MS/MS spectra were extracted from raw files requiring a minimum of 21 signals with an intensity of at least $4.75 \times 10^4$ a.u. Extracted MS/MS spectra were automatically assigned to the best matching peptide sequence using the SEQUEST algorithm (Eng, J., McCormac, A. & Yates, J.r. An approach to correlate tandem mass spectral data of peptides with amino acid sequences in a protein database. J. Am. Soc. Mass Spec. 5, 976-989 (1994)) and the Sequest Browser software package (ThermoFinnigan, San Jose, Calif.). SEQLEST searches were performed on independent dual processor (2.0-2.6 GHz) personal computers against a rat protein database containing 40,800 protein sequences downloaded as FASTA formated sequences from ENTREZ (NCBI; http://www.ncbi.nlm.nih.gov/Entrez). Sequence redundancies were removed using Perl script. To increase the search speed the protein database was pre-processed to create a binary database containing all possible tryptic peptides of the searched database. Any static and dynamic modifications that would account for post-translational and chemical modifications were neglected. The peptide mass search tolerance was set to 3 Da. Spectral matches were retained with a minimal cross-correlation score (XCorr) of 1.5, 2.2 and 3.3 for charge states +1, +2 and +3 respectively. DeltaCN (top match's XCorr minus the second-best match's XCorr devided by top match's XCorr) had to be equal or less than 0.07. Retained spectral matches were filtered and re-assigned to proteins using DTASelect (Tabb, D. L., McDonald, W. H. & Yates, J. R., 3rd DTASelect and Contrast: tools for assembling and comparing protein identifications from shotgun proteomics. J Proteome Res 1, 21-26 (2002)). DTASelect outputs of independent measurements were entered into Accessible Vascular Targets database (AVATAR). AVATAR was designed to store a large amount of mass spectrometric data and to provide tools to analyze the data to extract valuable information. We used relational models for database design based on Entity-Relationship and implemented the database in the MySQL relational database management system to support database query and management. This relational database plus Perl-based user-friendly interface have greatly improved data organization, data consistency and integrity, and facilitated data comparison and information retrieval. For some of the analysis to increase coverage of known EC markers, a larger database containing over 200,000 protein sequences (human, mouse and rat) were also used.

Removal of protein redundancy. AVATAR allowed a detailed analysis of parameters such as reproducibility and combined sequence coverage. The final protein list created from all peptide sequences obtained by MS/MS was compiled using AVATAR to retrieve the minimum number of proteins identified by 3 peptide spectra. If multiple entries of the same protein from different species (i.e. mouse and human) other than rat were present only the species with the better spectrum coverage was manually retained. In the case of multiple isoforms or splice variants of a protein being assigned to the same set of peptides and it was not unambiguously possible to distinguish them, we manually reduced this list to one primary entry.

Analysis of the reproducibility of MudPIT measurements. 12 independent 18-step MudPIT experiments of rat lung P sample were statistically analyzed to evaluate the benefit of repetitive MudPIT measurements. After each additional experiment we determined the fraction of proteins that were represented in at least two experiments and the percentages of proteins that were only present in one single experiment. Because this analysis can depend on the sequence by which the experiments are analyzed, we limited potential bias from any particular order of experiments by analyzing 12 different experiment sequences where the order of the experiments was systematically permutated by shifting the first experiment to the last position.

In silico protein analysis. The molecular weights and pIs of each protein based on its primary amino acid sequence were calculated using the Expasy web server (http://us.expasy.org/tools/pi_tool.html). The actual molecular weights and pIs may differ slightly from the calculated values because post-translational modifications are not considered by the program at this time. SwissProt (http://us.expasy.org/sprot/sprot-top.html) and the National Center Biotechnology Information (NCBI; http://www.ncbi.nlm.nih.gov/entrez/query.fcgi) protein and literature databases were used to classify proteins according to their currently known predominant subcellular location. Known or predicted transmembrane spanning alpha helices were determined through the literature or by using the web-based prediction program TMHMM v2.0 (provided by the Center for Biological Sequence Analysis of the Technical University in Denmark http://www.cbs.dtu.dk/services/TMHMM-2.0). Only 100% probabilities were taken into consideration. Searches for protein families and hidden markov models were performed using pfam (http://www.sanger.ac.uk/software/pfam/index.html).

Results

Sample preparation and quality control. The silica-coating methodology (Schnitzer, J. E., McIntosh, D. P., Dvorak, A. M., Liu, J. & Oh, P. Separation of caveolae from associated microdomains of GPI-anchored proteins. Science 269, 1435-1439 (1995); Oh, P. & Schnitzer, J. in Cell Biology: A laboratory handbook, Vol. 2 34 ff (Academic Press, 1998); Rizzo, V., Morton, C., DePaola, N., Schnitzer, J. E. & Davies, P. F.

Recruitment of endothelial caveolae into mechanotransduction pathways by flow conditioning in vitro. Am J Physiol Heart Circ Physiol 285, H1720-1729 (2003); Schnitzer, J. E., Liu, J. & Oh, P. Endothelial caveolae have the molecular transport machinery for vesicle budding, docking, and fusion including VAMP, NSF, SNAP, annexins, and GTPases. J. Biol. Chem. 270, 14399-14404 (1995); Schnitzer, J. E. & Oh, P. Aquaporin-1 in plasma membrane and caveolae provides mercury-sensitive water channels across lung endothelium. Am J Physiol 270, H416-422 (1996)) was used to isolate endothelial cell plasma membranes from rat lungs and from cultured rat lung microvascular endothelial cells (RLMVEC; isolated and grown in culture as in past work (Schnitzer, J. E. & Oh, P. Antibodies to SPARC inhibit albumin binding to SPARC, gp60, and microvascular endothelium. Am. J. Phys. 263, H1872-1879 (1992)) for comparative analysis of their proteins by two-dimensional (2-D) liquid chromatography tandem mass spectrometry (LC/LC-MS/MS). Briefly, a solution of cationic colloidal silica particles was used to selectively coat the endothelial cell surface either by perfusing the lung vasculature via the pulmonary artery in situ or by overlaying RLMVEC confluent monolayers. After electrostatic cross-linking and quenching with polyacrylic acid to form a stable membrane pellicle, the tissue or cells were homogenized and the sheets of silica-coated membranes are sedimented by two rounds of ultracentrifugation through high-density media. This subfractionation yielded a membrane pellet highly enriched in endothelial cell surface markers and markedly depleted of markers of other cell types and subcellular organelles (Schnitzer, J. E., McIntosh, D. P., Dvorak, A. M., Liu, J. & Oh, P. Separation of caveolae from associated microdomains of GPI-anchored proteins. Science 269, 1435-1439 (1995); Oh, P. & Schnitzer, J. in Cell Biology: A laboratory handbook, Vol. 2 34 ff (Academic Press, 1998); Rizzo, V., Morton, C., DePaola, N., Schnitzer, J. E. & Davies, P. F. Recruitment of endothelial caveolae into mechanotransduction pathways by flow conditioning in vitro. Am J Physiol Heart Circ Physiol 285, H1720-1729 (2003); Schnitzer, J. E., Liu, J. & Oh, P. Endothelial caveolae have the molecular transport machinery for vesicle budding, docking, and fusion including VAMP, NSF, SNAP, annexins, and GTPases. J. Biol. Chem. 270, 14399-14404 (1995); Schnitzer, J. E. & Oh, P. Aquaporin-1 in plasma membrane and caveolae provides mercury-sensitive water channels across lung endothelium. Am J Physiol 270, H416-422 (1996)).

To ensure the use of consistently high-quality material, each lot of tissue/cell homogenate (H) and isolated silica-coated endothelial cell membranes (P) was subjected to rigorous quality control testing before analysis. Using standard immunoblotting, it was required that the purity level of plasma membranes in P relative to H to be at least 20-fold enriched in at least 2 endothelial cell surface marker proteins, such as caveolin, 5'-nucleotidase (5'NT), VE-cadherin-1, angiotensin converting enzyme (ACE) or endothelial nitric oxide synthase (eNOS). In addition, P had to be depleted by 20-fold relative to H in well-established organellar membrane markers, including nuclear (ran, transportin), endosomal (early endosome antigen 1 (EEA 1)), Golgi (p58, β-COP), lysosomal (lamp1), mitochondrial (cytochrome c), and endoplasmic reticulum (ER) (ERp72). For rat lung P, a 20-fold depletion in protein markers of membranes from other cell types present in lung or blood, including epithelial cells (E-cadherin), fibroblasts (FSP), white blood cells (CD11, CD4) and red blood cells (glycophorin A) was required. Using these quality control criteria, one can expect >95% purity of the samples.

Reproducibility and analytical completeness of the mass spectrometric analysis. To render a comprehensive analysis of rat lung endothelial cell surface proteins, we performed >30 measurements using multidimensional protein identification technology (MudPIT)(Wolters, D. A., Washburn, M. P. & Yates, J. R., 3rd An automated multidimensional protein identification technology for shotgun proteomics. Anal Chem 73, 5683-5690 (2001)) on P isolated from rat lungs and RLMVEC (see methods). To estimate the number of MudPIT measurements required for completing as comprehensive an analysis as possible with our instrumentation and protein database, repeated MudPIT measurements were statistically analyzed to determine at which point additional experiments produce little new information (i.e., newly identified proteins). Using an identification criterion of at least 2 MS/MS spectra of true tryptic peptides, it was found that for the analysis of rat lung P, an average of 66% of the identified proteins in any measurement were confirmed by any second measurement so that 34% of the proteins remained unconfirmed. Adding a third measurement decreased proteins found only in the first experiment to 20%. After 10 measurements, this number leveled off at 4.2% so that few proteins are identified for the first time (i.e. not found in the other 9 measurements). The term "confidence of analytical completeness" is used to describe this definition for reproducibility. Note that the confidence of analytical completeness may depend on many factors, including the complexity of the individual sample being analyzed, the quality of the chromatography, and the sensitivity of the instrument. The same 95% confidence of analytical completeness was achieved for the RLMVEC analysis after 7 MudPIT measurements.

To evaluate further the reproducibility and relative comprehensiveness of individual measurements, we performed measurements on up to 5 aliquots taken from the same lot of P. Using the same statistical analysis, we detected no differences when the comparatively analyzed measurements were from the same rat lung P sample or from P samples produced independently. An average 260 (47) unique proteins were identified in each MudPIT experiment with >2 MS/MS spectra. Large-scale MS analysis of rat lung endothelium. The MudPIT analysis of rat lung P and RLMVEC P was entered into a relational database developed in-house that allowed us to combine all results of individual measurements and analyze them separately or in totality. 450 non-redundant proteins of the rat lung endothelium were identified (Table 1).

TABLE 1

| Protein name | NCBI locus | SwissProt or Trembl locus | Number of MS/MS spectra | | PI | MW | Function | Predicted TMs |
| --- | --- | --- | --- | --- | --- | --- | --- | --- |
| | | | Lung P | RLMVEC | | | | |
| Integral and lipid-anchored plasma membrane proteins | | | | | | | | |
| ADP/ATP translocase 2 | 728810 | Q09073 | 3 | 7 | 9.74 | 32901 | transport | 2 |
| ADP-ribosyl cyclase 1 (CD3BH) | 2483428 | Q64244 | 4 | 3 | 8.83 | 34436 | other | 1 |
| ALCAM (CD166) | 2589007 | O35112 | 3 | — | 5.77 | 65022 | adhesion | 1 |
| Aminopeptidase N | 113750 | P15684 | 3 | 4 | 5.30 | 109317 | ee | 1 |

TABLE 1-continued

| Protein name | NCBI locus | SwissProt or Trembl locus | Number of MS/MS spectra | | PI | MW | Function | Predicted TMs |
|---|---|---|---|---|---|---|---|---|
| | | | Lung P | RLMVEC | | | | |
| Angiolensin-converting enzyme (CD134) | 11493661 | P12821 | 44 | — | 5.85 | 149715 | ee | 1 |
| Antigen peptide transporter 2 | 407477 | P36372 | 3 | 2 | 6.27 | 77713 | transport | 5 |
| Aquaporin 1 | 312924 | P29975 | 3 | — | 7.70 | 28830 | transport | 6 |
| Atrial nautriuretic peptide receptor A | 204270 | P18910 | 5 | — | 6.58 | 118951 | signaling | 1 |
| Carbonic anhydrase IV | 544726 | P48284 | 11 | — | 6.31 | 35076 | ee | GPI |
| Caveolin-1 | 17017233 | Q8VIK9 | 13 | 5 | 5.30 | 20553 | traffick | 1 |
| Caveolin-2 | 17017237 | Q8VIK7 | 4 | 1 | 5.65 | 18175 | traffick | 2 |
| CD9 antigen | 729088 | P40241 | 3 | 2 | 7.25 | 25084 | adhesion | 4 |
| CDC42 | 31542368 | Q8CFN2 | 3 | 2 | 5.76 | 21311 | signaling | prenylate |
| Cell surface glycoprotein MUC18 | 10566949 | X | 5 | — | 5.74 | 71373 | other | 1 |
| Cerebral protein-11 | 34880202 | O75069 | 5 | — | 5.67 | 81692 | other | 2 |
| Chloride intracelluar channel 5 | 12232044 | Q9EPT8 | 12 | — | 5.64 | 28299 | transport | ion channel |
| Complement component C1q receptor (entothelial-CD93 antigen) | 9886763 | Q9ET61 | 4 | — | 4.87 | 66782 | other | 1 |
| C-Yes | 12539401 | Q99PW1 | 4 | 5 | 6.22 | 60588 | signaling | myristate |
| Cytolysin | 203894 | P35783 | 5 | — | 8.18 | 61513 | other | channel |
| Dipeptidyl peptidase IV (CD26) | 118905 | P14740 | 31 | — | 5.87 | 88003 | ee | 1 |
| Ecto-apyrase (CD39) | 1754710 | P97687 | 4 | — | 7.48 | 57408 | ee | 2 |
| Ecto-ATPase | 203990 | P16573 | 3 | — | 5.62 | 57264 | ee | 1 |
| Endothelial cell-selective adhesion molecule | 27720013 | X | 8 | — | 8.53 | 31382 | adhesion | 1 |
| Endothelin converting enzyme | 529085 | P42893 | 7 | — | 6.37 | 86126 | ee | 1 |
| Flotillin-2 | 4097589 | O9Z2S9 | 3 | 4 | 5.13 | 47038 | traffick | — |
| FYN | 1101768 | Q62844 | 3 | — | 6.23 | 60702 | signaling | myristate |
| G protein beta 1 subunit | 31669 | P04901 | 10 | — | 5.60 | 37377 | signaling | — |
| G protein beta 2 subunit | 1738215 | P54313 | 6 | — | 5.61 | 37500 | signaling | — |
| G protein G alpha 11 | 8925964 | Q9JID2 | 10 | 2 | 5.91 | 42026 | signaling | palmitate |
| G protein G alpha 13 | 27690213 | X | 4 | 3 | 8.38 | 43811 | signaling | palmitate |
| G protein Gi alpha 2 | 71896 | P04897 | 7 | 3 | 5.28 | 40368 | signaling | palmitate |
| G protein Gi alpha 3 | 6980964 | P08753 | 6 | 1 | 5.51 | 40391 | signaling | palmitate |
| G protein Go alpha 2 | 27808491 | P30033 | 6 | 3 | 5.62 | 40073 | signaling | palmitate |
| G protein Gq alpha | 7329187 | P82471 | 8 | 3 | 5.58 | 41425 | signaling | palmitate |
| G protein Gs alpha | 14161099 | Q63803 | 6 | 2 | 5.50 | 45709 | signaling | palmitate |
| Giantin | 516826 | Q63714 | 4 | — | 5.01 | 384297 | other | 1 |
| Glut4 | 4193489 | Q9Z1X1 | 4 | 6 | 5.47 | 121159 | transport | 1 |
| High affinity nerve growth factor receptor (TRK-A) | 549122 | P35739 | 4 | — | 5.96 | 87868 | signaling | 1 |
| Integrin alpha-1 (CD49a) | 124941 | P18614 | 8 | 18 | 5.65 | 130809 | adhesion | 1 |
| Integrin alpha-5 (CD49c) | 34868649 | Q80YP5 | 4 | 6 | 5.70 | 115016 | adhesion | 1 |
| Integrin alpha-5 (CD49e) | 13992591 | Q924W2 | 4 | 1 | 6.53 | 108807 | adhesion | 1 |
| Integrin beta-1 (CD29) | 520566 | P49134 | 11 | 10 | 5.77 | 88495 | adhesion | 1 |
| Intercellular adhesion molecule-1 (CD54) | 124100 | Q00238 | 6 | 10 | 6.53 | 60142 | adhesion | 1 |
| Intercellular adhesion molecule-2 | 34873952 | — | 3 | — | 8.02 | 31091 | adhesion | 1 |
| K-Res 2B | 1172844 | P46203 | 3 | 1 | 8.24 | 21425 | signaling | 0 |
| Lipoprotein lipase | 462538 | Q06000 | 3 | — | 6.36 | 53082 | ee | 0 |
| Low-density lipoprotein receptor-related protein 2 | 13562118 | P98158 | 3 | 1 | 5.03 | 519276 | other | 1 |
| Lutheran antigen | 10566957 | Q9ESS6 | 7 | — | 5.52 | 67512 | other | 1 |
| Lyn tyrosine kinase | 2105002 | Q07014 | 13 | — | 6.78 | 58529 | signaling | prenylation |
| Membrane-bound aminopeptidase P | 13560983 | Q99MA2 | 25 | — | 5.49 | 76080 | ee | GPI |
| MHC class I protein, isoform a | 3493247 | X | 3 | — | 6.35 | 39348 | other | 1 |
| MHC class I protein, isoform b (RT1.A1(f) protein) | 1463574 | Q31257 | 15 | 1 | 5.64 | 39246 | other | 1 |
| MHC class I protein, isoform c | 7453015 | X | 5 | — | 7.17 | 41718 | other | 1 |
| MHC class I protein, isoform d | 1263198 | X | 6 | — | 5.55 | 41473 | other | 1 |
| Microsomal depeptidase | 459933 | P31430 | 7 | 2 | 5.67 | 45506 | ee | GPI |
| Myofertin | 23597920 | Q9NZM1 | 9 | 21 | 6.19 | 126162 | other | 1 |
| Na+K+ transporting ATPase alpha-1 | 114376 | P06685 | 20 | 18 | 5.30 | 113054 | transport | 7 |
| Na+K+ transporting ATPase beta-3 | 3121778 | Q63377 | 4 | 2 | 8.08 | 31830 | transport | 1 |
| Neural visinin-like protein 3 | 8393864 | P35333 | 4 | — | 5.32 | 22207 | transport | myristate |
| Nogo-A protein | 8822247 | Q9JK11 | 4 | 5 | 4.41 | 126388 | signaling | 2 |
| OX-2 membrane glycoprotein | 129300 | P04218 | 4 | — | 9.02 | 31088 | other | 1 |
| OX-45 antigen (CD48) | 56805 | P10252 | 9 | — | 7.67 | 27580 | adhesion | GPI |
| P2Z receptor (P2X7) | 2499425 | O64663 | 3 | — | 8.30 | 68392 | signaling | 2 |
| Plasma membrane calcium-transporting ATPase 1 | 92025 | P11505 | 6 | 1 | 5.71 | 138719 | transport | 7 |
| Plasma membrane calcium-transporting ATPase 4 | 1054879 | Q54542 | 5 | — | 6.17 | 133094 | transport | 7 |
| Platelat-endothelial cell adhesion molecule-1 (CD31) | 1684839 | P97635 | 4 | — | 8.63 | 38164 | adhesion | 1 |
| Podocalyxin | 4996222 | Q9WTQ2 | 5 | — | 4.81 | 51545 | adhesion | 1 |
| Progesterons receptor component 1 | 6647578 | P70580 | 4 | 1 | 4.45 | 21467 | signaling | 1 |
| PV-1 | 5281517 | Q9WV78 | 21 | — | 8.80 | 50033 | other | 1 |
| Rab-11B | 9837357 | O35508 | 6 | 3 | 5.98 | 24509 | signaling | prenylation |
| Rab-5b | 27689505 | X | 5 | 2 | 8.64 | 23426 | signaling | prenylation |

TABLE 1-continued

| Protein name | NCBI locus | SwissProt or Trembl locus | Number of MS/MS spectra | | PI | MW | Function | Predicted TMs |
|---|---|---|---|---|---|---|---|---|
| | | | Lung P | RLMVEC | | | | |
| Ral-A | 131836 | P05810 | 4 | 1 | 6.66 | 23553 | signaling | prenylation |
| Ral-B | 310212 | P36660 | 6 | 1 | 6.24 | 23317 | signaling | prenylation |
| Rap-1a | 27650326 | P10113 | 4 | 1 | 6.39 | 20987 | signaling | prenylation |
| Rap-1b | 595280 | Q62636 | 4 | 2 | 5.37 | 20929 | signaling | prenylation |
| Ra5-like protein TC25 | 27662306 | X | 3 | 1 | 9.10 | 16797 | signaling | prenylation |
| Receptor for advanced glycosylaton and products | 498034 | Q63495 | 12 | — | 5.83 | 42684 | signaling | 1 |
| Seven tansmembrane receptor | 5525078 | Q9WVT0 | 4 | — | 6.46 | 149448 | signaling | 7 |
| Tapasin | 13399280 | Q99JC6 | 4 | 1 | 7.74 | 50045 | other | 1 |
| Thrombomodulin | 2502062 | P07204 | 6 | — | 4.78 | 60329 | signaling | 1 |
| TIE-2 | 34869831 | Q9QW24 | 5 | — | 5.94 | 95115 | signaling | 1 |
| Transmembrane 4 superfamily member 3 | 6179618 | O55158 | 5 | — | 5.94 | 25545 | signaling | 4 |
| VAMP-associated protein A | 4240462 | Q9Z270 | 3 | 4 | 8.58 | 27223 | traffick | 1 |
| Vascular endothelial-cadherin | 34851204 | P55284 | 7 | — | 5.12 | 83275 | adhesion | 1 |
| Cytoskeletal and/or junctional proteins | | | | | | | | |
| Actin-alpha | 511131 | P04270 | 29 | 30 | 5.23 | 42019 | structural | |
| Actin-beta | 13592133 | P02570 | 30 | 21 | 5.29 | 41737 | structural | |
| Actin-gamma | 27714843 | X | 9 | 14 | 5.21 | 35162 | structural | |
| Actinin 1-alpha | 4210985 | Q9Z1P2 | 15 | 35 | 5.23 | 102960 | structural | |
| Actinin alpha-4 | 6636119 | Q9QXQ0 | 8 | 19 | 5.24 | 104786 | structural | |
| Adducin, alpha | 1200129 | Q63028 | 9 | 1 | 5.81 | 80355 | structural | |
| Adducin, gamma | 1041240 | Q62847 | 4 | 3 | 6.46 | 78804 | structural | |
| Afadin (I) | 2555011 | Q35889 | 8 | 1 | 5.82 | 207678 | structural | |
| Ankyrin G | 3885972 | X | 3 | 1 | 7.94 | 284459 | other | |
| Catenin alpha | 34878659 | X | 34 | 1 | 5.92 | 105787 | structural | |
| Catenin beta | 16758082 | Q9WU82 | 16 | 1 | 5.63 | 85455 | structural | |
| Catenin delta-1 | 34856482 | X | 18 | 1 | 5.96 | 101396 | structural | |
| Desmin | 1352241 | P48875 | 5 | 8 | 5.21 | 53326 | structural | |
| Desmoplakin I | 34875216 | X | 3 | — | 5.92 | 105787 | structural | |
| Desmuslin | 27676906 | Q810D0 | 3 | — | 5.06 | 140733 | structural | |
| Dynoin, heavy chain | 31377489 | P38650 | 5 | 30 | 6.04 | 532025 | structural | |
| Eplplakin 1 | 34867002 | X | 6 | 3 | 5.65 | 368204 | structural | |
| ERM-binding phosphoprotein | 8132349 | Q9JJ19 | 12 | 1 | 5.70 | 38830 | structural | |
| Ezrin | 17802245 | X | 60 | 21 | 5.59 | 138687 | structural | |
| F-actin capping protein alpha-1 | 34859736 | X | 5 | 3 | 5.43 | 32910 | structural | |
| F-actin capping protein alpha-2 | 34883261 | X | 5 | 3 | 5.57 | 32967 | structural | |
| F-actin capping protein beta | 34872216 | X | 7 | 3 | 5.69 | 30629 | structural | |
| Filamin 1 | 34881882 | X | 61 | 81 | 5.67 | 279442 | structural | |
| Fodrin alpha chain | 3462887 | P16086 | 227 | 109 | 5.20 | 284638 | structural | |
| Gelsolin | 34853856 | X | 9 | 4 | 8.22 | 84948 | structural | |
| Junction plakoglobin | 1497985 | P14923 | 18 | — | 5.95 | 81498 | structural | |
| Kinesin heavy chain 5B | 27687147 | X | 6 | 5 | 6.25 | 97300 | other | |
| Kinesin heavy chain 5C | 34854278 | X | 8 | 3 | 5.99 | 114413 | other | |
| Microlubule-associated protein 1B | 1083718 | X | 5 | 2 | 4.73 | 259025 | structural | |
| Microlubule-associated protein 4 | 34868431 | X | 8 | 7 | 5.29 | 303149 | structural | |
| Moesin | 2218139 | X | 94 | 41 | 5.75 | 206407 | structural | |
| Myosin heavy chain smooth muscle | 82503 | X | 7 | 5 | 5.19 | 47803 | structural | |
| Myosin heavy chain-A, nonmuscle | 967249 | X | 142 | 139 | 5.49 | 226338 | structural | |
| Myosin heavy chain-B, nonmuscle | 7381235 | X | 51 | 112 | 5.49 | 228985 | structural | |
| Myosin I beta | 13431869 | Q05096 | 10 | 4 | 9.42 | 131918 | structural | |
| Myosin I gamma | 23821884 | Q63357 | 4 | 3 | 9.45 | 116137 | structural | |
| Myosin light chain 1 | 56670 | X | 6 | — | 5.03 | 22156 | structural | |
| Myosin light chain 1, atrial | 57513 | X | 8 | 1 | 4.96 | 21252 | structural | |
| Myosin regulatory light chain 2-A, smooth muscle isoform | 57087 | X | 15 | 15 | 4.67 | 19895 | structural | |
| Myosin VI. | 34885321 | X | 5 | — | 8.59 | 116960 | structural | |
| Myosin, unconventional Myr2 I heavy chain | 12831209 | X | 15 | 29 | 9.41 | 118090 | structural | |
| Myotonic dystrophy kinase-related Cdc42-binding kinase beta | 7445380 | O54875 | 11 | 1 | 6.38 | 194020 | signaling | |
| N-WASP | 2274845 | O08816 | 4 | 1 | 8.33 | 54325 | structural | |
| Perlplakin | 34868748 | X | 7 | 1 | 5.35 | 204147 | structural | |
| Plectin | 1709655 | P30427 | 160 | 24 | 5.71 | 533540 | structural | |
| Radixin | 34863387 | X | 60 | 26 | 5.69 | 66125 | structural | |
| Spectrin, beta | 34879632 | X | 137 | 52 | 5.48 | 278423 | structural | |
| Spectrin-like protein GTRAP41 | 11068461 | Q9QWNB | 11 | 1 | 5.59 | 271064 | structural | |
| Tau-blg | 207158 | X | 5 | — | 5.54 | 71774 | other | |
| Tensin | 27684945 | X | 16 | 2 | 6.29 | 64171 | structural | |
| Tight junction protein 1-ZO1 | 34857171 | X | 26 | — | 5.96 | 215532 | structural | |
| Tight junction protein 2-ZO2 | 1839162 | Q9UDY2 | 15 | — | 6.96 | 133972 | structural | |
| Transgelin 2 | 27678408 | X | 3 | 2 | 8.41 | 22393 | other | |
| Tripartite motif protein TRIM2 | 34857890 | X | 3 | — | 6.78 | 90452 | other | |
| Tripartite motif protein TRIM3 | 21362963 | O70277 | 5 | — | 8.17 | 80796 | other | |
| Tropomodulin 1 | 1628561 | P70567 | 4 | — | 4.97 | 40480 | structural | |
| Tropomodulin 2 | 13928838 | P70566 | 3 | — | 5.34 | 39492 | structural | |

TABLE 1-continued

| Protein name | NCBI locus | SwissProt or Trembl locus | Number of MS/MS spectra Lung P | RLMVEC | PI | MW | Function | Predicted TMs |
|---|---|---|---|---|---|---|---|---|
| Tropomodulin 3 | 34864384 | X | 6 | 4 | 4.91 | 46416 | structural | |
| Tropomyosin 2 | 112442 | P04692 | 11 | 5 | 4.71 | 32695 | structural | |
| Tropomyosin 3 | 17105362 | Q63600 | 13 | 4 | 4.68 | 32819 | structural | |
| Tropomyosin 4 | 136081 | P09495 | 7 | 4 | 4.66 | 28510 | structural | |
| Tubulin, alpha-1 | 55777 | X | 14 | 11 | 4.94 | 50136 | structural | |
| Tubulin, Beta 3 | 21245098 | X | 6 | 3 | 4.88 | 50303 | structural | |
| Tubulin, beta-2 | 37494 | P05217 | 22 | 7 | 4.79 | 49831 | structural | |
| Tubulin, beta-5 | 27465535 | P05218 | 25 | 11 | 4.78 | 49640 | structural | |
| Utrophin | 2960013 | X | 16 | 2 | 5.18 | 391075 | structural | |
| Vimentin | 57480 | P31000 | 26 | 42 | 5.06 | 53602 | structural | |
| WASP interacting protein | 12275264 | X | 5 | — | 11.42 | 49751 | structural | |
| Peripherally associated on inside | | | | | | | | |
| Abl-interactor 1 | 13242310 | X | 3 | 1 | 6.57 | 51705 | signaling | |
| Adaptin, alpha A | 113337 | X | 5 | 1 | 6.51 | 104045 | traffick | |
| Adaptin, alpha-C | 90292 | P18484 | 14 | 1 | 6.53 | 103913 | traffick | |
| Adaptin, beta | 18034787 | P21851 | 11 | 1 | 5.19 | 105691 | traffick | |
| Adaptin, beta-3A | 34857415 | X | 3 | 1 | 5.47 | 119142 | traffick | |
| Annexin A11 | 1351943 | P48037 | 6 | — | 5.39 | 75623 | signaling | |
| Annexin A2 | 294518 | Q07936 | 39 | 33 | 7.53 | 38547 | signaling | |
| Annexin A3 | 113955 | P14869 | 4 | — | 6.04 | 36322 | signaling | |
| Annexin A4 | 1703320 | P55260 | 14 | — | 5.32 | 35744 | signaling | |
| Annexin A6 | 763181 | P48037 | 24 | 8 | 5.39 | 75623 | signaling | |
| Arginosuccinase | 31377525 | X | 3 | — | 5.88 | 51391 | ee | |
| Arrestin beta-1 | 203102 | P29068 | 9 | — | 5.84 | 47068 | traffick | |
| Arrestin C | 543855 | P36576 | 3 | — | 5.48 | 9878 | traffick | |
| Beta-adrenergic receptor kinase 1 | 114153 | P26817 | 7 | — | 6.54 | 79785 | signaling | |
| Calgranulin A | 13638435 | P50115 | 4 | — | 5.69 | 10107 | other | |
| Calgranulin B | 476287 | P50116 | 10 | — | 7.24 | 13014 | other | |
| Calmodulin | 230824 | P02593 | 4 | 3 | 4.09 | 16706 | other | |
| Cdc42 guenine nucleolide exchange factor zlzimin 1 | 34876077 | X | 4 | — | 7.44 | 260094 | signaling | |
| Centaurin-alpha2 | 7636039 | Q9JK15 | 4 | — | 9.35 | 43524 | other | |
| Clathrin coal assembly protein AP50 | 113332 | P201727 | 7 | 1 | 9.57 | 49655 | traffick | |
| Cytosolic sorting protein PACS-1a | 3347953 | O88588 | 6 | — | 7.61 | 104700 | traffick | |
| Dynamin II | 729380 | P39052 | 6 | 4 | 6.30 | 44038 | traffick | |
| E3KARP, NHE3 kinase A regulatory protein | 13925523 | X | 24 | — | 5.36 | 84531 | signaling | |
| EBP50-PDZ interactor | 34879000 | X | 4 | 1 | 7.61 | 56788 | other | |
| Exo70 | 2827160 | O54922 | 3 | — | 6.27 | 75046 | traffick | |
| Exocyst complex component Sec3 | 27694722 | X | 3 | 1 | 6.93 | 84552 | traffick | |
| Exocyst complex component Sec5 | 19705549 | O54921 | 4 | 3 | 6.67 | 104031 | traffick | |
| G-protein-coupled receptor kinase 5 | 2499683 | Q62833 | 4 | — | 8.48 | 67783 | signaling | |
| Granzyme K | 1708036 | P49864 | 4 | — | 9.69 | 28465 | signaling | |
| Growth-arrest-specific protein 7 | 25742641 | x | 4 | 2 | 7.24 | 50394 | other | |
| GTPase activating protein 1 | 34837388 | X | 25 | 3 | 6.13 | 193859 | signaling | |
| Hesl shock cognate 71 kDa protein (HSC73) | 58379 | P08109 | 13 | 2 | 5.37 | 70871 | other | |
| Hic-5/ARA55 protein | 12659068 | Q99PD6 | 3 | — | 8.36 | 36181 | other | |
| Integrin-linked kinase | 13111653 | O55222 | 24 | 5 | 8.30 | 51373 | signaling | |
| Janus protein tyrosine kinase 1 | 2288925 | O35803 | 3 | — | 8.28 | 99649 | signaling | |
| Latent TGF-bete binding protein-2 like protein | 2463409 | O35805 | 3 | 12 | 5.20 | 189867 | structural | |
| Lim protein 1 (FHL-1) | 4894849 | Q9WUH4 | 3 | 1 | 8.76 | 31904 | other | |
| Methioine aminopeptidase 2 | 204004 | P38062 | 7 | — | 5.72 | 53052 | ee | |
| Munc18-3 | 12583689 | Q99PV2 | 3 | — | 8.28 | 68021 | transport | |
| Neurofibromin 2 | 32363191 | Q63648 | 3 | 1 | 6.20 | 68712 | structural | |
| Numb protein isoform | 34867377 | x | 7 | — | 9.32 | 69246 | other | |
| Parvin-alpha | 13526899 | Q9HB97 | 5 | 2 | 5.69 | 42292 | structural | |
| Parvin-beta | 34867494 | x | 3 | — | 5.90 | 41701 | structural | |
| Peptide N-myristoyltransferase 1 | 22507314 | x | 7 | 1 | 9.14 | 56937 | other | |
| Periaxin | 18642399 | Q63425 | 28 | 1 | 8.60 | 148400 | other | |
| Paroxiredoxin 4 | 4336879 | Q9Z0V5 | 3 | 1 | 5.86 | 30540 | other | |
| Phosphatidylinositol 4-kinase, 230 kDa | 1944499 | O08562 | 3 | — | 6.57 | 231320 | signaling | |
| Phosphatidylinositol-4-phosphate 5-kinase type II alpha | 16758974 | Q9R018 | 5 | — | 6.50 | 46225 | signaling | |
| Phosphatidylinositol-4-phosphate 5-kinase type II beta | 16758316 | O88377 | 5 | — | 7.18 | 47264 | signaling | |
| Phosphatidylinositol-4-phosphate 5-kinase type II gamma | 17978457 | O88370 | 4 | 1 | 6.39 | 47336 | signaling | |
| Phosphatidylinositol-binding clathrin assembly protein | 16758324 | O55012 | 4 | 2 | 8.58 | 69286 | traffick | |
| Phospholipase C-beta-1 | 91696 | P10687 | 10 | 1 | 5.86 | 138344 | signaling | |
| Phospholipase C-beta-3 | 13177635 | P51432 | 21 | 1 | 5.77 | 139492 | signaling | |
| Phospholipase C-beta-4 | 435757 | Q9QW07 | 13 | 1 | 6.41 | 134497 | signaling | |
| Phospholipase C-beta-4B | 4063009 | x | 10 | 1 | 6.11 | 116040 | signaling | |
| Phospholipase C-gamma-2 | 130230 | P24135 | 4 | — | 6.40 | 147735 | signaling | |
| Pincher | 20135683 | Q8R3Z7 | 19 | 2 | 6.33 | 61468 | traffick | |

TABLE 1-continued

| Protein name | NCBI locus | SwissProt or Trembl locus | Number of MS/MS spectra | | PI | MW | Function | Predicted TMs |
|---|---|---|---|---|---|---|---|---|
| | | | Lung P | RLMVEC | | | | |
| Prohibitin | 13937353 | x | 3 | 11 | 5.57 | 29820 | other | |
| Protein rich synapse associated protein 2 | 5262748 | Q9JLU4 | 13 | 2 | 8.98 | 193258 | traffick | |
| Protein kinase A anchoring protein 2 | 34888424 | x | 9 | — | 4.88 | 90962 | signaling | |
| Protein kinase C delta binding protein | 4092842 | x | 8 | 5 | 5.79 | 27910 | signaling | |
| Protein tyrosine phosphatase, non-receptor type 6 | 16758788 | P81718 | 8 | — | 7.63 | 69578 | signaling | |
| Protein-tyrosine phosphatase, non-receptor type 6 | 16758788 | x | 9 | — | 7.63 | 69578 | signaling | |
| Rai simlan leukemis viral oncogens homolog A2 | 29741807 | x | 3 | — | 9.34 | 24325 | signaling | |
| Ras suppressor protein 1 | 34877253 | x | 18 | 5 | 5.34 | 347557 | signaling | |
| Ras-binding protein SUR-B | 27685625 | x | 4 | — | 9.19 | 32823 | signaling | |
| Rho- and Ari-GTPase activating protein 1 | 27682975 | x | 6 | — | 5.68 | 235892 | signaling | |
| Rho GTPase activating protein 5 | 34865207 | x | 4 | 1 | 6.15 | 172287 | signaling | |
| RhoGEF glutamate transport modulator GTRAP48 | 13027442 | x | 3 | — | 5.50 | 168534 | signaling | |
| Rho-Interacting protein 3 | 10803059 | Q9ERE6 | 7 | 13 | 5.95 | 117113 | signaling | |
| Scaffolding protein SLIPR | 7650497 | x | 5 | — | 5.80 | 129405 | other | |
| Seplin 2 | 13928415 | x | 14 | 16 | 6.15 | 41593 | structural | |
| Seplin 4 | 34872968 | x | 7 | — | 5.81 | 53083 | structural | |
| Seplin 7 (CDC10) | 978915 | Q9WVC0 | 20 | 15 | 8.82 | 50508 | structural | |
| Seplin-like protein | 28849875 | Q9QZR6 | 3 | 2 | 8.65 | 63792 | structural | |
| Serine proteinase inhibitor 3 | 111807 | P09006 | 3 | — | 5.32 | 46652 | other | |
| Serine/threonine kinase 10 | 9507151 | x | 5 | — | 9.44 | 57390 | signaling | |
| Serine/threonine kinase MARK2 | 2052191 | O08679 | 3 | — | 9.63 | 80872 | signaling | |
| Serine/threonine protein kinase TAO1 | 7514084 | O88664 | 3 | — | 7.30 | 115952 | signaling | |
| Serine/threonine protein phosphatase PP1 M110 subunit | 802105 | x | 4 | — | 5.30 | 109720 | signaling | |
| Serine/threonine protein phosphatase PP1B | 585712 | P37140 | 4 | 4 | 5.84 | 37187 | signaling | |
| Serum deprivation response | 34875838 | x | 12 | 2 | 5.21 | 46386 | signaling | |
| Smad1 | 3192871 | P97588 | 3 | — | 6.90 | 52713 | signaling | |
| SNAP-23 | 2970673 | Q70377 | 5 | 3 | 4.82 | 23235 | traffick | |
| Sodium-hydrogen exchanger 3 regulatory factor 1 | 11024674 | x | 7 | — | 5.70 | 38830 | signaling | |
| Sodium-hydrogen exchanger 3 regulatory factor 2 | 15419607 | x | 23 | — | 7.25 | 37369 | signaling | |
| Syndapin 2 | 6651167 | Q9QY17 | 12 | — | 5.04 | 55978 | traffick | |
| Thioredoxin-dependent peroxide reductase 2 | 2499470 | Q63716 | 7 | 4 | 8.27 | 22109 | other | |
| Thrombospondin 1 | 33340123 | AAQ14549 | 4 | 9 | 4.74 | 129671 | adhesion | |
| TOAD-64 | 1351260 | P47942 | 3 | 9 | 5.95 | 62278 | other | |
| TPR-containing Rab8b-interacting protein | 27465633 | Q925N3 | 3 | — | 5.12 | 64885 | other | |
| Ubiquttin | 20302085 | x | 4 | 5 | 6.94 | 34381 | other | |
| Outside bound - secreted/blood | | | | | | | | |
| Apolipoprotein A-I | 91984 | P04639 | 3 | — | 5.52 | 30088 | other | |
| Beta-2-microglobulin | 999882 | P07151 | 4 | — | 7.80 | 13720 | other | |
| Fetuin | 112459 | P24090 | 5 | — | 6.05 | 37982 | other | |
| Fibrinogen B, beta chain | 455105 | P14480 | 6 | — | 7.89 | 54303 | other | |
| Fibronectin | 120178 | P04937 | 3 | 117 | 5.50 | 272511 | other | |
| Glutathione peroxidase | 121658 | P04041 | 7 | 2 | 7.65 | 22258 | other | |
| Hemoglobin, alpha chain | 1304381 | P01945 | 12 | — | 7.93 | 15197 | other | |
| Hemoglobin, beta chain | 204570 | P02091 | 5 | — | 7.99 | 15848 | other | |
| Hepatoma-derived growth factor related protein 3 | 21955178 | Q9D2M7 | 6 | — | 8.4 | 22447 | other | |
| Histidine-rich glycoprotein 1 | 13358876 | X | 13 | — | 7.76 | 59049 | other | |
| Histidine-rich glycoprotein 2 | 13358878 | X | 14 | — | 7.55 | 58056 | other | |
| Inter-alpha-inhibitor H4P heavy chain | 7441758 | O35802 | 4 | — | 6.08 | 103607 | other | 1 |
| Laminin alpha-5 | 34860912 | X | 3 | 6 | 6.21 | 415488 | other | |
| Laminin beta-1 | 27717157 | X | 3 | 2 | 4.82 | 21738 | other | |
| Laminin gamma-1 | 27712576 | P11047 | 3 | 3 | 5.20 | 167423 | other | |
| Mast cell protease 8 | 8928167 | P97594 | 6 | — | 9.02 | 27488 | other | |
| Mast cell protease 9 (Grenzyme J) | 1763232 | P97595 | 6 | — | 9.33 | 26314 | other | |
| Prolargin | 10834558 | Q9EQP5 | 15 | 1 | 9.51 | 43179 | other | |
| Serum albumin | 55628 | P02770 | 15 | 1 | 6.09 | 68719 | other | |
| Spondin | 544353 | P35446 | 7 | — | 5.85 | 90773 | other | |
| Transferrin | 1854476 | P12346 | 7 | 1 | 6.94 | 76364 | other | |
| Vitronectin | 1255044 | Q62905 | 6 | — | 5.68 | 54679 | other | |
| Von Willebrand factor | 4467984 | P04275 | 12 | — | 5.32 | 309299 | other | |
| Poorly characterized proteins (unknown localization, structure, and function) | | | | | | | | |
| Ac2.233 | 32527749 | Q7TPJ1 | 3 | — | 6.16 | 161633 | | |
| Brain-enriched WD-repeat protein | 13560779 | X | 6 | — | 6.74 | 57551 | | |
| cDNA Sequence BC019977 | 34871032 | X | 3 | — | 9.99 | 90565 | | |
| DAMP-1 protein | 28070980 | Q811A2 | 4 | — | 8.38 | 19674 | | 2 |

TABLE 1-continued

| Protein name | NCBI locus | SwissProt or Trembl locus | Number of MS/MS spectra | | PI | MW | Function | Predicted TMs |
| --- | --- | --- | --- | --- | --- | --- | --- | --- |
| | | | Lung P | RLMVEC | | | | |
| EH-domain containing protein 2 | 34452241 | Q8R491 | 5 | 2 | 5.95 | 61106 | | |
| EH-domain containing protein 3 | 34536836 | X | 6 | 2 | 6.04 | 60807 | | |
| Granzyme-like protein II | 296176 | Q06606 | 7 | — | 8.74 | 27463 | | |
| Hypothetical protein FLJ10849 | 34876531 | X | 18 | 20 | 6.47 | 58774 | | |
| Hypothetical protein FLJ13187 | 34866158 | X | 3 | — | 8.55 | 27741 | | |
| Hypothetical protein FLJ20401 | 34856089 | X | 6 | — | 7.62 | 98851 | | |
| Hypothetical protein FLJ30973 | 34864323 | X | 4 | — | 5.55 | 61017 | | |
| Hypothetical protein KIAA0332 | 27721099 | X | 3 | — | 7.32 | 110303 | | |
| Hypothetical protein KIAA0635 | 27694697 | X | 3 | 2 | 5.66 | 55620 | | |
| Hypothetical protein KIAA0783 | 27712638 | X | 3 | 1 | 8.86 | 139934 | | |
| Hypothetical protein KIAA0915 | 27672832 | X | 8 | — | 8.66 | 91406 | | |
| Hypotheticel protein KIAA0982 | 27688091 | X | 4 | — | 5.69 | 57127 | | |
| Hypotheticel protein KIAA1902 | 27699143 | X | 3 | — | 6.16 | 89929 | | |
| Hypothetical protein XP_238419 | 27716235 | X | 4 | 1 | 10.00 | 9379 | | |
| Hypothetical RNA binding protein RDA288 | 18041977 | X | 6 | 16 | 8.42 | 43012 | | |
| Similar to KIAA1185 protein | 34872773 | X | 6 | 1 | 8.52 | 63531 | | |
| Lethel glant larvae-like protein 1 homolog | 22779849 | X | 3 | — | 6.14 | 112495 | | |
| Neuronel tissue-enriched acidic protein | 11560135 | X | 3 | 5 | 4.50 | 21790 | | |
| Protein kinase SK2 | 7514055 | X | 12 | 1 | 4.96 | 137888 | | |
| RIKEN cDNA 2010012F05 | 34859075 | X | 3 | 2 | 4.80 | 23760 | | |
| Similar to a C.elegans protein RW1 | 34875601 | X | 3 | 1 | 7.24 | 190311 | | 2 |
| Similar to actin binding protein-278 | 34869526 | X | 23 | 30 | 5.41 | 284704 | | |
| Similar to Brain-Specific Protein p25 Alpha | 27729783 | X | 3 | — | 9.71 | 54772 | | |
| Similar to BUB3 | 34859446 | X | 12 | — | 6.32 | 30535 | | |
| Similar to cask-interacting Protein 2 | 34875360 | X | 4 | — | 6.58 | 127726 | | |
| Similar to CGI-74 protein | 34855164 | X | 3 | — | 11.56 | 26564 | | |
| Similar to chromodomain-helicase-DNA-binding protein 5 | 34860336 | X | 3 | 5 | 5.74 | 301239 | | |
| Similar to cleavage and polyadenylation specfic factor 6 | 34664893 | X | 4 | 1 | 9.14 | 69006 | | |
| Similar to cobi-related protein 1 | 34854739 | X | 3 | — | 6.39 | 135108 | | |
| Similar to cytochrome b5 Reductase 1 | 27712062 | X | 3 | 1 | 8.95 | 34233 | | |
| Similar to DEAD-box protein 05 | 27690065 | X | 14 | 6 | 9.06 | 69239 | | |
| Similar to DEAD-box protein 17 | 34866944 | X | 8 | 5 | 8.75 | 73945 | | |
| Similar to DEAH-box protein 15 | 34878065 | X | 4 | 1 | 7.12 | 90977 | | |
| Similar to dJ1033H22.1 (KIAA0554) | 34860217 | X | 9 | — | 6.40 | 68740 | | |
| Similar to DNA-PKcs | 34870011 | X | 3 | 1 | 6.90 | 470420 | | |
| Similar to DOCK180 protein | 34874363 | X | 4 | — | 7.15 | 218571 | | |
| Similar to DRIM (downregulated in metastasis) protein | 27717947 | X | 3 | 1 | 8.59 | 289353 | | |
| Similar to ELMO1 | 34676187 | X | 6 | — | 5.86. | 44456 | | |
| Similar to ELMO2 (KIAA1834) | 34860711 | X | 3 | — | 5.91 | 66108 | | |
| Similar to eukaryotic translation initiation factor 5A | 27672956 | Q8VHU8 | 5 | 6 | 5.07 | 16832 | | |
| Similar to fibrillarin | 34855407 | X | 3 | 10 | 10.25 | 34222 | | |
| Similar to FK506 binding protein 3 | 27684664 | X | 5 | 2 | 9.29 | 25148 | | |
| Similar to FSHD region gene 1 protein | 34872381 | X | 6 | — | 8.95 | 29031 | | |
| Similar to Hbs1) protein | 34852621 | X | 3 | — | 9.17 | 47772 | | |
| Similar to heat shock 70 kDa protein 12A (HSPA12A) | 34864793 | X | 3 | 1 | 8.87 | 129368 | | |
| Similar to heat shock 70 kDa protein 12B (HSPA12B) | 34858716 | X | 25 | — | 8.58 | 81822 | | |
| Similar to HSPC315 | 34871854 | X | 3 | — | 6.37 | 28146 | | |
| Similar to hypothetical protein | 27710240 | X | 6 | — | 8.47 | 77072 | | |
| Similar to hypothetical protein MGC29390 | 34869210 | X | 3 | 1 | 6.53 | 202867 | | |
| Similar to integrin alpha-L | 34859294 | X | 5 | — | 6.15 | 151135 | | |
| Similar to KIAA1083 protein | 34662486 | X | 3 | — | 9.61 | 69002 | | |
| Similar to KIAA1230 protein | 27713641 | X | 3 | — | 5.43 | 111708 | | 1 |
| Similar to KIAA1849 protein | 27731437 | X | 8 | — | 11.27 | 18939 | | |
| Similar to LD39815p | 27716313 | X | 3 | 1 | 6.23 | 29077 | | |
| Similar to leiomodin 1 | 34880269 | X | 3 | — | 9.27 | 62197 | | |
| Similar to Map4k6-pending protein | 34871056 | X | 4 | — | 8.00 | 56056 | | |
| Similar to mBLVR | 34862268 | X | 4 | — | 8.11 | 81993 | | |
| Similar to mitochondrial import receptor subunit TOM34 | 34850656 | X | 3 | — | 9.23 | 34461 | | |
| Similar to mKIA0219 | 34872627 | Q92616 | 4 | 7 | 7.36 | 303089 | | |
| Similar to myeloperoxidase | 34873270 | X | 3 | — | 9.61 | 80683 | | |
| Similar to Na$^+$ and H$^+$-coupled glutamine transporter | 16923996 | Q8VEK3 | 9 | 16 | 5.92 | 87748 | | 0 |
| Similar to nebulin | 34854661 | X | 3 | 1 | 9.08 | 909311 | | |
| Similar to nicotinamide nucleotide transhydrogenase | 34854180 | Q13423 | 3 | 9 | 9.17 | 34922 | | 12 |
| Similar to nuclear receptor coactivator NCoA-62 | 34867492 | X | 3 | 2 | 9.00 | 145690 | | |
| Similar to OSBP-ratated protein 6 | 34856448 | X | 3 | — | 6.63 | 105187 | | |

TABLE 1-continued

| Protein name | NCBI locus | SwissProt or Trembl locus | Number of MS/MS spectra Lung P | RLMVEC | PI | MW | Function | Predicted TMs |
|---|---|---|---|---|---|---|---|---|
| Similar to osmotic stress protein | 34856875 | X | 3 | 3 | 9.91 | 35022 | | 2 |
| Similar to p53 inducible protein | 34870680 | X | 7 | — | 8.10 | 127654 | | |
| Similar to polymerase i-transcript release factor | 27689507 | X | 25 | 5 | 5.43 | 43909 | | |
| Similar to pre-mRNA cleavage factor im (25 kD) | 12655103 | X | 13 | 3 | 8.85 | 26227 | | |
| Similar to protein disulfide isomerase A5 | 34869214 | X | 3 | — | 6.35 | 89317 | | |
| Similar to protein disulfide isomerase-related protein | 34869214 | X | 4 | 2 | 6.35 | 89317 | | |
| Similar to PTB-associated splicing factor | 34871066 | X | 6 | 10 | 8.94 | 65137 | | |
| Similar to PTPL1-associated RhoGAP 1 | 34862742 | X | 6 | — | 5.83 | 128868 | | |
| Similar to Rab8-Interacting Protein | 34861506 | X | 3 | — | 6.06 | 91387 | | |
| Similar to rho/rac guenine nucleotide exchange factor.GEF | 27693092 | X | 4 | — | 5.39 | 72437 | | |
| Similar to ribosome binding protein 1 | 34858829 | X | 8 | 9 | 9.00 | 143328 | | |
| Similar to RIKEN cDNA 1190003A07 | 34861128 | X | 3 | 1 | 5.46 | 156956 | | |
| Similar to RIKEN cDNA 1500019M23 | 34932774 | X | 3 | 2 | 8.99 | 20550 | | |
| Similar to RIKEN cDNA 1810013P09 | 34855823 | X | 3 | — | 8.66 | 38164 | | |
| Similar to RIKEN cDNA 3010001A07 | 34868074 | X | 4 | 1 | 8.92 | 82148 | | 2 |
| Similar to RNA helicase (DEAD-box protein 03) | 34933204 | X | 7 | 13 | 6.18 | 69437 | | |
| Similar to Schwachmen-Bodian-Diamond syndrome protein | 27664348 | X | 4 | 1 | 8.91 | 28753 | | |
| Similar to selective hybridizing ctone (SHYC) | 34856144 | X | 9 | — | 6.89 | 164053 | | |
| Similar to SET binding factor 1 | 34867569 | X | 3 | 1 | 8.41 | 198456 | | |
| Similar to slingshot 1 | 34872828 | X | 4 | 1 | 6.36 | 178058 | | |
| Similar to small nuclear ribonucleoprotein associated protein N | 27687269 | Q63747 | 8 | 3 | 11.31 | 124746 | | |
| Similar to small nuclear ribonucleoprotein Sm D2 | 27676406 | X | 3 | 3 | 9.92 | 13527 | | |
| Similar to small nuclear ribonucleoprotein Sm D2 | 27676406 | X | 3 | 3 | 9.92 | 13527 | | |
| Similar to small nuclear ribonucleoprotein U1A | 34855379 | X | 4 | — | 6.40 | 15295 | | |
| Similar to splicing factor (CC1.3) | 34860256 | X | 4 | — | 10.23 | 68157 | | |
| Similar to splicing factor PRP8 | 34872765 | X | 3 | — | 8.86 | 304438 | | |
| Similar to splicing factor SC35 | 27691222 | X | 3 | — | 11.86 | 25476 | | |
| Similar to splicing factor U2AF 65 kDa subunit | 34854490 | X | 9 | — | 4.98 | 28114 | | |
| Similar to sulfide quinone reductase | 34856819 | X | 5 | 5 | 9.02 | 69000 | | |
| Similar to SWI/SNF complex 170 kDa subunit | 34882210 | X | 5 | 2 | 5.28 | 126799 | | |
| Similar to talin 2 | 34884297 | X | 77 | 37 | 5.47 | 284529 | | |
| Similar to Tenc1 protein | 34868685 | X | 3 | — | 8.53 | 164794 | | |
| Similar to TMP 2 | 34862084 | X | 3 | — | 7.73 | 163993 | | 1 |
| Similar to transcription factor BTF3 | 27686915 | X | 8 | 3 | 6.85 | 17699 | | |
| Similar to transcription factor CA150 | 34878270 | X | 10 | — | 8.80 | 123020 | | 2 |
| Similar to transcription Initiation Factor IIE, Alpha Subunit | 27666810 | X | 3 | 1 | 4.72 | 49229 | | |
| Similar to transcription termination factor I interacting peptide 20 | 34854655 | X | 3 | — | 8.69 | 42723 | | |
| Similar to transcriptional activator Pur-alpha | 34878562 | X | 4 | 2 | 6.07 | 34884 | | |
| Similar to tyrosyl-tRNA ligase | 34871588 | X | 7 | 1 | 8.61 | 63026 | | |
| Similar to U2 small nuclear ribonuclaoprotein B | 34858820 | X | 3 | — | 9.72 | 25352 | | |
| Similar to vinculin | 34868946 | X | 12 | 7 | 5.52 | 135513 | | |
| Similar to WD repeat endosomal protein | 34856638 | X | 3 | — | 7.05 | 84698 | | |
| Similar to Warner syndrome helicase homolog | 34878743 | X | 3 | — | 5.31 | 99948 | | |
| Similar to zinc finger protein Cazanne | 34858073 | X | 3 | 2 | 6.85 | 150318 | | |
| Similar to zinc finger transcription factor ZNF207 | 34872895 | X | 4 | — | 9.20 | 52779 | | |
| TEMO (novel testicular molecule) | 9954445 | Q9ESY1 | 3 | — | 6.71 | 206589 | | |
| Thyroid hormone receptor interactor 10 (salt tolerant protein) | 16758800 | P97531 | 4 | 3 | 5.23 | 62788 | | |
| Ribosomal proteins | | | | | | | | |
| ABC50 | 10863747 | Q9ERQ2 | 4 | — | 6.79 | 92749 | | |
| Acidic ribosomal phosphoprotein PO | 11693176 | P19945 | 4 | — | 5.91 | 34215 | | |
| Elongation factor 1-alpha 1 | 1220484 | Q64718 | 31 | 20 | 9.10 | 50150 | | |
| Elongation factor 1-alpha 2 | 206440 | P27706 | 5 | 1 | 9.11 | 50454 | | |

TABLE 1-continued

| Protein name | NCBI locus | SwissProt or Trembl locus | Number of MS/MS spectra | | PI | MW | Function | Predicted TMs |
|---|---|---|---|---|---|---|---|---|
| | | | Lung P | RLMVEC | | | | |
| Eukaryolic translation Initiation factor 1, alpha subunit | 1352425 | P47813 | 3 | — | 4.91 | 46416 | | |
| Eukaryolic translation Initiation factor 2, alpha subunit | 325 | P05199 | 9 | 2 | 5.02 | 35977 | | |
| Eukaryolic translation Initiation factor 2, beta subunit | 27703942 | X | 7 | 1 | 5.61 | 35243 | | |
| Eukaryolic translation Initiation factor 2, gamma subunit | 27663888 | X | 10 | 3 | 9.51 | 17740 | | |
| Eukaryolic translation Initiation factor 5 | 585303 | Q07205 | 5 | 1 | 5.36 | 48954 | | |
| Ribosomal proteins large subunit family | X | X | X | X | basic | X | | |
| Ribosomal proteins small subunit family | X | X | X | X | basic | X | | |
| Ribosomal S6 kinase alpha 1 | 13592065 | Q63531 | 3 | — | 7.97 | 82883 | | |
| Endoplasmic reticulum proteins | | | | | | | | |
| 78 KD Glucose-regulated protein | 121574 | P06761 | 10 | 50 | 5.07 | 72347 | | |
| Calnexin | 543922 | P35565 | 7 | 23 | 4.49 | 67255 | | 1 |
| Calraliculin | 55855 | P18418 | 10 | 15 | 4.33 | 47995 | | |
| Cytochrome b5, ER | 231928 | P00173 | 3 | 1 | 4.90 | 15224 | | |
| Cytochrome P450 2B1 | 223633 | P00176 | 3 | — | 7.00 | 55934 | | 1 |
| Flavin-containing monooxygenase 1 | 204192 | P36385 | 5 | — | 8.68 | 59761 | | 1 |
| Heat shock protein 47 kDa | 8393057 | P29457 | 6 | 15 | 8.68 | 46518 | | |
| NADH-cytochrome b5 reductase | 127847 | P20070 | 7 | 3 | 8.57 | 34043 | | |
| NADPH-cytochrome P450 reductase | 3318958 | P00388 | 5 | 5 | 5.30 | 76832 | | 1 |
| Peptidyl-protyl cis-trans isomerase B | 2143900 | P24368 | 19 | 15 | 9.30 | 23025 | | |
| Prostaglandin F2 receptor negative regulator | 2497303 | Q62788 | 3 | 1 | 6.16 | 98731 | | 1 |
| Protein disulfide isomerase A3 | 56905 | P11598 | 21 | 36 | 5.88 | 56623 | | |
| Protein disulfide isomerase A6 | 2501206 | Q63081 | 3 | 15 | 4.95 | 47220 | | |
| Ribophorin I | 132560 | P07153 | 4 | 16 | 6.05 | 68304 | | 1 |
| Ribophorin II | 132552 | P25235 | 4 | 5 | 5.72 | 68081 | | 3 |
| Mitochondrial proteins | | | | | | | | |
| Acetoacelyl-CoA thiolase | 135757 | P17764 | 4 | 3 | 8.92 | 44695 | | |
| Acetyl-CoA scyltransferase | 135762 | P13437 | 3 | 3 | 8.09 | 41871 | | |
| Aldehyde dehydrogenase, mitochondrial | 118505 | P11884 | 3 | 4 | 6.53 | 58488 | | |
| ATP synthase CF(0) - B chain, mitochondrial | 114625 | P19511 | 3 | 6 | 9.39 | 28869 | | |
| ATP synthase CF(0) - D chain, mitochondrial | 220904 | P31399 | 4 | 8 | 6.21 | 18632 | | |
| ATP synthase CF(1) - alpha chain, mitochondrial | 6729934 | P15999 | 14 | 22 | 9.22 | 58826 | | |
| ATP synthase CF(1) - beta chain, mitochondrial | 1374715 | P10719 | 17 | 23 | 5.18 | 56354 | | |
| Cytochrome b5, mitochondrial | 2253161 | P04166 | 3 | 1 | 4.92 | 16265 | | |
| Cytochrome c, somatic | 118008 | P00009 | 4 | 6 | 9.61 | 11474 | | |
| Gluternate dehydrogenase | 6980856 | P10860 | 12 | 13 | 8.05 | 61428 | | |
| Heat shock 40 kDa protein 4 | 1706475 | P54102 | 4 | 3 | 6.65 | 44868 | | |
| NADP+-specific isocitrate dehydrogenase | 13928690 | X | 4 | 7 | 6.53 | 46734 | | |
| PDC-E2 | 268685 | P08461 | 3 | 3 | 5.70 | 58764 | | |
| Succinyl-CoA synthetase, alpha chain | 135025 | P13086 | 4 | 9 | 9.54 | 35032 | | |
| Trifunctional enzyme, alpha subunit | 510108 | Q64428 | 8 | 14 | 8.11 | 82513 | | |
| Trifunctional enzyme, beta subunit | 543387 | Q60587 | 5 | 3 | 9.50 | 51414 | | |
| Ubiquinol-cylochrome C reductase complex core protein 2 | 418146 | P32551 | 3 | 6 | 9.16 | 48373 | | |
| Nuclear proteins | | | | | | | | |
| 2',3'-cyclic nucleolide 3'-phosphodiesterase | 294527 | Q84575 | 4 | — | 9.03 | 47268 | | |
| Centrosomal protein 2 | 27704348 | Q9BV73 | 3 | 2 | 4.98 | 208800 | | |
| DNA mismatch repair protein Msh2 | 1709122 | P54275 | 3 | 1 | 5.77 | 104028 | | |
| DNA lopoisomerase I | 4809197 | X | 5 | 1 | 9.35 | 90760 | | |
| FBP-interacting repressor | 5524727 | Q9NZA0 | 6 | 1 | 5.25 | 58171 | | |
| G10 protein homolog (edg-2) | 3064070 | O70454 | 6 | — | 9.15 | 17069 | | |
| High mobility group protein 1 | 1708258 | P07155 | 24 | 8 | 5.70 | 24894 | | |
| High mobility group protein 2 | 1708260 | P52925 | 20 | 1 | 7.10 | 24028 | | |
| Histones | X | X | X | X | X | X | | |
| La Ribonucleoprotein | 729919 | P38656 | 4 | 4 | 9.47 | 47777 | | |
| Lamin A | 1348413 | P48679 | 25 | 53 | 6.54 | 74324 | | |
| Lamin B1 | 1575794 | P70615 | 9 | 16 | 5.16 | 66475 | | |
| Lamin C2 | 1556433 | P48679 | 21 | 42 | 6.54 | 74324 | | |
| Nucleolin | 92558 | P13383 | 3 | — | 4.67 | 77016 | | |
| Nucleophosmin | 114763 | P13084 | 3 | 7 | 4.62 | 32560 | | |
| Poly [ADP-ribose] polymerase-1 (PARP-1) | 3123251 | P27008 | 10 | 1 | 9.07 | 112529 | | |
| Pyrimidine binding protein 1 | 13487910 | Q00438 | 3 | 6 | 9.14 | 56937 | | |
| Spliceosomal protein SAP155 | 9885342 | Q9ET34 | 3 | — | 5.67 | 54496 | | |

TABLE 1-continued

| Protein name | NCBI locus | SwissProt or Trembl locus | Number of MS/MS spectra | | PI | MW | Function | Predicted TMs |
|---|---|---|---|---|---|---|---|---|
| | | | Lung P | RLMVEC | | | | |
| Structural maintenance of chromosome 3 | 29336525 | P97690 | 3 | 1 | 7.82 | 138448 | | |
| Thymopoletin beta (LAMINA-associated polypeptide 2) | 6981660 | Q62733 | 4 | 4 | 9.40 | 50278 | | 1 |
| Transcription factor MTSG1 | 30017413 | Q80Z99 | 3 | 1 | 7.20 | 50728 | | |
| Transcription initiation factor RAP30 | 220891 | Q63489 | 5 | 1 | 9.24 | 28380 | | |

All proteins listed are from R. norvegicus and fall within the 95% range of confidence of analytical completeness. To be included, each protein was to have 3 distinguishable MS/MS spectra of true tryptic peptides. Distinguishable MS/MS spectra included spectra of the same peptide with different charge states though none of the proteins reported here were covered by only one peptide with spectra from 3 charge states. Although proteins covered by 3 MS/MS spectra accounted for the largest subpopulation, 70% of all proteins reported here were covered with more than 3 MS/MS spectra. The distribution of MS/MS spectrum coverage followed roughly a single exponential decay in the range of 3 and 12 MS/MS spectra. Exceptions were apparently highly abundant, highly covered proteins, such as fodrin (227 spectra), spectrin (137 spectra) or plectin (160 spectra).

High prevalence of known endothelial cell surface proteins. 73 known vascular endothelial cell surface proteins were identified in rat lung P and RLMVEC P (Table 2).

TABLE 2

Endothelial cell associated marker proteins

| Protein name | NCBI locus | SwissProt or Trembl locus | Species | Number of MS/MS spectra | |
|---|---|---|---|---|---|
| | | | | Rat Lung | RLMVEC |
| 5'-nucleotidase (CD73) | 112826 | P21588 | R | — | 10 |
| alpha-2 macroglobulin | 112914 | P28666 | M | 1 | — |
| Aminopeptidase N (CD13) | 2499898 | P97449 | R | 3 | 4 |
| Angiotensin-converting enzyme (CD134) | 11493661 | P12821 | R | 44 | — |
| Annexin IV | 1703320 | P55260 | R | 14 | — |
| Annexin V | 4033508 | P14668 | R | 2 | 2 |
| APC protein | 114033 | P25054 | H | 2 | — |
| Aquaporin-CHIP | 267413 | P29975 | R | 3 | — |
| Carbonic anhydrase IV | 544726 | P48284 | R | 11 | — |
| Caveolin-1 | 17017233 | Q8VIK9 | R | 13 | 5 |
| Dipeptidyl peptidase IV (CD26) | 118905 | P14740 | R | 31 | — |
| Ecto-apyrase (CD39) | 2499219 | P55772 | M | 1 | — |
| EDG-1 | 1352343 | P48303 | R | 1 | — |
| EDG-2 | 729546 | P41223 | H | 3 | — |
| EGF | 10880036 | X | H | 1 | 1 |
| Endomucin | 34860660 | X | R | 1 | — |
| Endothelial actin-binding protein | 17486458 | P21333 | H | 61 | 81 |
| Endothelial cell-selective adhesion molecule | 13991773 | Q925F2 | M | 5 | — |
| Endothelial collagen | 17738302 | P27658 | H | — | 3 |
| Endothelial differentiation-related factor 1 | 4503453 | O60869 | H | 2 | — |
| Endothelial plasminogen activator inhibitor | 129578 | P20961 | R | 0 | 4 |
| Endothelin converting enzyme | 529085 | P42893 | R | 7 | — |
| H-CAM (CD44) | 19923703 | O08779 | R | 2 | 4 |
| Integrin alpha V | 1170592 | P43406 | M | 2 | 5 |
| Integrin alpha-1 (CD49a) | 124941 | P18614 | R | 8 | 18 |
| Integrin alpha-3 (CD49c) | 3183040 | Q62470 | M | 7 | — |
| Integrin alpha-5 (CD49e) | 1708569 | P11688 | M | 4 | 6 |
| Integrin beta-1 (CD29) | 520566 | P49134 | R | 11 | 10 |
| Intercellular adhesion molecule-1 (CD54) | 124100 | Q00238 | R | 6 | 10 |
| Intercellular adhesion molecule-2 | 462381 | P35330 | M | 3 | — |
| MAC-inhibitor (CD59) | 2507508 | P27274 | R | 1 | — |
| MDR 1A | 266517 | P21447 | R | 1 | 9 |
| MECA32 | 14161394 | X | M | 2 | 1 |
| Microvascular endothelial differentiation gene 1 | 10732861 | P97554 | R | — | 1 |
| MRP-1 (CD9) | 729088 | P40241 | R | 3 | 2 |
| MUC18 | 13095926 | X | R | 5 | — |
| Muscarinic acetylcholine receptor M3 | 92492 | X | R | 1 | 1 |
| Na+K+ transporting ATPase alpha 1 | 18204493 | P06685 | M | 20 | 18 |
| Nitric-oxide synthase | 266646 | P29476 | R | 1 | 1 |
| PAR-1B alpha | 15042611 | X | H | 1 | — |
| Platelet-endothelial cell adhesion molecule-1 (CD31) | 1684839 | X | R | 4 | — |
| Platelet endothelial tetraspan antigen-3 | 11968106 | Q9QZA6 | R | 1 | 3 |
| Platelet-derived growth factor receptor | 129891 | P05622 | M | 1 | 1 |
| Podocalyxin | 4996222 | X | R | 5 | — |
| PV-1 | 5281517 | Q9WV78 | R | 21 | — |
| RAGE | 2497319 | Q63495 | R | 11 | — |

TABLE 2-continued

Endothelial cell associated marker proteins

| Protein name | NCBI locus | SwissProt or Trembl locus | Species | Number of MS/MS spectra Rat Lung | RLMVEC |
|---|---|---|---|---|---|
| Scavenger receptor (CD36) | 3243055 | X | R | 1 | — |
| Scavenger receptor class B type I | 4210542 | X | R | 1 | 1 |
| Scavenger receptor class F | 4507203 | X | H | 1 | — |
| Sialomucin (CD34) | 495716 | Q64314 | M | 1 | — |
| Thrombomodulin | 13929084 | X | R | 6 | — |
| Tight junction protein 1 - ZO1 | 303710 | P39447 | M | 26 | — |
| Tight junction protein 2 - ZO2 | 303710 | P39447 | R | 15 | — |
| Transferrin receptor (CD71) | 136378 | P02786 | H | 2 | 1 |
| Tumor endothelial marker 4 | 15987489 | Q96PFE | H | 2 | — |
| Tumor endothelial marker 6 (Tensin 3) | 17511209 | Q96PE0 | H | 2 | 1 |
| Tyrosine-protein kinase receptor TIE-2 | 34869831 | Q9QW24 | R | 5 | — |
| Vascular adhesion protein-1 | 5902787 | O70423 | M | 2 | — |
| Vascular cell adhesion protein 1 | 267284 | P29534 | R | — | 8 |
| Vascular endothelial cell specific protein 11 | 13926415 | X | R | 14 | 16 |
| Vascular endothelial junction-associated molecule | 10720348 | P57087 | H | 2 | — |
| Vascular endothelial-cadherin 1 | 1150514 | P55284 | M | 7 | — |
| Vascular endothelial-cadherin 2 | 8164037 | Q9NPG4 | H | 2 | 1 |
| Von Willebrand factor | 4467984 | P04275 | R | 12 | — |

Because these proteins are known to be reasonable markers of the endothelial cell surface and thus do not require additional confirmation, the stringency of the criteria for positive identification was lowered to 1 true tryptic peptide MS/MS spectrum plus verification of the high quality of the single spectra by manual inspection. Of the 65 endothelial cell marker proteins identified in rat lung P, 43 had >1 MS/MS spectra and 41 were solely identified in rat lung P. In RLMVEC P, 32 marker proteins were found, of which 8 were not identified in lung P. One could increase the number of identified endothelial cell-associated proteins greatly by adding all the cytoskeletal proteins identified and known to exist in endothelial cells.

Comparison of endothelial cell surface proteins in vivo vs. in vitro. To assess protein expression of endothelial cells growing under native conditions in vivo vs. under cell culture conditions in vitro, proteins in P of RLMVEC vs. rat lung were compared. A minimum coverage was allowed of one MS/MS spectrum per protein for proteins identified in RLMVEC P as long as the protein had been identified previously with higher stringency (>3 spectra) in rat lung P. 263 out of the 450 proteins identified in rat lung P were also found in RLMVEC P with the remaining 187 proteins detected only in rat lung P, suggesting possible modulation by the unique tissue microenvironment found in vivo but not yet reproduced in cell culture. 55.5% of the proteins identified in RLMVEC P were identified with 3 or more MS/MS spectra. If the same 3 peptide criteria were used as for rat lung P, then only 32.2% (145 of 450 proteins) overlapped with RLMVEC P. Even greater differences were also apparent in select categories of proteins. About 50% of the integral and peripheral membrane proteins as well as yet-to-be-characterized proteins were solely identified in rat lung P. Only 35% of the blood and secreted proteins externally bound to the membranes from rat lung P were detected in RLMVEC P. Consistent with cultured endothelial cells expressing >10-fold less caveolae relative to native endothelial cells in vivo, we identified in RLMVEC P only about 30% of the trafficking proteins found in rat lung P. Cytoskeletal proteins as well as proteins primarily located in mitochondria, ER, and nuclei were found in similar proportions in RLMVEC P and rat lung P.

MS/MS spectrum coverage of proteins by category. Cytoskeletal proteins had the best MS/MS spectrum coverage in our sample (23.6 spectra/protein) followed by inner peripheral membrane associated proteins (8.9 spectra/protein) whereas transmembrane spanning and lipid anchored proteins had significantly less (both with 6.9 spectra/protein). Hydrophobic integral membrane proteins, especially multispanners, have fewer tryptic cleavage sites (hydrophilic residues R and K) and are frequently glycosylated which may prevent access for the protease, reducing the number of possible tryptic peptide derivatives identified resulting in decreased spectrum coverage to very low levels. For example, based on a calculation of theoretical tryptic digests, G-protein coupled receptors (with 7 transmembrane (TM) domains) have large, membrane-embedded hydrophobic portions that complicate the analysis because, unlike most proteins which provide an average of 6 tryptic peptides/10 kDa of protein mass (determined for bovine serum albumin), the 7 TM proteins have only 1.25 tryptic peptides/10 kDa with properties likely to produce good MS/MS spectra (based on an evaluation of 2-adrenergic receptor, 1B adrenergic receptor, muscarinic receptor M1, B1 bradykinin receptor, and angiotensin II receptor 1A). We identified 19 G protein coupled receptors (with 7 transmembrane domains) in lung P, but only with 1 or 2 spectra, well below our stringent criteria of >3 spectra for positive identification. Therefore, the relative abundance of membrane proteins in the sample may be higher.

Western analysis of selected proteins. To validate the proteins identified in rat lung P or RLMVEC P, Western analysis was performed on a subset of 23 proteins (chosen relatively randomly based on availability of antibodies). Out of the 23 proteins analyzed, 16 were found by mass spectrometry (MS) to be present in rat lung P, but not in RLMVEC P (e.g. ACE and endothelin converting enzyme (ECE)). This finding was confirmed by Western analysis in 14 out of the 16 cases (87.5%). Only high affinity nerve growth factor receptor (Trk-A) and Lyn B were detected by Western analysis but not by MS in RLMVEC P. Nine proteins not detected in RLMVEC P were known endothelial cell markers (ACE, aquaporin, carbonic anhydrase (CA), ECE, podocalyxin, receptor for advanced glycation end product (RAGE), zona occludens (ZO)-2, TIE-2, VE-cadherin) and 4 of the remaining 7 proteins had either a predicted transmembrane domain (Trk-A, P2Z receptor, seven transmembrane receptor) or a lipid anchor (LynB), suggesting plasma membrane localization. All 5 proteins (APN, caveolin-1, HSP47, FLJ10849, and ICAM-1) that were identified by MS in both rat lung P and in RLMVEC P were confirmed by Western analysis. 5'NT was detected by MS analysis solely in RLMVEC P with 10 MS/MS spectra, but Western analysis of both lung P and RLMVEC P detected it enriched in P over H, albeit with far more expression in RLMVEC P. The amount of 5'NT in rat lung P might have been below the detection sensitivity of the MS analysis.

A newly identified hypothetical protein designated FLJ10849 with high homology to septin proteins was identified both in vivo and in vitro. Another hypothetical protein, a homolog to KIAA0417 that contains an HSP70 motif, was identified solely in rat lung P. Western analysis using polyclonal antibodies against specific peptide sequences derived from the deduced amino acid sequence showed a band at 59 kDa (FLJ10849) and 82 kDa (HSPA12B) consistant with the predicted molecular weight of these proteins. This analysis confirmed the MS findings as well as the actual existence of these proteins listed as hypothetical in the database.

In addition to the 12 proteins (ACE, aquaporin, CA, ECE, RAGE, VE-cadherin, caveolin-1, 5'NT, ZO-2, podocalyxin, Lyn, HSP47) confirmed biochemically that are known to be expressed in endothelial cells, the enrichment in P of TIE-2, APN, ICAM-1, and nucleolin whose expression has been reported previously not normally in endothelial cells but during angiogenesis and/or inflammation was verified. In addition, some proteins were discovered such as P2Z receptor and Trk-A, that have not previously been localized to endothelial cells but rather neuronal cells and tissues. Thus, for 16 of the proteins validated by Western analysis, there are reports of endothelial expression at least under some conditions. These findings appear novel for the other 6 proteins (Trk-A, P2Z receptor, seven transmembrane receptor, Na—H exchanger regulatory factor 2, HSPA12B, Septin homolog FLJ10849).

Tissue immunostaining of select proteins. Immunohistochemical staining of rat lung tissue sections was used to validate endothelial cell expression of proteins identified by our MS analysis. Antibodies good for Western analysis do not necessarily work well by tissue immunostaining and vice versa. So far, these data further validate the in vivo expression of 27 proteins (chosen randomly by availability of antibodies suitable for immunohistochemistry). For example, ACE, CD26, HSPA12B, OX-45, P2Z receptor (P2×7), NHERF-2, Pincher, PV-1, podocalyxin, and PECAM, were expressed on lung blood vessels. Other proteins (caveolin-1, ECE, aquaporin 1, Nedd5, CA, TIE2, RAGE, EphA4, EphA7, Glut4, ZO-1, neurophilin, I-CAM, Vitamin D binding protein, thrombomodulin, CD39, and aminopeptidase P) were similarly detected on lung endothelium (data not shown). Tissues stained with secondary antibody alone were negative. These data provide independent validation of the presence on lung endothelium of these proteins identified through tissue subfractionation, MS analysis, and database searching. Thus, the presence on lung endothelium of many proteins identified through our MS analysis that have not been described previously on endothelium (e.g. Trk-A, P2X7, seven transmembrane receptor, NHERF-2, HSPA12B, pincher, Nedd 5, Glut4) was validated.

Discussion

Diversity of identified proteins. Based on the current rat database, 74% of the proteins identified in the isolated endothelial cell surface have some characterization, including information on function, structure, and/or localization. But 26% do not and are categorized as not-yet-defined in the rat database. Just based on the current literature, >80% of these better characterized proteins already have some good reason and even actual experimental evidence for association with the plasma membrane. Yet, in spite of rigorous quality testing of each membrane preparation by Western analysis, some proteins were found by MS that at first may not appear to belong in the plasma membrane fraction, including cytsolic and blood proteins as well as proteins reportedly associated with intracellular organelles.

Consistent with the flushing of the lung vasculature free of blood, quality control tests have detected little to no presence of well-known marker proteins for red and white blood cells in P. Nevertheless, 21 known blood proteins have been identified in the MS analysis. Given that there are >500 known blood plasma proteins and even more blood cell proteins, this number appears too low for it to be simply contamination. In fact, the presence of such a very small percentage of blood proteins may be legitimately expected in rat lung P and even RLMVEC (grown in serum). For example, albumin (16 distinct MS/MS spectra detected) and transferrin (7 spectra) can interact specifically with the endothelial cell surface via specific binding proteins or receptors (Jeffries, W. A. et al. Transferrin receptor on endothelium of brain capillaries. Nature 312, 162-163 (1984); Schnitzer, J. E. & Oh, P. Albondin-mediated capillary permeability to albumin. Differential role of receptors in endothelial transcytosis and endocytosis of native and modified albumins. Journal of Biological Chemistry 269, 6072-6082 (1994); Schnitzer, J. E. gp60 is an albumin-binding glycoprotein expressed by continuous endothelium involved in albumin transcytosis. American Journal of Physiology 262, H246-254 (1992)). Hemoglobin alpha and beta chain (12 and 5 spectra, respectively) may come from small amounts of cell-free hemoglobin in the blood rather than simply red blood cell contamination, especially in light of the lack of erythrocyte markers in P.

Likewise, proteins were detected that are currently considered to be primarily located in ER, mitochondria, Golgi network, ribosomes, and nuclei, which cumulatively were about 15% of the proteins identified in total (20% of the characterized proteins). But, given our stringent quality criteria of 20-fold enrichment of EC markers and 20-fold depletion of specific markers of these subcellular organelles, we may expect 5% contaminants. Thus, general contamination of membranes from these organelles seems remote, even more so if one considers the few, not so prevalent proteins identified (~15 average per organelle) relative to the many hundreds of proteins in each organelle. Of course, it is possible that some of the polycationic proteins, such as histones and basic ribosomal subunit proteins, are released by tissue homogenization and can adsorb to the silica-coated membranes, especially electrostatically to the polyanionic polyacrylic acid crosslinker. Yet, it seems more likely that most of these proteins just simply reside in more than one subcellular location. It is not unusual that proteins, that were categorized as organelle-specific for years, may subsequently be discover to be expressed elsewhere in the cell. Here are four such examples of proteins identified in P and classified in one of these four groups. Nucleolin is a well-characterized nuclear protein but is expressed also at the cell surface (Christian, S. et al. Nucleolin expressed at the cell surface is a marker of endothelial cells in angiogenic blood vessels. J Cell Biol 163, 871-878 (2003)). Elongation factor-1 alpha is known primarily as a component of the protein synthesis machinery but has a less well-known function in cytoskeletal re-organization (Negrutskii, B. S. & El'skaya, A. V. Eukaryotic translation elongation factor 1 alpha: structure, expression, functions, and possible role in aminoacyl-tRNA channeling. Prog Nucleic Acid Res Mol Biol 60, 47-78 (1998)). Protein disulfide isomerase, which is commonly classified as an ER protein, has recently been detected at the plasma membrane of platelets and liver (Honscha, W., Ottallah, M., Kistner, A., Platte, H. & Petzinger, E. A membrane-bound form of protein disulfide isomerase (PDI) and the hepatic uptake of organic anions. Biochim Biophys Acta 1153, 175-183 (1993)). Hsp47 was initially assigned to the ER, but later discovered to be transported to the plasma membrane (Hebert, C. et al. Cell surface colligin/Hsp47 associates with tetraspanin protein CD9 in epidermoid carcinoma cell lines. J Cell Biochem 73, 248-258 (1999)). Thus, this analysis may provide, for some of these proteins, the first evidence of a seconday localization at the plasma membrane.

Proteins associated with the plasma membrane that are not integral membrane proteins or lipid-anchored may exist in our preparation through protein complex formation and interaction partners. For example, sodium hydrogen exchanger regulatory factor 2 (NHERF-2) is not membrane-bound but rather associates with podocalyxin, a pan-endothelial integral membrane protein marker (Horvat, R., Hovorka, A., Dekan, G., Poczewski, H. & Kerjaschki, D. Endothelial cell membranes contain podocalyxin—the major sialoprotein of visceral glomerular epithelial cells. J Cell Biol 102, 484-491 (1986)), via its PDZ domain (Li, Y., Li, J., Straight, S. W. & Kershaw, D. B. PDZ domain-mediated interaction of rabbit podocalyxin and Na(+)/H(+) exchange regulatory factor-2. Am J Physiol Renal Physiol 282, F 129-1139 (2002)). NHERF-2 in turn interacts with ezrin and EBP50-PDZ interactor (Reczek, D. & Bretscher, A. Identification of EPI64, a TBC/rabGAP domain-containing microvillar protein that binds to the first PDZ domain of EBP50 and E3KARP. J Cell Biol 153, 191-206 (2001)), both of which were also identified in rat lung P. Another example is dedicator of cytokinesis protein 1 (Dock 180), which is recruited to the plasma membrane via its interaction with phosphatidylinositol 3,4,5-triphosphate (Brugnera, E. et al. Unconventional Rac-GEF activity is mediated through the Dock180-ELMO complex. Nat Cell Biol 4, 574-582 (2002)) where it has been implicated in regulation of cytoskeletal rearrangements required for cell motility (Cote, J. F. & Vuori, K. Identification of an evolutionarily conserved superfamily of DOCK180-related proteins with guanine nucleotide exchange activity. J Cell Sci 115, 4901-4913 (2002)). Moreover, its activation has been found to be enhanced by binding to engulment and cell motility proteins (ELMO) 1 and 2, also found in P. Such similar interactions may explain the presence of many cytosolic and even other proteins in our preparation because of yet to be discovered recruitments.

Upon consideration of these issues, the list of identified proteins seems rather consistent with the quality control data showing 95% purity of the isolated membranes (based on 20-fold enrichment for EC markers and 20-fold depletion in markers of other cell types as well as cellular organelles).

Distinct endothelial cell surface proteome in vivo vs. in vitro. Comparative proteomic analysis of endothelial cell surface membranes isolated from rat lung vs. cultured RLMVEC reveal striking differences. Only ~51% of the integral membrane proteins and plasma membrane-associated proteins identified were expressed in common between rat lung P and RLMVEC P. Interestingly, 65 of 73 (89%) total known endothelial cell marker proteins detected in this study are found in rat lung P vs. only 32 (43.8%) are in RLMVEC P (Table 2). 41 known markers, such as ACE and ECE, were detected in rat lung P but not RLMVEC P. Overall, more than 180 (41%) proteins are detected in rat lung P in vivo but not RLMVEC P in vitro.

The tight junction protein ZO-2 is readily detected by MS in rat lung P but not in RLMVEC. Western analysis and immunofluorescence (our unpublished observations) confirms the expression of ZO-2 in RLMVEC cells. It is in the total cell lysate (H) and not P. The lack of ZO-2 and other junctional complex proteins (VE-cadherins and ZO-1) in RLMVEC P but not rat lung P suggest that the junctional complex remains in P from tissue but not cultured endothelial cell monolayers. The intercellular junctions of endothelial cells in vivo are more developed and tighter than those in culture so that during homogenization of the lung tissue, membrane breakage may occur to include along with the rest of the silica-coated plasma membranes only the junctions that are tightly interdigitated.

It has become quite apparent through studying vasculogenesis, angiogenesis, and the modulation of endothelial cell phenotype in culture and in vivo that the morphology, protein expression, and function of vascular endothelial cells are impacted greatly by physical and molecular cues from the basement membrane, perivascular cells, the circulating blood, and even from other cells deeper within the tissue (Madri, J. A. & Williams, S. K. Capillary endothelial cell culture: Phenotype modulation by matrix components. J. Cell Biol. 97, 153-165 (1983); St Croix, B. et al. Genes expressed in human tumor endothelium. Science 289, 1197-1202 (2000); Rizzo, V., Morton, C., DePaola, N., Schnitzer, J. E. & Davies, P. F. Recruitment of endothelial caveolae into mechanotransduction pathways by flow conditioning in vitro. Am J Physiol Heart Circ Physiol 285, H1720-1729 (2003); Schnitzer, J. The endothelial cell surface and caveolae in health and disease. Book chapter: Vascular Endothelium: Physiology, Pathology and Therapeutic Opportunities eds.: G. V. R. Bora, C. J. Schwartz, 77-95 (1997)). Current standard, albeit limited, cell culture conditions not only appear unable to maintain the expression of the proteins found in vivo but also may allow the expression of other proteins not easily detected in vivo. The differences in molecular expression are likely to have functional consequences that limits the utility of current endothelial cells in culture. Here, a glimpse is provided of how wide the microenvironment-induced molecular chasm can be for endothelial cells existing natively in vivo vs. artificially under standard conditions in vitro. Of course, some of this molecular gap may relate to the derivation of the RLMVEC from one part of the pulmonary vasculature. Microvascular endothelial cell plasma membranes dominate the membranes isolated using the silica coating technique because >90% of vascular surface area in tissue comes from microvesels (arterioles, capillaries, and venules).

The differential protein map of endothelial cells in vivo vs. in vitro begins to identify an extensive, yet initial, set of potentially promising tissue-modulated endothelial cell markers that can now be used to monitor future advancements in tissue engineering toward reproducing native endothelial cell phenotype in vitro and may aid in bringing about a deeper understanding of how the tissue environment controls endothelial cell phenotype.

Representative findings. In addition to identifying multiple known plasma membrane and endothelial cell marker proteins, a number of proteins were also detected unexpectedly, such as TIE-2, APN, TEM4, TEM6, ICAM-1, and nucleolin. TIE2 and ICAM-1 expression in lung endothelium was also validated by tissue immunostaining whereas APN and nucleolin were detected by Western analysis enriched in lung P. These molecules are all thought to be endothelial markers induced during angiogenisis and/or inflammation despite being clearly present in rat lung P from multiple samples. Given the mechanical forces involved with respiration, lung endothelium may undergo recurrent damage requiring more self-renewal and be less quiescent than in other tissues. Conversely, the inherent highly oxygenated state of the tissue would render unlikely typical triggers of angiogenesis, such as hypoxia. In the end, strategies of targeting tumors through these proteins should assess possible lung targeting in vivo.

Two neuronal receptors were also identified, P2Z receptor (P2X7) and Trk-A (Deuchars, S. A. et al. Neuronal P2X7 receptors are targeted to presynaptic terminals in the central and peripheral nervous systems. J Neurosci 21, 7143-7152 (2001); Esposito, D. et al. The cytoplasmic and transmembrane domains of the p75 and Trk A receptors regulate high affinity binding to nerve growth factor. J Biol Chem 276, 32687-32695 (2001)). Although Trk-A (isoform I) can be expressed in a wide range of non-neuronal tissues such as connective tissue (fibroblasts), kidney, lung, breast and esophagus (Barker, P. A. et al. Tissue-specific alternative splicing generates two isoforms of the trkA receptor. J Biol Chem 268, 15150-15157 (1993); Koizumi, H., Morita, M., Mikami, S., Shibayama, E. & Uchikoshi, T. Immunohistochemical analysis of TrkA neurotrophin receptor expression in human non-neuronal carcinomas. Pathol Int 48, 93-101 (1998)), this is apparently the first time that either of these neuronal cell surface receptors are detected at the endothelial cell surface. Given the enrichment in P and the lack of previous detection in lung tissue (Deuchars, S. A. et al. Neuronal P2X7 receptors are targeted to presynaptic terminals in the central and peripheral nervous systems. J Neurosci 21, 7143-7152 (2001)), their endothelial cell surface expression appears rea and may reflect the high sensitivity of this analytical approach. Other proteins, such as aquaporin and synaptobrevin, previously thought to be specific for other cell types (epithelial and neuronal, respectively) have also been discovered in endothelium using similar tissue subfractionation techniques (Schnitzer, J. E., Liu, J. & Oh, P. Endothelial caveolae have the molecular transport machinery for vesicle budding, docking, and fusion including VAMP, NSF, SNAP, annexins, and GTPases. J. Biol. Chem. 270, 14399-14404 (1995); Schnitzer, J. E. & Oh, P. Aquaporin-1 in plasma membrane and caveolae provides mercury-sensitive water channels across lung endothelium. Am J Physiol 270, H416-422 (1996)). The P2X7 andtibody is effective for both Western analysis and tissue immunostaining so that we have confirmed P2X7 expression on lung endohtelium on frozen tissue sections.

In addition to known proteins, also detected were a number of yet-to-be-characterized proteins (25%). This group includes proteins discovered through EST and cDNA cloning initiatives as well as proteins that are "similar to a known gene from the human or mouse database" predicted by automated annotation of the rat genome. These predicted proteins require further structural and functional characterization before they can be classified outside this category. Specific antibodies were generated to two proteins (FLJ10849 and HSPA12B) in this category for validation of the MS findings. FLJ10849 is a hypothetical protein supported by expressed sequence tag (EST) evidence that was identified with good sequence coverage (28.6%; 18 spectra; Table 1). A BLAST search of the sequence revealed its closest relative to be human septin 6 with 81% identity and a pfam search showed that it contained a CDC_GTP motif that is common to proteins involved in cell division as well as in endocytosis or GTP-driven vesicle formation (Kartmann, B. & Roth, D. Novel roles for mammalian septins: from vesicle trafficking to oncogenesis. J Cell Sci 114, 839-844 (2001)). HSPA12B, identified in rat lung P (26 spectra, 28.4% coverage of the predicted primary sequence), is an apparent member of the Hsp70 super family (Table 2). HSPA12B is supported by EST findings and Northern analysis reveals expression in atherosclerotic lesions (Han, Z., Truong, Q. A., Park, S. & Breslow, J. L. Two Hsp70 family members expressed in atherosclerotic lesions. Proc Natl Acad Sci USA 100, 1256-1261 (2003)). HSPA12B expression was also confirmed in the lung endothelium by tissue immunostaining, but, unfortunately, the FLJ10849 antibody was suboptimal and gave significant background staining. They are both enriched in P relative to H so that it is very likely that they both are indeed expressed at the lung endothelial cell surface. This is the first time that the translation of these 2 proteins has been confirmed on a primary sequence level. Protein validation. Given that a protein not identified by MS out of a complex mixture is not necessarily absent in the sample, we have used Western analysis to test for many proteins not detected in RLMVEC P. 87.5% of the tested proteins that are not detected in RLMVEC by MS are also not detected by Western analysis and 91% of all tested proteins that are detected in either rat lung or RLMVEC P are confirmed by Western analysis. All detected protein bands agree with the predicted molecular weights and, given the relative specificity of each antibody this analysis provides good evidence that the peptides identified by MS truly corresponded to the identified proteins. Yet, it remains problematic that the public protein databases are as yet incomplete so that one cannot rule out the possibility for the existence of other, yet-to-be-identified proteins that share peptide sequences. Western analysis also has the advantage of providing quantitative information on the relative levels of each protein. Proteins depleted in P relative to total cell/tissue lysate (H) have a greater probability of being contaminants revealed by the high sensitivity of the mass spectrometer whereas proteins enriched in P over H are expected rarely to be contaminants.

Immunohistochemical staining of lung tissue can also validate lung endothelial cell expression of identified proteins but, unfortunately, many antibodies do not work both in Western analysis and immunohistology. Proteins are denatured to varying degrees after SDS-PAGE and transfer to filters whereas proteins in frozen tissue may be more native in structure and may be interacting with other proteins to block possible antibody reactivity. Tissue immunostaining can be extremely laborious and time consuming requiring careful preparation and optimization. In our experience of testing >500 antibodies in the last decade, 50% of all the antibodies that we get either from other labs or from commercial sources are not monospecific by Western analysis and thus cannot be used for immunohistochemistry: at least 50% of these monospecific antibodies do not work for tissue immunostaining.

Analytical completeness. The statistical analysis to estimate the "confidence of completeness" provides what appears to be a useful gauge not only of the reproducibility and relative comprehensiveness of individual MudPIT measurements but, perhaps more importantly, of the number of measurements required to achieve a statistically defined level of completeness possible with the current instrumentation and database. The more complex the peptide mixture and the bigger the dynamic range, the more unlikely it will be that the acquisition of tandem mass specta will be exactly reproduced. Certainly, the reproducibility depends on the complexity of the sample as well as the reproducible quality and composition of peptides from independent sample preparations originating from different animals. Thus, it seems prudent to perform a statistical analysis from several measurements to assess this variation and to estimate the degree to which the sample can be comprehensively described with a given amount of independent measurements. The analysis here has required 7-10 MudPit measurements to achieve >95% "confidence of analytical completeness" possible with the current equipment, database, and analytical approach. Improving the sample preparation prior to the mass spectrometric analysis and chromatographic separation as well as increasing the sensitivity of the mass spectrometer and completion of the rat protein database will lead to a more comprehensive map of the endothelial cell surface. Context and Summary. This work represents the first large-scale proteomic analysis of the luminal endothelial cell surface of a specific organ vascular bed. 450 proteins have been identified with a rigorous identification criteria 3 peptides. This is an improvement over many proteomic analyses in the past that have found similar numbers of proteins in whole cells, bacteria, yeast and tissue preparations but usually with selection criteria based on one and two peptides (Washburn, M. P., Wolters, D. & Yates, J. R., 3rd Large-scale analysis of the yeast proteome by multidimensional protein identification technology. Nature Biotechnology 19, 242-247 (2001)). Moreover, two MS analyses of whole cultured endothelial cells have recently identified in total <60 proteins, including only a few proteins found here: hemoglobin, albumin, heat shock proteins, actin, nucleophosmin, vimentin, and tubulins (Obermeyer, N., Janson, N., Bergmann, J., Buck, F. & Ito, W. D. Proteome analysis of migrating versus nonmigrating rat heart endothelial cells reveals distinct expression patterns. Endothelium 10, 167-178 (2003); Bruneel, A. et al. Proteomic study of human umbilical vein endothelial cells in culture. Proteomics 3, 714-723 (2003)). These 2-D gel studies did not identify any cell surface enzymes or transmembrane proteins, including G-protein coupled receptors.

This more detailed understanding of the proteome of specialized cell types will pave the way to understand the way these cells fulfill their biological function in a systems biological context. Differences in the protein expression pattern between differentiated cells as well as changes occurring during disease are of great interest in experimental medicine for diagnosis and treatment. Moreover, mapping the proteins expressed at the luminal surface of the vascular endothelium may have great value clinically because proteins expressed at this blood-tissue interface are inherently accessible to the circulating blood and may have utility as pharmacological targets, as shown recently (McIntosh, D. P., Tan, X. Y., Oh, P. & Schnitzer, J. E. Targeting endothelium and its dynamic caveolae for tissue-specific transcytosis in vivo: a pathway to overcome cell barriers to drug and gene delivery. Proc Natl Acad Sci USA 99, 1996-2001 (2002)).

Example 2

Subtractive Proteomic Mapping of the Endothelial Surface in Lung for Tissue-Specific Therapy The methods described above were further used to investigate endothelial cell surface heterogeneity in vivo. Subcellular fractionation was performed to isolate luminal endothelial cell plasma membranes (P) and caveolae (V) directly from normal organs (Oh, P. & Schnitzer, J. E. in Cell Biology: A Laboratory Handbook (ed. Celis, J.) 34-36 (Academic Press, Orlando, 1998); Schnitzer, J. E., McIntosh, D. P., Dvorak, A. M., Liu, J. & Oh, P. Separation of caveolae from associated microdomains of GPI-anchored proteins. Science 269, 1435-9 (1995)). P and V displayed 20-fold enrichment for endothelial cell surface and caveolar markers (angiotensin converting enzyme (ACE), VE-cadherin, and caveolin-1) whereas proteins of intracellular organelles (e.g. -COP for Golgi), other tissue cells (e.g. E-cadherin for epithelium, fibroblast surface protein), and blood (e.g. glycophorin A, CD4, CD11) were 20-fold depleted (data not shown; data in accordance with previous results (Schnitzer, J. E. in Vascular Endothelium: Physiology, pathology and therapeutic opportunities. (eds. Born, G. V. R. & Schwartz, C. J.) 77-95 (Schattauer, Stuttgart, 1997); Oh, P. & Schnitzer, J. E. in Cell Biology: A Laboratory Handbook (ed. Celis, J.) 34-36 (Academic Press, Orlando, 1998); Schnitzer, J. E., McIntosh, D. P., Dvorak, A. M., Liu, J. & Oh, P. Separation of caveolae from associated microdomains of GPI-anchored proteins. Science 269, 1435-9 (1995)). This quality control was applied to each isolate. Schnitzer, J. E. et al. J. Biol. Chem. 270:14399-14404 (1995).

P was analyzed by 2-D gel electrophoresis to produce high-resolution vascular endothelial protein maps of the major rat organs that were distinct and much reduced in complexity from that of the starting tissue homogenate (data not shown). Differential spot analysis revealed many distinct proteins in P vs. the homogenate and in P between organs, and Western analysis confirmed this heterogeneity further. In many cases, antigens difficult to detect in tissue homogenates were readily apparent in P, reflecting the significant enrichment and increased sensitivity provided by subfractionation to unmask proteins located on the endothelial cell surface. Unique "molecular fingerprints or signatures" that may include tissue- and cell-specific proteins were apparent for each endothelia. To identify specific proteins expressed at the endothelial cell surface, mass spectrometry (MS) and database searching was utilized as well as immunoblotting to analyse P and V isolated from rat tissues (Oh, P. & Schnitzer, J. E. in Cell Biology: A Laboratory Handbook (ed. Celis, J.) 34-36 (Academic Press, Orlando, 1998); Schnitzer, J. E., McIntosh, D. P., Dvorak, A. M., Liu, J. & Oh, P. Separation of caveolae from associated microdomains of GPI-anchored proteins. Science 269, 1435-9 (1995)) as well as cultured rat lung microvascular endothelial cells (RLMVEC) isolated and grown in culture (Schnitzer, J. E. gp60 is an albumin-binding glycoprotein expressed by continuous endothelium involved in albumin transcytosis. Am J Physiol 262, H246-54 (1992)). We identified so far nearly 2000 non-redundant proteins (Table 1) which were entered into a database (AVATAR; Accessible Vascular Targets) designed and annotated in-house to provide relational analysis between measurements and samples. To discover lung-induced and possibly even lung-specific endothelial cell surface proteins, a systems biology approach was employed based on the central hypothesis that the surrounding tissue microenvironment, whether normal or diseased, ultimately modulates protein expression in the vascular endothelium. The proteins identified in P from rat lungs vs. RLMVEC were subtracted in silico because tissue-dependent protein expression may be reduced in cell culture that cannot yet duplicate conditions in vivo. To increase certainty of expression in vivo vs. in vitro, a strict identification criterion of 6 MS/MS spectra to rat lung P vs. low stringency of 1 spectra to RLMVEC P was applied. From the current rat database of 40,000 entries, 37 differentially expressed proteins were identified. To meet the objective of direct exposure to circulating antibodies, bioinformatic interrogation of structure, glycosylation, and membrane-orientation was applied to reduce the list to 11 proteins likely to have domains outside the cell.

To confirm the original MS findings and to assess organ-specificity, expression profiling was performed with specific antibodies. Consistent with the hypothesis, Western analysis detected each of these 11 proteins enriched in lung P vs. total lung homogenate but not in RLMVEC P (data not shown). Each of these proteins exhibited a different pattern of restricted expression. Two proteins, aminopeptidase P (APP) and OX-45, were detected only in P from lung. Staining of tissue sections with antibodies (including to APP and OX-45) confirmed this restricted expression (data not shown). This profiling by Western analysis was very sensitive and reliable, even at low expression levels. This subtractive proteomic analysis provided a subset of endothelial cell proteins not expressed in vitro and differentially expressed in vivo, apparently regulated by the unique tissue microenvironment in each organ.

To assess the immuno-accessibility of APP and OX45 in vivo, including possible lung-specific targeting, 125I-labeled monoclonal antibodies were intravenously-injected into rats and whole body imaging performed using planar scintigraphy. Within 20 min, clear lung images were observed, indicating rapid and specific targeting of APP antibody to the lung (data not shown). Region-of-interest and biodistribution analysis confirmed lung-specific targeting at 20 min with 65% of the injected dose (ID)/g of tissue accumulating in the lungs and <2% ID/g in other organs and blood. Consistent with the low blood levels, the heart cavity was readily apparent. This lung targeting was inhibited by addition of 50-fold excess of unlabeled APP IgG but not control IgG (data not shown) and thus depends on the specific ability of the antibodies to bind APP exposed on the endothelial cell surface of the lung but not other organs.

Consistent with OX-45 expression in various leukocytes (Henniker, A. J., Bradstock, K. F., Grimsley, P. & Atkinson, M. K. A novel non-lineage antigen on human leucocytes: characterization with two CD-48 monoclonal antibodies. Dis Markers 8, 179-90 (1990)), we detected OX-45 but not APP in blood. Thus, imaging with OX-45 antibody showed little targeting to the lung (data not shown). Biodistribution analysis confirmed only 2% ID accumulating in the lung and >70% ID remaining in the blood, primarily bound to the buffy coat subfraction of the blood.

APP was reported to be expressed on mouse blood vessels of normal breast and mammary adenocarcinomas as a target for a homing peptide (Essler, M. & Ruoslahti, E. Molecular specialization of breast vasculature: a breast-homing phage-displayed peptide binds to aminopeptidase P in breast vasculature. Proc Natl Acad Sci USA 99, 2252-7 (2002)). High resolution single photon emission computed tomography (SPECT) imaging of 125I-APP antibodies injected intravenously into female rats detected no accumulation in normal breast tissue nor in primary or metastatic breast tumor lesions (multiple images taken over 36 hours (data not shown)). SPECT imaging provided a clear three dimensional view of normal lungs in striking contrast to the irregular images with multiple nodular regions lacking signal in rats with mammary adenocarcinomas in the lung. Thus, APP expression in the rat was specific for normal lung tissue and apparently induced by conditions present in the normal lung tissue microenvironment but absent in the tumour milieu in vivo, even when the tumour blood vessels are derived from the normal lung vasculature.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of delivering an agent to, into and/or across vascular endothelium in vivo in a lung-specific manner, comprising contacting the luminal surface and/or caveolae of vasculature in vivo with the agent, wherein the agent comprises an antibody or an antibody fragment, and wherein the antibody or antibody fragment specifically binds to aminopeptidase P expressed on endothelial cell surface.

2. A method of delivering an imaging agent in vivo in a mammal in a lung-specific manner, comprising contacting the luminal surface and/or caveolae of vasculature in vivo with the imaging agent, wherein the imaging agent comprises an imaging agent component and a targeting agent component, wherein the targeting agent component comprises an antibody or antibody fragment that specifically binds to aminopeptidase P expressed on endothelial cell surface, and wherein the imaging agent component is selected from the group consisting of: a radioactive agent, a radioisotope, a radiopharmaceutical, a contrast agent, a nanoparticle; an enzyme, a prosthetic group, a fluorescent material, a luminescent material, and a bioluminescent material.

* * * * *